US009708333B2

(12) United States Patent
Li et al.

(10) Patent No.: US 9,708,333 B2
(45) Date of Patent: Jul. 18, 2017

(54) FUSED BICYCLIC 1,2,4-TRIAZINE COMPOUNDS AS TAM INHIBITORS

(71) Applicant: Incyte Corporation, Wilmington, DE (US)

(72) Inventors: Yun-Long Li, Chadds Ford, PA (US); David M. Burns, Plymouth Meeting, PA (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 15/234,690

(22) Filed: Aug. 11, 2016

(65) Prior Publication Data

US 2017/0044164 A1    Feb. 16, 2017

Related U.S. Application Data

(60) Provisional application No. 62/204,131, filed on Aug. 12, 2015.

(51) Int. Cl.
*C07D 487/04* (2006.01)
*C07D 403/04* (2006.01)
*C07D 403/14* (2006.01)
*A61K 31/53* (2006.01)

(52) U.S. Cl.
CPC ............ *C07D 487/04* (2013.01); *A61K 31/53* (2013.01); *C07D 403/04* (2013.01); *C07D 403/14* (2013.01)

(58) Field of Classification Search
CPC .. C07D 487/04; C07D 403/04; C07D 403/14; A61K 31/53
USPC .......................................... 544/184; 514/243
See application file for complete search history.

(56) References Cited

U.S. PATENT DOCUMENTS

| | | |
|---|---|---|
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0015937 A1 | 1/2012 | Ding et al. |
| 2012/0088768 A1 | 4/2012 | Singh et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0184535 A1 | 7/2012 | Brzozka et al. |
| 2012/0219522 A1 | 8/2012 | Xi |
| 2012/0230993 A1 | 9/2012 | Graham et al. |
| 2012/0264740 A1 | 10/2012 | Goff et al. |
| 2012/0283261 A1 | 11/2012 | Bearss et al. |
| 2013/0018034 A1 | 1/2013 | Yao et al. |
| 2013/0018051 A1 | 1/2013 | Singh et al. |
| 2013/0045963 A1 | 2/2013 | Rodgers et al. |
| 2013/0059835 A1 | 3/2013 | Li et al. |
| 2013/0090330 A1 | 4/2013 | Ding et al. |
| 2013/0197070 A1 | 8/2013 | De Franciscis et al. |
| 2013/0281468 A1 | 10/2013 | Goff et al. |
| 2014/0005166 A1 | 1/2014 | Rodgers et al. |
| 2014/0018365 A1 | 1/2014 | Schultz-Fademrecht et al. |
| 2014/0121198 A1 | 5/2014 | Li et al. |
| 2014/0128400 A1 | 5/2014 | Singh et al. |
| 2014/0275023 A1 | 9/2014 | Namdev et al. |
| 2016/0333008 A1 | 11/2016 | Sun et al. |

FOREIGN PATENT DOCUMENTS

| | | |
|---|---|---|
| CN | 102408411 | 4/2012 |
| EP | 2484679 | 8/2012 |
| WO | WO 2004/035580 | 4/2004 |
| WO | WO 2005/025515 | 3/2005 |
| WO | WO 2006/046023 | 5/2006 |
| WO | WO 2007/061737 | 5/2007 |
| WO | WO 2007/070514 | 6/2007 |
| WO | WO 2007/120752 | 10/2007 |
| WO | WO 2007/125315 | 11/2007 |
| WO | WO 2008/076392 | 6/2008 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2010/005876 | 1/2010 |

(Continued)

OTHER PUBLICATIONS

Lemke G., Cold Spring Harb Perspect Biol 2013;5:1-17.*
Cecil Textbook of Medicine, edited by Bennet, J.C., and Plum F., 20th edition,vol. 1, 1004-1010, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*

(Continued)

*Primary Examiner* — Venkataraman Balasubramanian
(74) *Attorney, Agent, or Firm* — Fish & Richardson P.C.

(57) ABSTRACT

This application relates to compounds of Formula I:

I or pharmaceutically acceptable salts thereof, which are inhibitors of TAM kinases which are useful for the treatment of disorders such as cancer.

14 Claims, No Drawings

(56) References Cited

FOREIGN PATENT DOCUMENTS

| WO | WO 2010/005879 | 1/2010 |
|---|---|---|
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2016/097918 | 6/2016 |

OTHER PUBLICATIONS

Burbridge et al., "S49076 Is a Novel Kinase Inhibitor of MET, AXL, and FGFR with Strong Preclinical Activity Alone and in Association with Bevacizumab," AACR Journals, 2013, 1749-1762.

Berge, "Pharmaceutical Salts," Journal of Pharmaceutical Science, 66, 2 (1977).

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chromatography-Mass Spectrometry," J. Comb. Chem., 2002, 4: 295-301.

Chambers et al., "Lymphoproliferation in CTLA-4-deficient mice is mediated by costimulation-dependent activation of CD4+ T cells," Immunity, Dec. 1997, 7(6): 885-95.

Cook et al., "MerTK inhibition in tumor leukocytes decreases tumor growth and metastasis," J. Clin. Invest., Aug. 2013, 123(8): 3231-42.

Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.

Feneyrolles et al., "Axl kinase as a key target for oncology: focus on small molecule inhibitors," Mol Cancer Therapy, Sep. 2014, 13(9): 2141-8.

Graham et al., "Cloning and developmental expression analysis of the murine c-mer tyrosine kinase," Oncogene, Jun. 1995, 10(12): 2349-59.

Graham et al., "The TAM family: phosphatidylserine sensing receptor tyrosine kinases gone awry in cancer," Nat. Rev. Cancer, Dec. 2014, 14(12): 769-85.

Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.

Huang et al., "Structural insights into the inhibited states of the Mer receptor tyrosine kinase," Journal of Structural Biology, 2009, 165: 88-96.

International Search Report and Written Opinion in International Application No. PCT/US2016/031625, dated Jul. 7, 2016, 11 pages.

Koorstra et al., "The Axl receptor tyrosine kinase confers an adverse prognostic influence in pancreatic cancer and represents a new threapeutic target," Cancer Biol. Ther., Apr. 2009, 8(7): 618-26.

Lai and Lemke, "An extended family of protein-tyrosine kinase genes differentially expressed in the vertebrate nervous system," Neuron, May 1991, 6(5): 691-704.

Lee-Sherick et al., "Aberrant Mer receptor tyrosine kinase expression contributes to leukemogenesis in acute myeloid leukemia," Oncogene, Nov. 2013, 32(46): 5359-68.

Lew et al., "Differential TAM receptor-ligand-phospholipid interactions delimit differential TAM bioactivities," Elife, Sep. 2014, e03385.

Li et al., "Axl as a potential therapeutic target in cancer: role of Axl in tumor growth, metastasis and angiogenesis," Oncogene, Oct. 2009, 28(39): 3442-55.

Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-31.

Linger et al., "Taking aim at Mer and Axl receptor tyrosine kinases as novel therapeutic targets in solid tumors," Expert Opin. Ther. Targets, Oct. 2010, 14(10): 1073-1090.

Linger et al., "TAM Receptor Tyrosine Kinases: Biologic Functions, Signaling, and Potential Therapeutic Targeting in Human Cancer," Adv. Cancer Research, 2008, 100: 35-83.

Liu et al., "Discovery of Novel Small Molecule Mer Kinase Inhibitors for the Treatment of Pediatric Acute Lymphoblastic Leukemia," ACS Med. Chem. Lett., 2012, 3(2): 129-134.

Liu et al., "Discovery of Novel Small Molecule Mer Kinase Inhibitors for the Treatment of Pediatric Acute Lymphoblastic Leukemia," Supporting Information, 53 pages.

Liu et al., "Discovery of Small Molecule Mer Kinase Inhibitors for the Treatment of Pediatric Acute Lymphoblastic Leukemia," ACS Medicinal Chemistry Letters, 2012, 3: 129-134.

Lu and Lemke, "Homeostatic regulation of the immune system by receptor tyrosine kinases of the Tyro 3 family," Science, Jul. 2001, 293(5528): 306-11.

Mollard et al., "Design, Synthesis, and Biological Evaluation of a Series of Novel AXL Kinase Inhibitors," ACS Medicinal Chemistry Letters, 2011, 2: 907-912.

Myers et al., "AXL inhibitors in cancer: A medicinal chemistry perspective," Journal of Medicinal Chemistry, 2015, 54 pages.

Nishimura et al., "Autoimmune dilated cardiomyopathy in PD-1 receptor-deficient mice," Science, 2001, 291(5502): 319-22.

O'Bryan et al., "axl, a transforming gene isolated from primary human myeloid leukemia cells, encodes a novel receptor tyrosine kinase," Mol. Cell Biol., Oct. 1991, 11(10): 5016-31.

Paolino et al., "The E3 ligase Cbl-b and TAM receptors regulate cancer metastasis via natural killer cells," Nature, 2014, 19 pages.

Pardoll, "The blockade of immune checkpoints in cancer immunotherapy," Nat. Rev. Cancer, Mar. 2012, 12(4): 252-64.

Powell et al., "Highly selective 2,4-diaminopyrimidine-5-carboxamide inhibitors of Sky kinase," Bioorganic & Medicinal Chemistry Letters, 2013, 23: 1046-1050.

Powell et al., "Novel and selective spiroindoline-based inhibitors of sky kinase," Bioorganic & Medicinal Chemistry Letters, 2012, 22: 190-193.

Remington's Pharmaceutical Sciences, 17th ed., Mack Publishing Company, Easton, Pa., 1985, p. 1418.

Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.

Schlegel et al., "MERTK receptor tyrosine kinase is a therapeutic target in melanoma," The Journal of Clinical Investigation, May 2013, 123(5): 2257-2267.

Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.

(56) References Cited

OTHER PUBLICATIONS

Suarez et al., "Inhibitors of the TAM subfamily of tyrosine kinsases: Synthesis and biological evaluation," European Journal of Medicinal Chemistry, 2013, 61: 2-25.
Tai et al., "Axl promotes cell invasion by inducing MMP-9 activity through activation of NF-kappaB and Brg-1," Oncogene, Jul. 2008, 27(29): 4044-55.
Traore et al., "New aminopyrimidine derivatives as inhibitors of the TAM family," European Journal of Medicinal Chemistry, 2013, 70: 789-801.
Waizeneggar et al., "Role of Growth arrest-specific gene 6-Mer axis in multiple myeloma," Leukemia, 2015, 29: 696-704.
Wang et al., "Mer receptor tyrosine kinase promotes invasion and survival in glioblastoma multiforme," Oncogene, Feb. 2013, 32(7): 872-82.
Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Zhang et al., "Activation of the AXL kinase causes resistance to EGFR-targeted therapy in lung cancer," Nat. Genet., 2012, 44(8): 852-60.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.
Zhang et al., "UNC20205, a Potent and Orally Bioavailable MER/FLT3 Dual Inhibitor," Journal of Medicinal Chemistry, 2014, 57: 7031-7041.
International Search Report and Written Opinion in International Application No. PCT/US2016/046574, dated Oct. 21, 2016, 14 pages.
International Search Report and Written Opinion in International Application No. PCT/US2016/048716, dated Nov. 2, 2016, 12 pages.
"Urbonas et al., ""A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions,"" Synlett, 2013, 24(11):1383-1386".
Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.
Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk, 1975, 137-41 (English abstract only).
Borovik et al., "Synthesis of 2-substituted pyrimido[4,5-b]indoles and N-phenyl-2,2-diethoxy-3-arylideneindolines," v sb., Khimiya i Farmakol. Indol'n. Soedinenii, 1975, 50 (with English abstract).
Chung et al., "Synthesis of certain [6:5:6] linear tricyclic nucleosides as potential antitumor agents," Journal of Medicinal Chemistry, Nov. 1980, 23(11): 1158-66.
Dodonova et al., "Synthesis of 4-aryl-, 2, 4-diaryl- and 2, 4, 7-triarylpyrrolo [2, 3-d] pyrimidines by a combination of the Suzuki cross-coupling and N-arylation reactions," Tetrahedron, 2012, 68(1):329-339.
Ghosh, "Synthesis of 4-oxazolinephenylboronic acid and heterobiaryl oxazolines via a Suzuki reaction," Journal of Chemical Research, Apr. 2009, 4:205-207.
Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.
Klimke and Ludemann, "Further evidence for a S-syn correlation in the purine ($\beta$) ribosides: the solution conformation of two tricyclic analogs of adenosine and guanosine," Journal of Biosciences, 1979, 34C(9-10): 653-7.
Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.
Liu et al., "UNC1062, a new and potent Mer inhibitor," European Journal of Medicinal Chemistry, 2013, 65: 83-93.
Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.
Singer et al., "Photochromism of Diarylethene-Functionalized 7-Deazaguanosines," European Journal of Organic Chemistry, 2013, 14: 2766-2769.
Skardziute, "Optical study of the formation of pyrrolo[2,3-d]pyrimidine-based fluorescent nanoaggregates," Tetrahedron, 2013, 69(46):9566-9572.
Strassmaier and Karpen, "Novel N7- and N1-Substituted cGMP Derivatives Are Potent Activators of Cyclic Nucleotide-Gated Channels," Journal of Medicinal Chemistry, Aug. 2007, 50: 4186-4194.
Tumkevicius, "Pyrrolo [2, 3-d] pyrimidine-Core-Extended $\pi$-Systems: Synthesisof 2, 4, 7-Triarylpyrrolo [2, 3-d] pyrimidines," Synlett, 2011, 12:1705-1708.
Tumkevicius, "Synthesis and photophysical properties of oligoarylenes with a pyrrolo [2, 3-d] pyrimidine core," Tetrahedron Letters (2010), 51(30), 3902-3906.
Yamazoe et al., "Mechanism of formation and structural characterization of DNA adducts derived from peroxidative activation of benzidine," Carcinogenesis, Sep. 1988, 9(9): 1635-41.
Zhao, et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.
Zhou et al., "Synthesis and evaluation of Janus type nucleosides as potential HCV NS5B polymerase inhibitors," Bioorganic & Medicinal Chemistry Letters, Jun. 2013, 23: 3385-3388.

\* cited by examiner

FUSED BICYCLIC 1,2,4-TRIAZINE COMPOUNDS AS TAM INHIBITORS

CROSS-REFERENCE TO RELATED APPLICATIONS

This application claims priority to U.S. Provisional Patent Application No. 62/204,131 entitled "Bicyclic Fused Pyrimidine Compounds as TAM Inhibitors" filed on Aug. 12, 2015, which is hereby incorporated by reference in its entirety.

TECHNICAL FIELD

This application relates to pyrrolopyrimidine or imidazopyrimidine inhibitors of TAM kinases, which are useful in the treatment of disorders such as cancer, as well as pharmaceutical compositions related thereto.

BACKGROUND OF INVENTION

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need in the art for compounds and methods of use thereof for the modulation of TAM kinases in treatment of cancer.

SUMMARY OF INVENTION

In one aspect, the present application relates to compounds having Formula I:

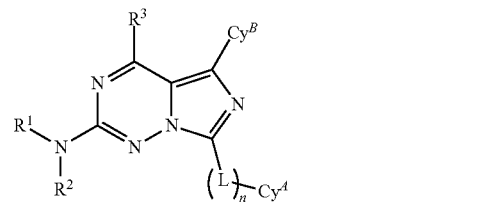

(I)

and pharmaceutically acceptable salts thereof, wherein $R^1$, $R^2$, $R^3$, L, n, $Cy^A$, and $Cy^B$ are defined infra.

The present application further provides compositions comprising a compound described herein, or a pharmaceutically acceptable salt thereof, and at least one pharmaceutically acceptable carrier.

The present application also provides methods of inhibiting TAM kinases, comprising contacting one or more TAM kinase with a compound described herein, or a pharmaceutically acceptable salt thereof.

The present invention also provides a compound described herein, or a pharmaceutically acceptable salt thereof, for use in any of the methods described herein.

The present invention further provides use of a compound described herein, or a pharmaceutically acceptable salt thereof, for manufacture of a medicament for use in any of the methods described herein.

DETAILED DESCRIPTION

The present application provides, inter alia, a compound of Formula I:

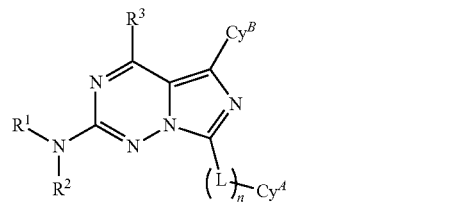

I or a pharmaceutically acceptable salt thereof, wherein:
$R^1$ is H, $C_{1-4}$ alkyl, or $C_{1-4}$ haloalkyl;
$R^2$ is $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, or 5-10 membered heteroaryl-$C_{1-4}$ alkylene; each of which is optionally substituted by 1, 2, 3, or 4 independently selected $R^{21}$ groups;

$R^3$ is H, halo, CN, OH, $C_{1-6}$ alkyl, $C_{1-4}$ haloalkyl, $C_{1-6}$ alkoxy, $C_{1-4}$ haloalkoxy, amino, $C_{1-6}$ alkylamino, or di($C_{1-6}$ alkyl)amino;

L is —$C_{1-6}$ alkylene-, —Y—, —$C_{1-6}$ alkylene-Y—, —Y—$C_{1-6}$ alkylene-, or —$C_{1-4}$ alkylene-Y—$C_{1-4}$ alkylene-; wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

Y is O, S, S(O), S(O)$_2$, C(O), C(O)NR$^f$, NR$^f$C(O), S(O)$_2$NR$^f$, NR$^f$S(O)$_2$, or NR$^f$;

each R$^f$ is independently selected from H and $C_{1-3}$ alkyl;

n is 0 or 1;

Cy$^A$ is $C_{3-7}$ cycloalkyl, phenyl, 5-6 membered heteroaryl, or 4-6 membered heterocycloalkyl, each of which is optionally substituted by 1, 2, 3, or 4 independently selected $R^A$ groups;

each $R^A$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene; wherein said $C_{1-6}$ alkyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene are each optionally substituted with 1, 2, 3, or 4 independently selected $R^{11}$ groups;

Cy$^B$ is $C_{3-10}$ cycloalkyl, 6-10 membered aryl, 5-10 membered heteroaryl, or 4-10 membered heterocycloalkyl, each of which is optionally substituted by 1, 2, 3, or 4 independently selected $R^B$ groups;

each $R^B$ is independently selected from halo, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)$_2$R$^{b2}$, S(O)NR$^{c2}$R$^{d2}$, and S(O)$_2$NR$^{c2}$R$^{d2}$; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are optionally substituted with 1, 2, 3, or 4 independently selected $R^{12}$ groups;

each $R^{11}$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, and di($C_{1-4}$ alkyl)aminosulfonyl;

each $R^{12}$ is independently selected from halo, CN, NO$_2$, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$OR$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^{13}$ groups;

each $R^{13}$ is independently selected from halo, CN, NO$_2$, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$OR$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^g$ groups;

each $R^{21}$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene; wherein said $C_{1-6}$ alkyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene are each optionally substituted with 1, 2, 3, or 4 groups independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, di($C_{1-4}$ alkyl)amino, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, and di($C_{1-4}$ alkyl)aminosulfonyl;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^{a2}$, $R^{c2}$, and $R^{d2}$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^{12}$ groups;

each $R^{b2}$ is independently selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; each of which is optionally substituted with 1, 2, 3, or 4 independently selected $R^{12}$ groups; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 independently selected $R^{12}$ groups;

each $R^{a3}$, $R^{c3}$, and $R^{d3}$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^{13}$ groups;

each $R^{b3}$ is independently selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; each of which is optionally substituted with 1, 2, 3, or 4 independently selected $R^{13}$ groups; or alternatively, any $R^{c3}$ and $R^{d3}$ attached to the same N atom, together with the N atom to which they are attached, form a 4-, 5-, 6- or 7-membered heterocycloalkyl group optionally substituted with 1, 2 or 3 independently selected $R^{13}$ groups;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; wherein said $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^g$ groups;

each $R^{b4}$ is independently selected from $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene; each of which is optionally substituted with 1, 2, 3, or 4 independently selected $R^g$ groups; or alternatively, any $R^{c4}$ and $R^{d4}$ attached to the same N atom, together with the N atom to which they are attached, form a 4-, 5-, 6- or 7-membered heterocycloalkyl group optionally substituted with 1, 2 or 3 independently selected $R^g$ groups;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is H or $C_{1-3}$ alkyl.

In some embodiments, $R^1$ is H.

In some embodiments, $R^1$ is $C_{1-3}$ alkyl.

In some embodiments, $R^2$ is $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, or 5-6 membered heteroaryl-$C_{1-4}$ alkylene; each of which is optionally substituted by 1, 2, 3, or 4 independently selected $R^{21}$ groups.

In some embodiments, $R^2$ is $C_{1-6}$ alkyl, $C_{1-4}$ haloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, or 5-6 membered heteroaryl-$C_{1-4}$ alkylene, each of which is optionally substituted by 1, 2, 3, or 4 independently selected $R^{21}$ groups.

In some embodiments, each $R^{21}$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^{21}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl.

In some embodiments, $R^2$ is $C_{1-6}$ alkyl or 6-10 membered aryl-$C_{1-4}$ alkylene.

In some embodiments, $R^2$ is n-butyl or phenylpropyl.

In some embodiments, $R^2$ is phenyl optionally substituted by 1, 2, 3, or 4 independently selected $R^{21}$ groups.

In some embodiments, $R^2$ is 5-6 membered heteroaryl optionally substituted by 1, 2, 3, or 4 independently selected $R^{21}$ groups.

In some embodiments, $R^2$ is 4-6 membered heterocycloalkyl optionally substituted by 1, 2, 3, or 4 independently selected $R^{21}$ groups.

In some embodiments, $R^3$ is H, halo, CN, OH, $C_{1-3}$ alkyl, $C_{1-3}$ haloalkyl, $C_{1-3}$ alkoxy, amino, $C_{1-3}$ alkylamino, or di($C_{1-3}$ alkyl)amino.

In some embodiments, $R^3$ is H, F, Cl, methyl, ethyl, or $CF_3$.

In some embodiments, $R^3$ is H.

In some embodiments, n is 1.

In some embodiments, L is —$C_{1-6}$ alkylene-, —Y—, —$C_{1-6}$ alkylene-Y—, or —Y—$C_{1-6}$ alkylene-.

In some embodiments, L is —$C_{1-6}$ alkylene-.

In some embodiments, L is —$CH_2$—.

In some embodiments, n is 1; and L is —$C_{1-6}$ alkylene-, —Y—, —$C_{1-6}$ alkylene-Y—, or —Y—$C_{1-6}$ alkylene-.

In some embodiments, n is 1; and L is —$C_{1-6}$ alkylene-.

In some embodiments, n is 1; and L is —$CH_2$—.

In some embodiments, n is 0.

In some embodiments, $Cy^A$ is $C_{3-7}$ cycloalkyl or 4-6 membered heterocycloalkyl, each of which is optionally substituted with 1, 2, 3, or 4 independently selected $R^A$ groups.

In some embodiments, $Cy^A$ is $C_{3-7}$ cycloalkyl optionally substituted by 1, 2, 3, or 4 $R^A$ groups.

In some embodiments, each $R^A$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, 4-6 membered heterocycloalkyl-$C_{1-3}$-alkylene, phenyl-$C_{1-3}$ alkylene, 5-6 membered heteroaryl-$C_{1-3}$ alkylene; wherein said $C_{1-6}$ alkyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, 4-6 membered heterocycloalkyl-$C_{1-3}$-alkylene, phenyl-$C_{1-3}$ alkylene, 5-6 membered heteroaryl-$C_{1-3}$ alkylene are optionally substituted with 1, 2, or 3 independently selected $R^{11}$ groups.

In some embodiments, each $R^{11}$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, and di($C_{1-4}$ alkyl)amino.

In some embodiments, each $R^A$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^A$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl.

In some embodiments, each $R^A$ is independently OH, $C_{1-6}$ alkoxy, amino, $C_{1-6}$ alkylamino, or di($C_{1-6}$ alkyl)amino.

In some embodiments, $Cy^A$ is $C_{3-7}$ cycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, $Cy^A$ is 4-6 membered heterocycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 1; L is —$C_{1-6}$ alkylene-; and $Cy^A$ is $C_{3-7}$ cycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 1; and L is —$CH_2$—; and $Cy^A$ is $C_{3-7}$ cycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 0; and $Cy^A$ is $C_{3-7}$ cycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 1; L is —$C_{1-6}$ alkylene-; and $Cy^A$ is 4-6 membered heterocycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 1; and L is —$CH_2$—; and $Cy^A$ is 4-6 membered heterocycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, n is 0; and $Cy^A$ is 4-6 membered heterocycloalkyl optionally substituted by 1 or 2 groups independently selected from OH, $C_{1-6}$ alkoxy, amino, $C_{1-6}$ alkylamino, and di($C_{1-6}$ alkyl)amino.

In some embodiments, $Cy^A$ is $C_{3-7}$ cycloalkyl optionally substituted by OH and $NH_2$.

In some embodiments, $Cy^A$ is 4-6 membered heterocycloalkyl optionally substituted by OH and $NH_2$.

In some embodiments, n is 1; L is —$C_{1-6}$ alkylene-; and $Cy^A$ is $C_{3-7}$ cycloalkyl optionally substituted by OH and $NH_2$.

In some embodiments, n is 1; and L is —$CH_2$—; and $Cy^A$ is $C_{3-7}$ cycloalkyl optionally substituted by OH and $NH_2$.

In some embodiments, n is 1; L is —$C_{1-6}$ alkylene-; and $Cy^A$ is 4-6 membered heterocycloalkyl optionally substituted by OH and $NH_2$.

In some embodiments, n is 1; and L is —CH$_2$—; and Cy$^A$ is 4-6 membered heterocycloalkyl optionally substituted by OH and NH$_2$.

In some embodiments, n is 0; and Cy$^A$ is C$_{3-7}$ cycloalkyl optionally substituted by OH and NH$_2$.

In some embodiments, n is 0; and Cy$^A$ is 4-6 membered heterocycloalkyl optionally substituted by OH and NH$_2$.

In some embodiments, Cy$^A$ is 4-hydroxycyclohexyl or 4-aminocyclohexyl.

In some embodiments, Cy$^B$ is 6-10 membered aryl or 5-10 membered heteroaryl, each of which is optionally substituted by 1, 2, 3, or 4 independently selected R$^B$ groups.

In some embodiments, Cy$^B$ is phenyl, a pyridine ring, or an indole ring, each of which is optionally substituted by 1, 2, 3, or 4 independently selected R$^B$ groups.

In some embodiments, each R$^B$ is independently selected from halo, C$_{1-6}$ alkyl, C$_{2-4}$ alkenyl, C$_{2-4}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene, CN, NO$_2$, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)R$^{b2}$, S(O)$_2$R$^{b2}$, and S(O)$_2$NR$^{c2}$R$^{d2}$; wherein C$_{1-6}$ alkyl, C$_{2-4}$ alkenyl, C$_{2-4}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene are optionally substituted with 1, 2, 3, or 4 independently selected R$^{12}$ groups.

In some embodiments, each R$^B$ is independently selected from halo, C$_{1-6}$ alkyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-4}$ alkylene, 4-6 membered heterocycloalkyl-C$_{1-4}$ alkylene, phenyl-C$_{1-4}$ alkylene, 5-6 membered heteroaryl-C$_{1-4}$ alkylene, CN, OR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$S(O)$_2$R$^{b2}$, S(O)$_2$R$^{b2}$, and S(O)$_2$NR$^{c2}$R$^{d2}$; wherein C$_{1-6}$ alkyl, C$_{2-4}$ alkenyl, C$_{2-4}$ alkynyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-4}$ alkylene, 4-6 membered heterocycloalkyl-C$_{1-4}$ alkylene, phenyl-C$_{1-4}$ alkylene, and 5-6 membered heteroaryl-C$_{1-4}$ alkylene are optionally substituted with 1, 2, 3, or 4 independently selected R$^{12}$ groups.

In some embodiments, each R$^B$ is independently selected from halo, C$_{1-6}$ alkyl, 4-6 membered heterocycloalkyl, 4-6 membered heterocycloalkyl-C$_{1-4}$ alkylene, and NR$^{c2}$C(O)R$^{b2}$; wherein said C$_{1-6}$ alkyl, 4-6 membered heterocycloalkyl, and 4-6 membered heterocycloalkyl-C$_{1-4}$ alkylene are optionally substituted with 1, 2, 3, or 4 independently selected R$^{12}$ groups.

In some embodiments, each R$^{a2}$, R$^{c2}$, and R$^{d2}$ is independently selected from H, C$_{1-6}$ alkyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-4}$ alkylene, 4-6 membered heterocycloalkyl-C$_{1-4}$ alkylene, phenyl-C$_{1-4}$ alkylene, and 5-6 membered heteroaryl-C$_{1-4}$ alkylene; wherein said C$_{1-6}$ alkyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-4}$ alkylene, 4-6 membered heterocycloalkyl-C$_{1-4}$ alkylene, phenyl-C$_{1-4}$ alkylene, and 5-6 membered heteroaryl-C$_{1-4}$ alkylene are each optionally substituted with 1, 2, or 3 independently selected R$^{12}$ groups; and each R$^{b2}$ is independently selected from C$_{1-6}$ alkyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-4}$ alkylene, 4-6 membered heterocycloalkyl-C$_{1-4}$ alkylene, phenyl-C$_{1-4}$ alkylene, and 5-6 membered heteroaryl-C$_{1-4}$ alkylene; each of which is optionally substituted with 1, 2, or 3 independently selected R$^{12}$ groups.

In some embodiments, each R$^{a2}$, R$^{c2}$, and R$^{d2}$ is independently selected from H, C$_{1-6}$ alkyl, C$_{1-4}$ haloalkyl, C$_{3-7}$ cycloalkyl, phenyl, 5-6 membered heteroaryl, and 4-6 membered heterocycloalkyl; wherein said C$_{1-6}$ alkyl, C$_{1-4}$ haloalkyl, C$_{3-7}$ cycloalkyl, phenyl, 5-6 membered heteroaryl, and 4-6 membered heterocycloalkyl are each optionally substituted with 1, 2, or 3 independently selected R$^{12}$ groups; and each R$^{b2}$ is independently selected from C$_{1-6}$ alkyl, C$_{1-4}$ haloalkyl, C$_{3-7}$ cycloalkyl, phenyl, 5-6 membered heteroaryl, and 4-6 membered heterocycloalkyl; each of which is optionally substituted with 1, 2, or 3 independently selected R$^{12}$ groups.

In some embodiments, each R$^{12}$ is independently selected from halo, CN, NO$_2$, C$_{1-6}$ alkyl, C$_{1-4}$ haloalkyl, C$_{3-10}$ cycloalkyl, 4-10 membered heterocycloalkyl, 6-10 membered aryl, 5-10 membered heteroaryl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene, OR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)$_2$R$^{b3}$, NR$^{c3}$S(O)$_2$NR$^{c3}$R$^{d3}$, S(O)$_2$R$^{b3}$, and S(O)$_2$NR$^{c3}$R$^{d3}$; wherein said C$_{1-6}$ alkyl, C$_{1-4}$ haloalkyl, C$_{3-10}$ cycloalkyl, 4-10 membered heterocycloalkyl, 6-10 membered aryl, 5-10 membered heteroaryl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-C$_{1-4}$ alkylene are each optionally substituted with 1, 2, 3, or 4 independently selected R$^{13}$ groups.

In some embodiments, each R$^{12}$ is independently selected from halo, CN, C$_{1-6}$ alkyl, C$_{1-4}$ haloalkyl, C$_{3-7}$ cycloalkyl, 4-6 membered heterocycloalkyl, phenyl, 5-6 membered heteroaryl, OR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$S(O)$_2$R$^{b3}$, NR$^{c3}$S(O)$_2$NR$^{c3}$R$^{d3}$, S(O)$_2$R$^{b3}$, and S(O)$_2$NR$^{c3}$R$^{d3}$; wherein said C$_{1-6}$ alkyl, C$_{1-4}$ haloalkyl, C$_{3-7}$ cycloalkyl, 4-6 membered heterocycloalkyl, phenyl, and 5-6 membered heteroaryl are each optionally substituted with 1, 2, 3, or 4 independently selected R$^{13}$ groups.

In some embodiments, each R$^{12}$ is independently selected from halo, CN, C$_{1-6}$ alkyl, C$_{1-4}$ haloalkyl, OR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$ NR$^{c3}$C(O)R$^{b3}$, NR$^{c3}$C(O)OR$^{a3}$, NR$^{c3}$S(O)$_2$R$^{b3}$, NR$^{c3}$S(O)$_2$NR$^{c3}$R$^{d3}$, S(O)$_2$R$^{b3}$, and S(O)$_2$NR$^{c3}$R$^{d3}$.

In some embodiments, each R$^{12}$ is independently selected from C$_{1-6}$ alkyl, OR$^{a3}$ and NR$^{c3}$R$^{d3}$.

In some embodiments, each R$^{a3}$, R$^{c3}$, and R$^{d3}$ is independently selected from H, C$_{1-6}$ alkyl, C$_{1-4}$ haloalkyl, C$_{3-7}$ cycloalkyl, phenyl, 5-6 membered heteroaryl, and 4-6 membered heterocycloalkyl; wherein said C$_{1-6}$ alkyl, C$_{1-4}$ haloalkyl, C$_{3-7}$ cycloalkyl, phenyl, 5-6 membered heteroaryl, and 4-6 membered heterocycloalkyl are each optionally substituted with 1, 2, 3, or 4 independently selected R$^{13}$ groups; and each R$^{b3}$ is independently selected from C$_{1-6}$ alkyl, C$_{1-4}$ haloalkyl, C$_{3-7}$ cycloalkyl, phenyl, 5-6 membered heteroaryl, and 4-6 membered heterocycloalkyl; each of which is optionally substituted with 1, 2, 3, or 4 independently selected R$^{13}$ groups.

In some embodiments, each R$^{a3}$, R$^{c3}$, and R$^{d3}$ is independently selected from H, C$_{1-6}$ alkyl, C$_{1-4}$ haloalkyl, C$_{3-7}$ cycloalkyl, phenyl, 5-6 membered heteroaryl, and 4-6 membered heterocycloalkyl; and each $R^{b3}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl.

In some embodiments, each $R^{a3}$ is independently H or $C_{1-6}$ alkyl; each $R^{b3}$ is independently $C_{1-6}$ alkyl; and each $R^{c3}$ and $R^{d3}$ is independently selected from H, $C_{1-6}$ alkyl, and $C_{3-6}$ cycloalkyl.

In some embodiments, each $R^{13}$ is independently selected from halo, CN, OH, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^B$ is independently selected from F, —$CH_2$-(piperazinyl), —$CH_2$-(4-methylpiperazinyl), —$CH_2$-(morpholin-4-yl), —$CH_2$—$OR^{a3}$, —$CH_2$—$NR^{c3}R^{d3}$, and $NR^{c2}C(O)R^{b2}$; each $R^{c2}$ is H or $C_{1-6}$ alkyl; each $R^{b2}$ is $C_{1-6}$ alkyl; each $R^{a3}$ is H or $C_{1-6}$ alkyl; and each $R^{c3}$ and $R^{d3}$ is independently selected from H, $C_{1-6}$ alkyl, and $C_{3-6}$ cycloalkyl.

In some embodiments:

$R^1$ is H or $C_{1-3}$ alkyl;

$R^2$ is $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, or 5-6 membered heteroaryl-$C_{1-4}$ alkylene; each of which is optionally substituted by 1, 2, 3, or 4 independently selected $R^{21}$ groups;

$R^3$ is H, halo, CN, OH, $C_{1-3}$ alkyl, $C_{1-3}$ haloalkyl, $C_{1-3}$ alkoxy, amino, $C_{1-3}$ alkylamino, or di($C_{1-3}$ alkyl)amino;

n is 0 or 1;

L is —$C_{1-6}$ alkylene-, —Y—, —$C_{1-6}$ alkylene-Y—, or —Y—$C_{1-6}$ alkylene-;

$Cy^A$ is $C_{3-7}$ cycloalkyl or 4-6 membered heterocycloalkyl, each of which is optionally substituted with 1, 2, 3, or 4 independently selected $R^A$ groups;

each $R^A$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, 4-6 membered heterocycloalkyl-$C_{1-3}$-alkylene, phenyl-$C_{1-3}$ alkylene, 5-6 membered heteroaryl-$C_{1-3}$ alkylene; wherein said $C_{1-6}$ alkyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, 4-6 membered heterocycloalkyl-$C_{1-3}$-alkylene, phenyl-$C_{1-3}$ alkylene, 5-6 membered heteroaryl-$C_{1-3}$ alkylene are optionally substituted with 1, 2, or 3 independently selected $R^{11}$ groups;

$Cy^B$ is 6-10 membered aryl or 5-10 membered heteroaryl, each of which is optionally substituted by 1, 2, 3, or 4 independently selected $R^B$ groups;

each $R^B$ is independently selected from halo, $C_{1-6}$ alkyl, $C_{2-4}$ alkenyl, $C_{2-4}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)R^{b2}$, $S(O)_2R^{b2}$, and $S(O)_2NR^{c2}R^{d2}$; wherein $C_{1-6}$ alkyl, $C_{2-4}$ alkenyl, $C_{2-4}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are optionally substituted with 1, 2, 3, or 4 independently selected $R^{12}$ groups;

each $R^{11}$ is independently selected from OH, CN, halo, $C_{1-4}$ alkyl, $C_{1-3}$ haloalkyl, $C_{1-4}$ alkoxy, $C_{1-3}$ haloalkoxy, cyano-$C_{1-3}$ alkyl, HO—$C_{1-3}$ alkyl, amino, $C_{1-4}$ alkylamino, and di($C_{1-4}$ alkyl)amino;

each $R^{12}$ is independently selected from halo, CN, $NO_2$, $C_{1-6}$ alkyl, $C_{1-4}$ haloalkyl, $C_{3-10}$ cycloalkyl, 4-10 membered heterocycloalkyl, 6-10 membered aryl, 5-10 membered heteroaryl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{1-4}$ haloalkyl, $C_{3-10}$ cycloalkyl, 4-10 membered heterocycloalkyl, 6-10 membered aryl, 5-10 membered heteroaryl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^{13}$ groups;

each $R^{13}$ is independently selected from halo, CN, OH, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino each $R^{21}$ independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino each of $R^{a2}$, $R^{c2}$, and $R^{d2}$ is independently selected from H, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; wherein said $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl- $C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene are each optionally substituted with 1, 2, or 3 independently selected $R^{12}$ groups;

each $R^{b2}$ is independently selected from $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; each of which is optionally substituted with 1, 2, or 3 independently selected $R^{12}$ groups;

each $R^{a3}$, $R^{c3}$, and $R^{d3}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl; wherein said $C_{1-6}$ alkyl, $C_{1-4}$ haloalkyl, $C_{3-7}$ cycloalkyl, phenyl, 5-6 membered heteroaryl, and 4-6 membered heterocycloalkyl are each optionally substituted with 1, 2, or 3 independently selected $R^{13}$ groups; and each $R^{b3}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl; each of which is optionally substituted with 1, 2, or 3 independently selected $R^{13}$ groups.

In some embodiments:

$R^1$ is H or $C_{1-3}$ alkyl;

$R^2$ is $C_{1-6}$ alkyl, $C_{1-4}$ haloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, or 5-6 membered heteroaryl-$C_{1-4}$ alkylene; each of which is optionally substituted by 1, 2, 3, or 4 independently selected $R^{21}$ groups;

$R^3$ is H, F, Cl, methyl, ethyl, or $CF_3$;

n is 0 or 1;

L is —$C_{1-6}$ alkylene-;

$Cy^A$ is $C_{3-7}$ cycloalkyl or 4-6 membered heterocycloalkyl, each of which is optionally substituted with 1, 2, 3, or 4 independently selected $R^A$ groups;

each $R^A$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$Cy^B$ is 6-10 membered aryl or 5-10 membered heteroaryl, each of which is optionally substituted by 1, 2, 3, or 4 independently selected $R^B$ groups;

each $R^B$ is independently selected from halo, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene, CN, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}C(O)R^{b2}$, $NR^{c2}S(O)_2R^{b2}$, $S(O)_2R^{b2}$, and $S(O)_2NR^{c2}R^{d2}$; wherein $C_{1-6}$ alkyl, $C_{2-4}$ alkenyl, $C_{2-4}$ alkynyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene are optionally substituted with 1, 2, 3, or 4 independently selected $R^{12}$ groups;

each $R^{12}$ is independently selected from halo, CN, $C_{1-6}$ alkyl, $C_{1-4}$ haloalkyl, $C_{3-7}$ cycloalkyl, 4-6 membered heterocycloalkyl, phenyl, 5-6 membered heteroaryl, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{1-4}$ haloalkyl, $C_{3-7}$ cycloalkyl, 4-6 membered heterocycloalkyl, phenyl, and 5-6 membered heteroaryl are each optionally substituted with 1, 2, 3, or 4 independently selected $R^{13}$ groups;

each $R^{13}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl;

each $R^{21}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl;

each of $R^{a2}$, $R^{c2}$, and $R^{d2}$ is independently selected from H, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; wherein said $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene are each optionally substituted with 1, 2, or 3 independently selected $R^{12}$ groups;

each $R^{b2}$ is independently selected from $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; each of which is optionally substituted with 1, 2, or 3 independently selected $R^{12}$ groups;

each $R^{a3}$, $R^{c3}$, and $R^{d3}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl; wherein said $C_{1-6}$ alkyl, $C_{1-4}$ haloalkyl, $C_{3-7}$ cycloalkyl, phenyl, 5-6 membered heteroaryl, and 4-6 membered heterocycloalkyl are each optionally substituted with 1, 2, or 3 independently selected $R^{13}$ groups; and each $R^{b3}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl; each of which is optionally substituted with 1, 2, or 3 independently selected $R^{13}$ groups.

In some embodiments:

$R^1$ is H;

$R^2$ is $C_{1-6}$ alkyl, $C_{1-4}$ haloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, or 5-6 membered heteroaryl-$C_{1-4}$ alkylene;

$R^3$ is H;

n is 0 or 1;

L is —$C_{1-6}$ alkylene-;

$Cy^A$ is $C_{3-7}$ cycloalkyl, which is optionally substituted with 1, 2, 3, or 4 independently selected $R^A$ groups;

each $R^A$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl;

$Cy^B$ is 6-10 membered aryl or 5-10 membered heteroaryl, each of which is optionally substituted by 1, 2, 3, or 4 independently selected $R^B$ groups;

each $R^B$ is independently selected from halo, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene, CN, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$; wherein $C_{1-6}$ alkyl, $C_{2-4}$ alkenyl, $C_{2-4}$ alkynyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene are optionally substituted with 1, 2, 3, or 4 independently selected $R^{12}$ groups;

each $R^{12}$ is independently selected from halo, CN, $C_{1-6}$ alkyl, $C_{1-4}$ haloalkyl, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$;

each $R^{13}$ is independently selected OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, and $C_{1-6}$ alkylaminosulfonyl;

each of $R^{a2}$, $R^{c2}$, and $R^{d2}$ is independently selected from H, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; wherein said $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene are each optionally substituted with 1, 2, or 3 independently selected $R^{12}$ groups;

each $R^{b2}$ is independently selected from $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; each of which is optionally substituted with 1, 2, or 3 independently selected $R^{12}$ groups;

each $R^{a3}$, $R^{c3}$, and $R^{d3}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl; wherein said $C_{1-6}$ alkyl, $C_{1-4}$ haloalkyl, $C_{3-7}$ cycloalkyl, phenyl, 5-6 membered heteroaryl, and 4-6 membered heterocycloalkyl are each optionally substituted with 1, 2, or 3 independently selected $R^{13}$ groups; and each $R^{b3}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl; each of which is optionally substituted with 1, 2, or 3 independently selected $R^{13}$ groups.

In some embodiments:
$R^1$ is H;
$R^2$ is $C_{1-6}$ alkyl or 6-10 membered aryl-$C_{1-4}$ alkylene;
$R^3$ is H;
n is 0 or 1;
L is —$C_{1-6}$ alkylene-;
$Cy^A$ is $C_{3-7}$ cycloalkyl, each of which is optionally substituted with 1, 2, 3, or 4 independently selected $R^A$ groups;

each $R^A$ is independently OH, $C_{1-6}$ alkoxy, amino, $C_{1-6}$ alkylamino, or di($C_{1-6}$ alkyl)amino;

$Cy^B$ is 6-10 membered aryl or 5-10 membered heteroaryl, each of which is optionally substituted by 1, 2, 3, or 4 independently selected $R^B$ groups;

each $R^B$ is independently selected from halo, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene, CN, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$; wherein $C_{1-6}$ alkyl, $C_{2-4}$ alkenyl, $C_{2-4}$ alkynyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, 5-6 membered heteroaryl-$C_{1-4}$ alkylene are optionally substituted with 1, 2, 3, or 4 independently selected $R^{12}$ groups;

each $R^{12}$ is independently selected from $C_{1-6}$ alkyl, $OR^{a3}$ and $NR^{c3}R^{d3}$;

each of $R^{a2}$, $R^{c2}$, and $R^{d2}$ is independently selected from H, $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; wherein said $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene are each optionally substituted with 1, 2, or 3 independently selected $R^{12}$ groups;

each $R^{b2}$ is independently selected from $C_{1-6}$ alkyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-4}$ alkylene, 4-6 membered heterocycloalkyl-$C_{1-4}$ alkylene, phenyl-$C_{1-4}$ alkylene, and 5-6 membered heteroaryl-$C_{1-4}$ alkylene; each of which is optionally substituted with 1, 2, or 3 independently selected $R^{12}$ groups; and each $R^{a3}$, $R^{c3}$, and $R^{d3}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl.

In some embodiments:
$R^1$ is H;
$R^2$ is $C_{1-6}$ alkyl or 6-10 membered aryl-$C_{1-4}$ alkylene;
$R^3$ is H;
n is 0 or 1;
L is —$C_{1-6}$ alkylene-;
$Cy^A$ is $C_{3-7}$ cycloalkyl optionally substituted by 1, 2, 3, or 4 $R^A$ groups;

each $R^A$ is OH, $C_{1-6}$ alkoxy, amino, $C_{1-6}$ alkylamino, or di($C_{1-6}$ alkyl)amino;

$Cy^B$ is 6-10 membered aryl or 5-10 membered heteroaryl, each of which is optionally substituted by 1, 2, 3, or 4 independently selected $R^B$ groups;

each $R^B$ is independently selected from halo, $C_{1-6}$ alkyl, 4-10 membered heterocycloalkyl, 4-10 membered heterocycloalkyl-$C_{1-4}$ alkylene, and $NR^{c2}C(O)R^{b2}$; wherein said $C_{1-6}$ alkyl, 4-10 membered heterocycloalkyl, and 4-10 membered heterocycloalkyl-C$_{1-4}$ alkylene are optionally substituted with 1, 2, 3, or 4 independently selected R$^{12}$ groups;

each R$^{c2}$ is independently H or C$_{1-6}$ alkyl;
each R$^{b2}$ is independently C$_{1-6}$ alkyl;
each R$^{12}$ is independently selected from C$_{1-6}$ alkyl, OR$^{a3}$, and NR$^{c3}$R$^{d3}$;
each R$^{a3}$ is independently H or C$_{1-6}$ alkyl; and
each R$^{c3}$ and R$^{d3}$ is independently selected from H, C$_{1-6}$ alkyl, and C$_{3-6}$ cycloalkyl.

In some embodiments:
R$^1$ is H;
R$^2$ is n-butyl or phenylpropyl;
R$^3$ is H;
n is 0 or 1;
L is —CH$_2$—;
Cy$^A$ is 4-hydroxycyclohexyl or 4-aminocyclohexyl;
Cy$^B$ is phenyl, a pyridine ring, or an indole ring, each of which is optionally substituted by 1 or 2 independently selected R$^B$ groups;
each R$^B$ is independently selected from F, —CH$_2$-(piperazinyl), —CH$_2$-(4-methylpiperazinyl), —CH$_2$-(morpholin-4-yl), —CH$_2$—OR$^{a3}$, —CH$_2$—NR$^{c3}$R$^{d3}$, and NR$^{c2}$C(O)R$^{b2}$;
each R$^{c2}$ is independently H or C$_{1-6}$ alkyl;
each R$^{b2}$ is independently C$_{1-6}$ alkyl;
each R$^{a3}$ is independently H or C$_{1-6}$ alkyl; and
each R$^{c3}$ and R$^{d3}$ is independently selected from H, C$_{1-6}$ alkyl, and C$_{3-6}$ cycloalkyl.

In some embodiments, the compound is a compound of Formula IIa or IIb:

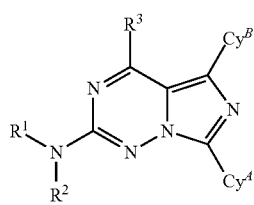

IIa

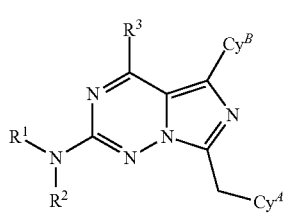

IIb or a pharmaceutically acceptable salt thereof.

In some embodiments, the compound is a compound of Formula III:

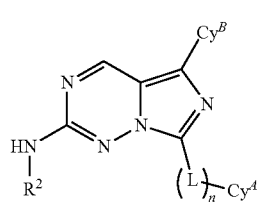

III or a pharmaceutically acceptable salt thereof.

In some embodiments, the compound is a compound of Formula IIIa or IIIb:

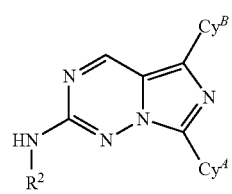

IIIa

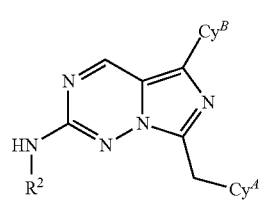

IIIb or a pharmaceutically acceptable salt thereof.

In some embodiments, the compound is a compound of Formula IV:

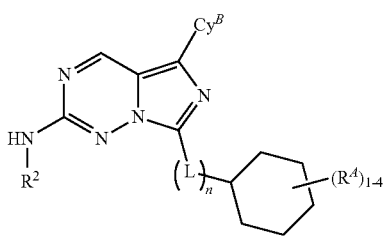

IV or a pharmaceutically acceptable salt thereof. In some embodiments, the cyclohexyl ring in Formula IV is in the cis-conformation. In some embodiments, the cyclohexyl ring in Formula IV is in the trans-conformation.

In some embodiments, the compound is a compound of Formulae IVa or IVb:

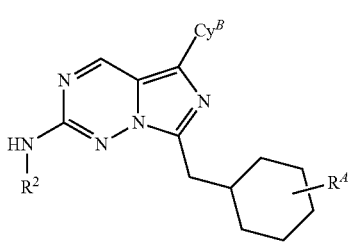

IVa

IVb

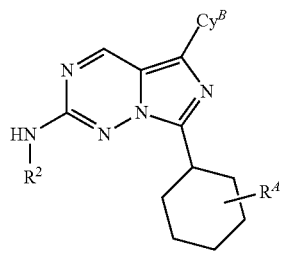

or a pharmaceutically acceptable salt thereof. In some embodiments, the cyclohexyl ring in Formula IVa is in the cis-conformation. In some embodiments, the cyclohexyl ring in Formula IVa is in the trans-conformation. In some embodiments, the cyclohexyl ring in Formula IVb is in the cis-conformation. In some embodiments, the cyclohexyl ring in Formula IVb is in the trans-conformation.

In some embodiments, the compound is a compound of Formulae Va or Vb:

Va

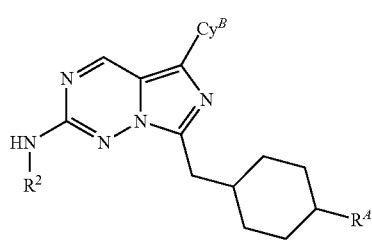

Vb

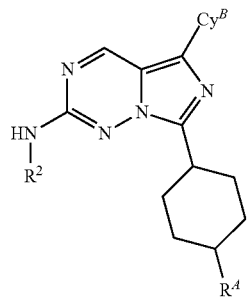

or a pharmaceutically acceptable salt thereof. In some embodiments, the cyclohexyl ring in Formula Va is in the cis-conformation. In some embodiments, the cyclohexyl ring in Formula Va is in the trans-conformation. In some embodiments, the cyclohexyl ring in Formula Vb is in the cis-conformation. In some embodiments, the cyclohexyl ring in Formula Vb is in the trans-conformation.

In some embodiments, the compound is a compound of Formulae VIa or VIb:

VIa

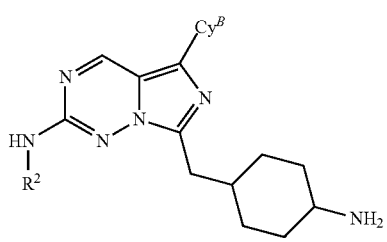

VIb

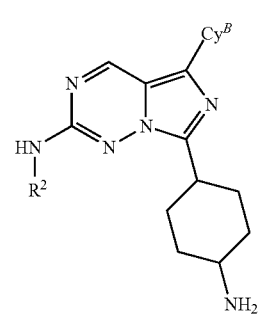

or a pharmaceutically acceptable salt thereof. In some embodiments, the cyclohexyl ring in Formula VIa is in the cis-conformation. In some embodiments, the cyclohexyl ring in Formula VIa is in the trans-conformation. In some embodiments, the cyclohexyl ring in Formula VIb is in the cis-conformation. In some embodiments, the cyclohexyl ring in Formula VIb is in the trans-conformation.

In some embodiments, the compound is a compound of Formulae VIIa or VIIb:

VIIa

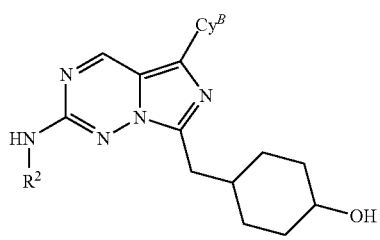

VIIb

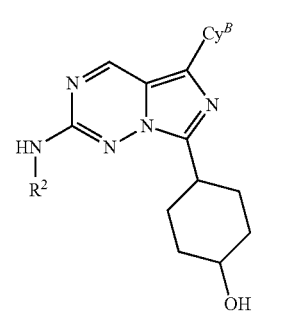

or a pharmaceutically acceptable salt thereof. In some embodiments, the cyclohexyl ring in Formula VIIa is in the cis-conformation. In some embodiments, the cyclohexyl ring in Formula VIIa is in the trans-conformation. In some embodiments, the cyclohexyl ring in Formula VIIb is in the cis-conformation. In some embodiments, the cyclohexyl ring in Formula VIIb is in the trans-conformation.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At certain places, the definitions or embodiments refer to specific rings (e.g., an azetidine ring, a pyridine ring, etc.). Unless otherwise indicated, these rings can be attached any ring member provided that the valency of the atom is not exceeded. For example, an azetidine ring may be attached at any position of the ring, whereas an azetidin-3-yl ring is attached at the 3-position.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

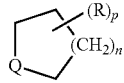

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms.

In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "HO—C1-3 alkyl" refers to a group of formula —(C1-3 alkylene)-OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, halo is F, Cl, or Br. In some embodiments, halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{3-10}$ monocyclic or bicyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O. In some embodiments, the cycloalkyl is a $C_{3-7}$ monocyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, the term "aryl," employed alone or in combination with other terms, refers to an aromatic hydrocarbon group, which may be monocyclic or polycyclic (e.g., having 2, 3 or 4 fused rings). Examples of aryl rings include, but are not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl. In some embodiments, the aryl group is phenyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In one embodiment the heteroaryl group is a 5 to 10 membered heteroaryl group. In another embodiment the heteroaryl group is a 5 to 6 membered heteroaryl group. In certain embodiments, the heteroaryl group is a monocyclic or bicyclic aromatic ring system having 5 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl. In another preferred embodiment, the heteroaryl group is a monocyclic aromatic ring system having 5 to 6 ring-forming atoms, wherein 1 to 4 ring-forming atoms are heteroatoms independently selected from N, O, and S, wherein the N and S as ring members are each optionally oxidized, the carbon ring members may be optionally replaced by carbonyl.

In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group is a morpholine ring, pyrrolidine ring, piperazine ring, piperidine ring, dihydropyran ring, tetrahydropyran ring, tetrahydropyridine, azetidine ring, or tetrahydrofuran ring. In certain embodiments, the heterocycloalkyl group is a monocyclic or bicyclic non-aromatic ring or ring system having 4 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O. In another embodiment, the heterocycloalkyl group is a monocyclic non-aromatic ring or ring system having 4 to 6 ring-forming atoms, wherein 1 to 2 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O.

As used herein, "$C_{n-m}$ cycloalkyl-$C_{o-p}$ alkylene" refers to a group of formula—alkylene-cycloalkyl, wherein the cycloalkyl group has n to m ring members and the alkylene group has o to p carbon atoms.

As used herein, "$C_{n-m}$ heterocycloalkyl-$C_{o-p}$ alkylene" refers to a group of formula—alkylene-heterocycloalkyl, wherein the heterocycloalkyl group has n to m ring members and the alkylene group has o to p carbon atoms.

As used herein, "phenyl-$C_{o-p}$ alkylene" refers to a group of formula—alkylene-phenyl, wherein the alkylene group has o to p carbon atoms.

As used herein, "$C_{n-m}$ aryl-$C_{o-p}$ alkylene" refers to a group of formula—alkylene-aryl, wherein the aryl group has n to m ring members and the alkylene group has o to p carbon atoms.

As used herein, "$C_{n-m}$ heteroaryl-$C_{o-p}$ alkylene" refers to a group of formula—alkylene-heteroaryl, wherein the heteroaryl group has n to m ring members and the alkylene group has o to p carbon atoms.

As used herein, the term "oxo" refers to an oxygen atom as a divalent substituent, forming a carbonyl group when attached to a carbon (e.g., C=O), or attached to a heteroatom forming a sulfoxide or sulfone group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as □-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H-and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TAM kinases with a compound of the invention includes the administration of a compound of the present invention to an individual or patient, such as a human, having TAM, as well as, for example, introducing a compound of the invention into a sample containing a cellular or purified preparation containing the TAM kinases.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature. Example synthetic methods for preparing compounds of the invention are provided in the Schemes 1, 2, and 3 below.

In one embodiment, a compound of Formula I can be prepared according to Scheme 1. Compound (i) can be formed by treating the anion of dithiane (i-b) with the Boc-protected Weinreb amide (i-a). Acid catalyzed treatment of (i) with thiosemicarbazide (i-c) affords compound (ii). S-alkylation and cyclization of (ii) under basic conditions yields the triazine (iii). Treatment with excess oxidant can convert the thioether of the triazine (iii) to sulfone (iv).

Nucleophilic substitution of the sulfone (iv) with an amine (xxii) affords compound (v). The Boc group in compound (v) can be removed under standard conditions (e.g. using HCl, TFA, etc.) to give an amine (vi) which is further treated with a carboxylic acid (x), and a suitable coupling reagent such as HATU or BOP to give amide (vii). Cyclization followed by dehydration of (vii) in the presence of, e.g., phosphorous oxychloride, affords compound (viii). Selective bromination of (viii) using, e.g., NBS, yields compounds (ix) which are then directly treated with a boronic acid or ester (xi) under, e.g., standard Suzuki coupling conditions, followed by removal of protecting groups to afford compounds of Formula I, wherein X=N.

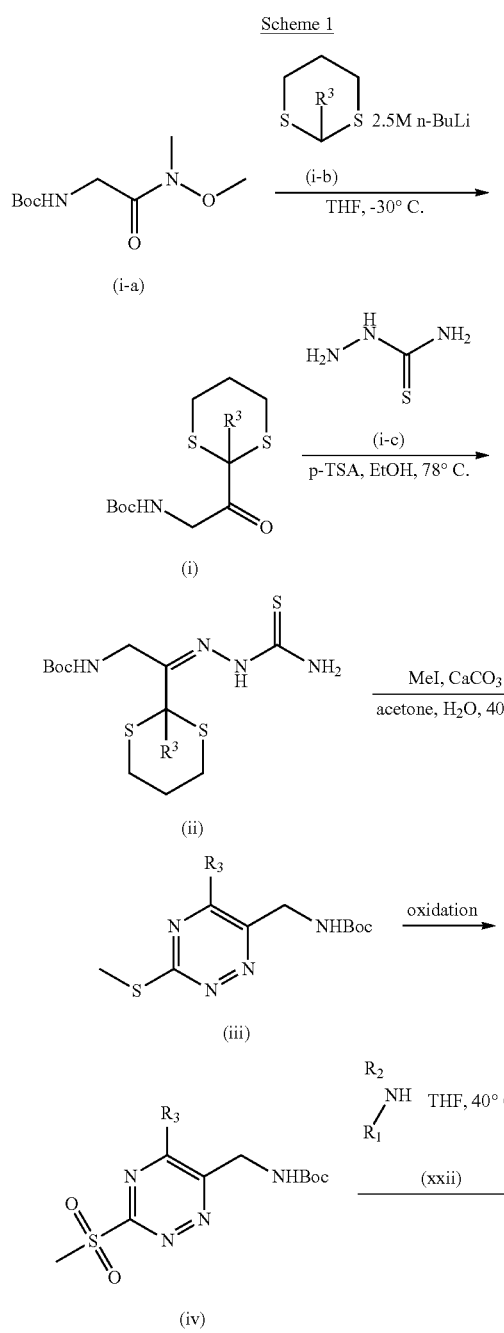

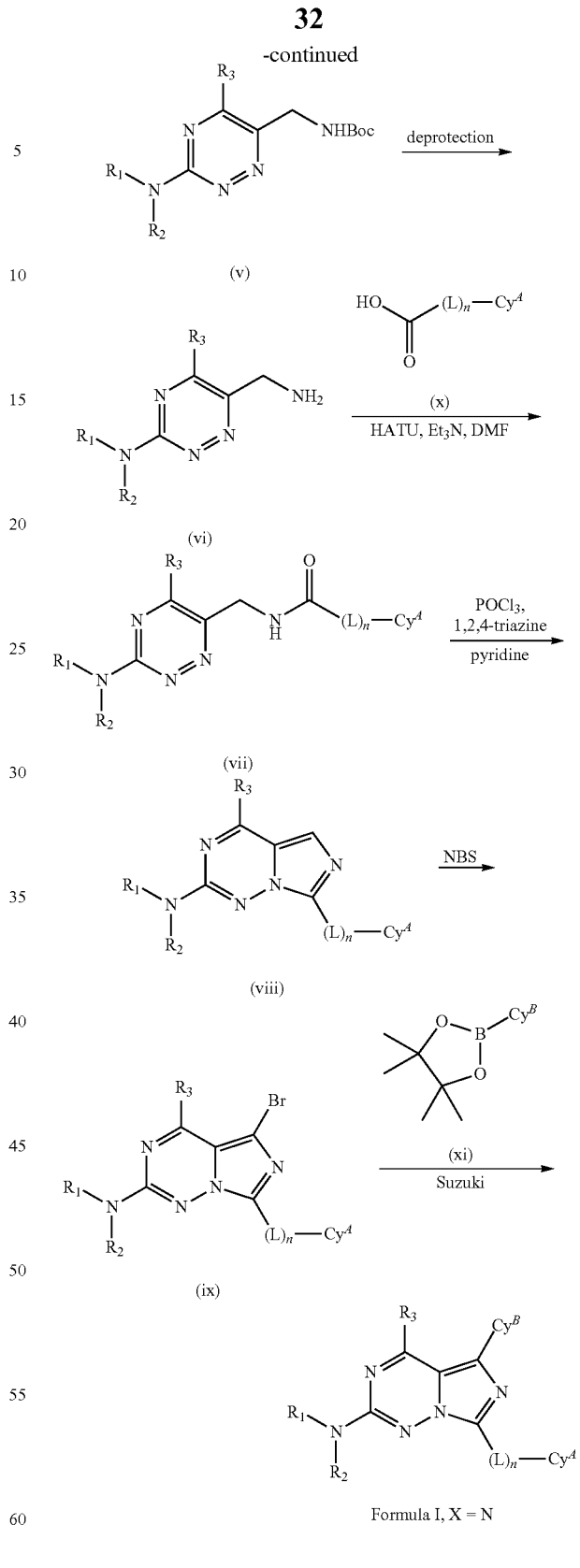

In another embodiment, a compound of Formula I can be prepared according to Scheme 2. For example, a glycine derivative (xii) can be protected to give compound (xiii). The Weinreb amide (xiv) may be formed from carboxylic acid (xiii) in a typical amide coupling reaction with N, O-dimethylhydroxylamine hydrochloride. The amide (xiv) may then react with the anion of dithiane (i-b) to give compound (xv). Acid catalyzed treatment of (xv) with thiosemicarbazide (i-c) affords compound (xvi). S-alkylation and cyclization of (xvi) under basic conditions yields the triazine (xvii). Treatment with excess oxidant can convert the thioether of the triazine (xvii) to sulfone (xviii). Nucleophilic substitution of the sulfone (xviii) with an amine (xxii) affords compound (xix). The Boc group in compound (xix) can be removed under standard conditions (e.g., using HCl, TFA, etc.) to give an amine (xx), which is further treated with a carboxylic acid (x), and a suitable coupling reagent, such as HATU or BOP, to give amide (xxi). Cyclization of amide (xxi) followed by dehydration in the presence of, e.g., phosphorous oxychloride, and final deprotections leads to compounds of Formula I, wherein X=N.

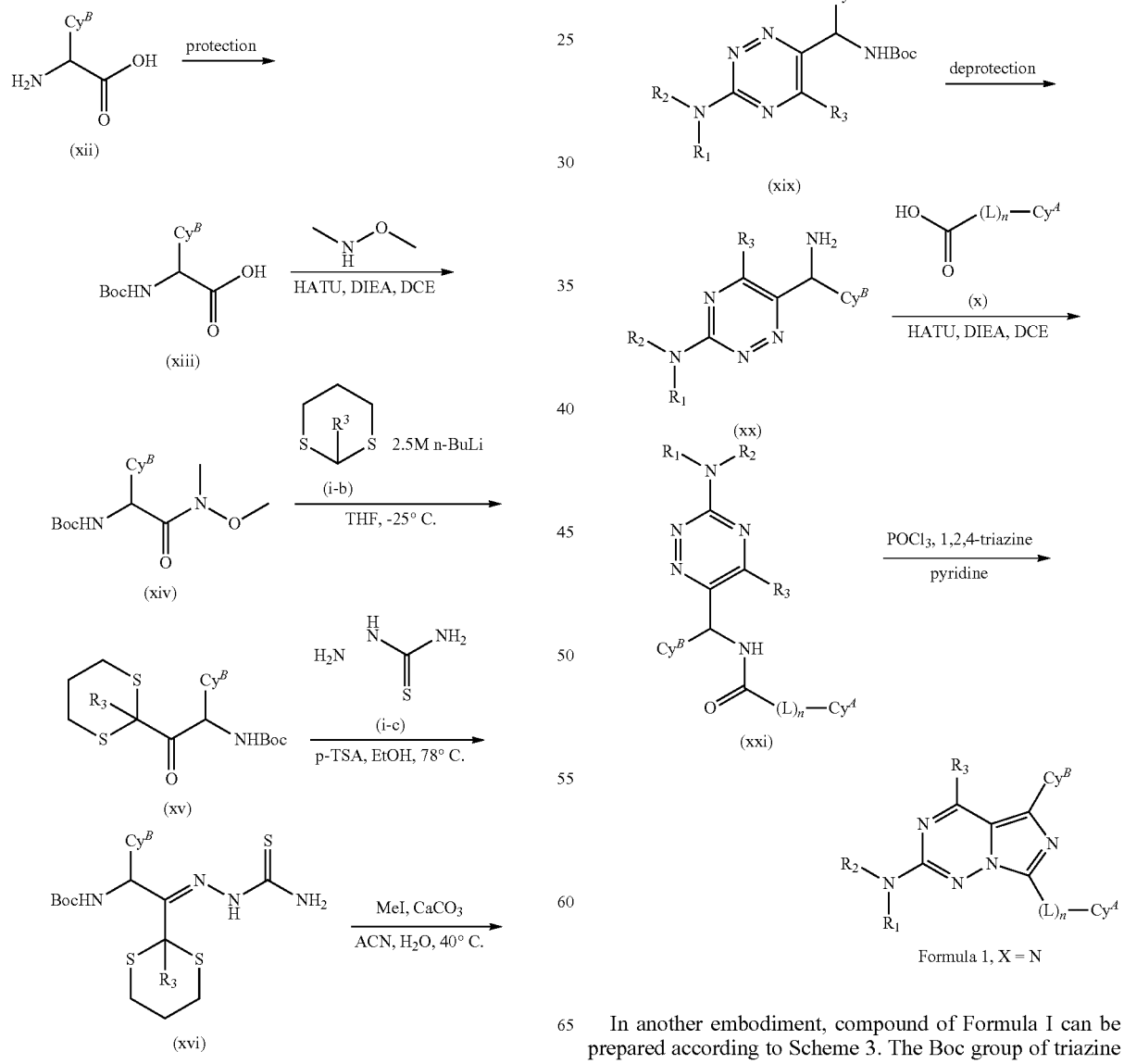

In another embodiment, compound of Formula I can be prepared according to Scheme 3. The Boc group of triazine (iii) can be removed under standard conditions (e.g., using HCl, TFA, etc.) to give an intermediate amine which is further treated with a carboxylic acid (x), and a suitable coupling reagent, such as HATU or BOP, to give amide coupling conditions with a boronic acid or ester (xi) followed by deprotection to give compounds of Formula I, wherein X=N.

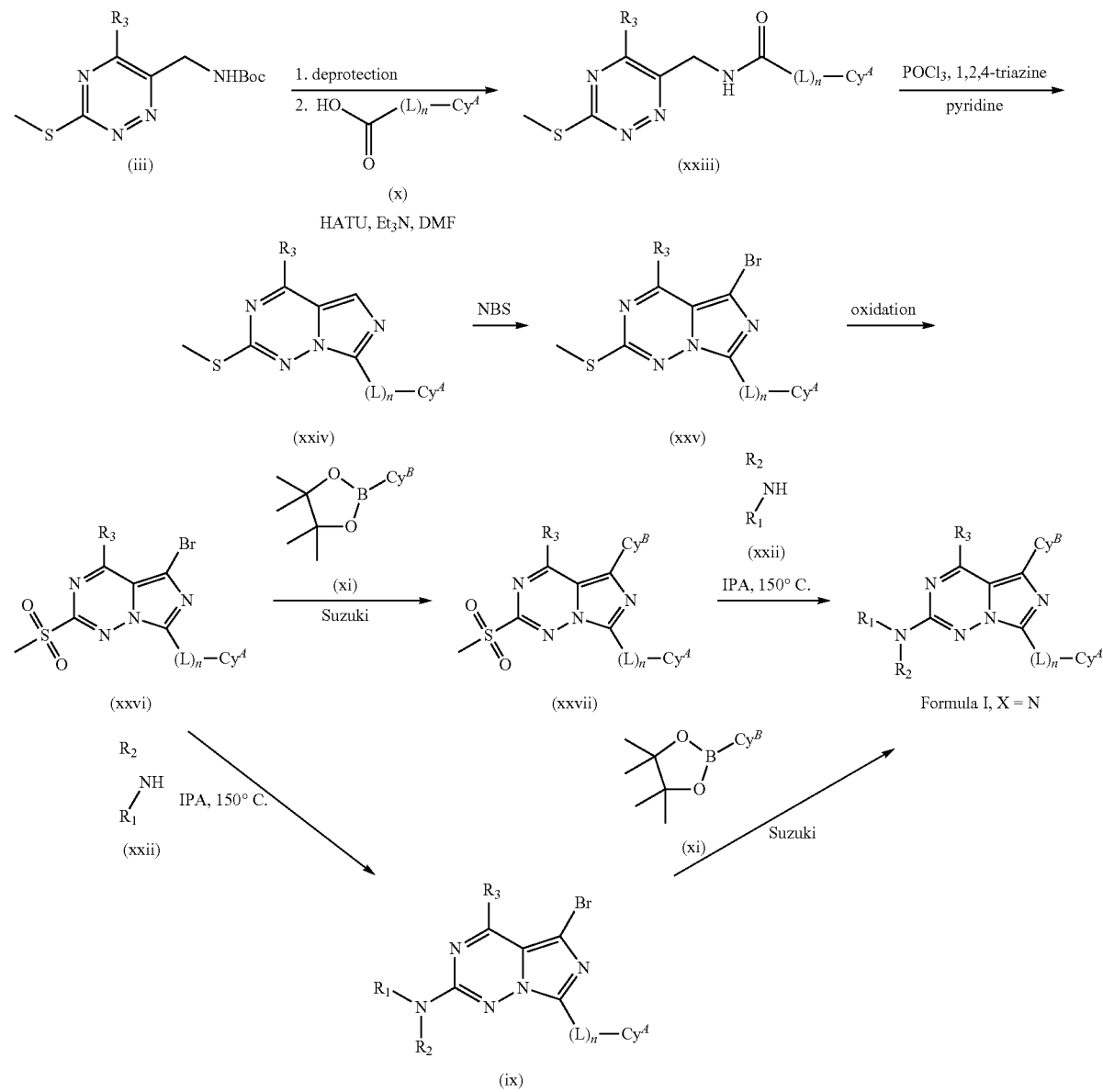

(xxiii). Cyclization of amide (xxiii) followed by dehydration in the presence of, e.g., phosphorous oxychloride, affords compound (xxiv). Selective bromination of compound (xxiv) under typical conditions yields compounds (xxv). Treatment with excess oxidant can convert the thioether of the triazine (xxv) to sulfone (xxvi). Sulfone (xxvi) may be treated with a boronic acid or ester (xi) under, e.g., standard Suzuki coupling conditions, to give (xxvii). Nucleophilic substitution of the sulfone with amines (xxii) and final deprotection affords compounds of Formula I, wherein X=N. Alternatively, introduction of the amine (xxii) onto compound (xxvi) may be performed to give compound (ix). Finally compound (ix) may be subject to, e.g., Suzuki TAM Kinases Receptor tyrosine kinases (RTKs) are cell surface proteins that transmit signals from the extracellular environment to the cell cytoplasm and nucleus to regulate cellular events such as survival, growth, proliferation, differentiation, adhesion and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity. The TAM subfamily consists of three RTKs including TYRO3, AXL and MER (Graham et al., 2014, Nature reviews Cancer 14, 769-785; and Linger et al., 2008, Oncogene 32, 3420-3431). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are over-expressed in many cancers and play important roles in tumor initiation and maintenance; therefore, TAM inhibition represents an attractive approach for targeting another class of oncogenic RTKs (Graham et al., 2014, Nature reviews Cancer 14, 769-785; and Linger et al., 2008, Oncogene 32, 3420-3431).

Axl was originally identified as a transforming gene from DNA of patients with chronic myelogenous leukemia (O'Bryan et al., 1991, Molecular and cellular biology 11, 5016-5031). GAS6 binds to Axl and induces subsequent auto-phosphorylation and activation of Axl tyrosine kinase. Axl activates several downstream signaling pathways including PI3K-Akt, Raf-MAPK, PLC-PKC (Feneyrolles et al., 2014, Molecular cancer therapeutics 13, 2141-2148; Linger et al., 2008, Oncogene 32, 3420-3431). AXL is over-expressed or amplified in a variety of malignancies including lung cancer, prostate cancer, colon cancer, breast cancer, melanoma, and renal cell carcinoma (Linger et al., 2008, Oncogene 32, 3420-3431). Over-expression of AXL is correlated with poor prognosis (Linger et al., 2008, Oncogene 32, 3420-3431). As a result, AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer biology & therapy 8, 618-626). In prostate cancer, AXL inhibition decreased cell migration, invasion, and proliferation (Tai et al., 2008, Oncogene 27, 4044-4055). In addition, AXL over-expression or amplification is a major mechanism for resistance to EGFR inhibitors by lung cancer cells, and AXL inhibition can reverse the resistance (Zhang et al., 2012, Nature genetics 44, 852-860).

Mer was originally identified as a phospho-protein from a lymphoblastoid expression library (Graham et al., 1995, Oncogene 10, 2349-2359). Both GAS6 and ProS can bind to Mer and induce the phosphorylation and activation of Mer kinase (Lew et al., 2014. eLife, 3:e03385). Like Axl, Mer activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

Tyro3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

In addition to their role as transforming oncogenes, TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

TAM kinases have been shown to function as checkpoints for immune activation in the tumor milieu. All TAM kinases are expressed in NK cells, and TAM kinases inhibit the anti-tumor activity of NK cells. LDC1267, a small molecule TAM inhibitor, activates NK cells, and blocks metastasis in tumor models with different histologies (Paolino et al., 2014, Nature 507, 508-512). In addition, MER kinase promotes the activity of tumor associated macrophages through the increased secretion of immune suppressive cytokines such as IL10 and IL4, and decreased production of immune activating cytokines such as IL12 (Cook et al., 2013, The Journal of clinical investigation 123, 3231-3242). MER inhibition has been shown to reverse this effect. As a result, MER knockout mice are resistant to PyVmT tumor formation (Cook et al., 2013, The Journal of clinical investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks after birth (Chambers et al., 1997, Immunity 7, 885-895; and Nishimura et al., 2001, Science 291, 319-322).

TAM inhibition will have not only direct activity against neoplastic cells, but also activate the anti-cancer immune response. Thus TAM inhibitors represent an attractive approach for the treatment of cancer as single agents. In addition, TAM inhibitors may be combined with other targeted therapies, chemotherapies, radiation, or immunotherapeutic agents to achieve maximal efficacy in the clinic.

Methods of Use

Compounds of the present disclosure can modulate or inhibit the activity of TAM kinases. For example, the compounds of the disclosure can be used to inhibit activity of a TAM kinase in a cell or in an individual or patient in need of inhibition of the kinases by administering an inhibiting amount of a compound of the disclosure to the cell, individual, or patient.

In some embodiments, the compounds of the disclosure are selective for the TAM kinases over one or more of other kinases. In some embodiments, the compounds of the disclosure are selective for the TAM kinases over other kinases. In some embodiments, the selectivity is 2-fold or more, 3-fold or more, 5-fold or more, 10-fold or more, 25-fold or more, 50-fold or more, or 100-fold or more.

As TAM kinases inhibitors, the compounds of the disclosure are useful in the treatment of various diseases associated with abnormal expression or activity of the TAM kinases. Compounds which inhibit TAM kinases will be useful in providing a means of preventing the growth or inducing apoptosis in tumors, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors.

In certain embodiments, the disclosure provides a method for treating a disease or disorder mediated by TAM kinases in a patient in need thereof, comprising the step of administering to said patient a compound according to the invention, or a pharmaceutically acceptable composition thereof.

For example, the compounds of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Compounds of the disclosure can also be useful in the inhibition of tumor metastasis.

In some embodiments, the present disclosure provides a method for treating hepatocellular carcinoma in a patient in need thereof, comprising the step of administering to said patient a compound of Formula (I) or a compound as disclosed herein, or a pharmaceutically acceptable salt thereof, or a composition comprising a compound of Formula (I) or a compound as disclosed herein.

In some embodiments, the present disclosure provides a method for treating Rhabdomyosarcoma, esophageal cancer, breast cancer, or cancer of a head or neck, in a patient in need thereof, comprising the step of administering to said patient a compound Formula (I) or a compound as disclosed herein, or a pharmaceutically acceptable salt thereof, or a composition comprising a compound of Formula (I) or a compound as disclosed herein.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

Combination Therapy

One or more additional pharmaceutical agents or treatment methods such as, for example, anti-viral agents, chemotherapeutics or other anti-cancer agents, immune enhancers, immunosuppressants, radiation, anti-tumor and antiviral vaccines, cytokine therapy (e.g., IL2, GM-CSF, etc.), and/or tyrosine kinase inhibitors can be used in combination with the compounds of Formula (I) or a compound as described herein for treatment of TAM-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

The TAM inhibitors of the application invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: PIM, Pim1, Pim2, Pim3, IDO, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the TAM inhibitors of the invention can be combined with inhibitors of kinases associated with the PI3K/Akt/mTOR signaling pathway, such as PI3K, including PI3Kγ, PI3Kδ, Akt (including Akt1, Akt2 and Akt3) and mTOR kinases.

The TAM inhibitors of the present application can be used in combination with one or more other BET bromodomain inhibitors such a BRD2, BRD3, BRD4 and BRDT that are useful for the treatment of diseases, such as cancer.

The TAM inhibitors of the present application can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with TAM inhibitors. These include onartumzumab, tivantnib, and INC-280. Agents against FGFRs include but not limited to AZD4547, BAY1187982, ARQ087, BGJ398, BIBF1120, TKI258, lucitanib, dovitinib, TAS-120, JNJ-42756493, and Debiol347. Agents against Trks include but not limited to LOXO-101, and RXDX-101. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with TAM inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, inhibitors of Pim kinases, and inhibitors of protein chaperones and cell cycle progression.

Agents against the PI3 kinase include but are not limited to pilaralisib, idelalisib, buparlisib and IPI-549. In some embodiments, the PI3K inhibitor is selective for PI3K alpha, PI3K beta, PI3K gamma or PI3K delta. Inhibitors of mTOR such as rapamycin, sirolimus, temsirolimus, and everolimus may be combined with TAM kinases inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, and tofacitinib), selective JAK1 inhibitors (e.g., INCB039110), IDO inhibitors (e.g., INCB024360), PI3Kδ inhibitors (e.g., INCB040093, INCB050465), sp90 (e.g., tanespimycin), cyclin dependent kinases (e.g., palbociclib), PARP (e.g., olaparib), and proteasomes (e.g., bortezomib, carfilzomib) can also be combined with compounds of the present invention. In some embodiments, the JAK inhibitor is selective for JAK1 over JAK2 and JAK3. Agents against Pim kinases include but not limited to LGH447, INCB053914, and SGI-1776.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) inhibitors.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-1, and PD-L1 or antibodies to cytokines (IL-10, TGF-β, etc.).

Other anti-cancer agents include CSF1R inhibitors (PLX3397, LY3022855, etc.) and CSF1R antibodies (IMC-CS4, RG7155, etc).

Other anti-cancer agents include BET inhibitors (INCB054329, OTX015, CPI-0610, etc.), LSD1 inhibitors (GSK2979552, INCB059872, etc), HDAC inhibitors (panobinostat, vorinostat, etc), DNA methyl transferase inhibitors (azacitidine and decitabine), and other epigenetic modulators.

Other anti-cancer agents include Bcl2 inhibitor ABT-199, and other Bcl-2 family protein inhibitors.

Other anti-cancer agents include TGF beta receptor kinase inhibitor such as LY2157299.

Other anti-cancer agents include BTK inhibitor such as ibrutinib.

Other anti-cancer agents include beta catenin pathway inhibitors, notch pathway inhibitors and hedgehog pathway inhibitors.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK In one embodiment antibody therapeutics to be used in combination with the TAM inhibitors of the current invention include PD-1 antibodies such as pembrolizumab and/or nivolumab. In one embodiment antibody therapeutics also include PD-L1 antibodies such as MPDL3280A and/or MEDI4736.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

One or more additional immune checkpoint inhibitors can be used in combination with a compound as described herein for treatment of TAM-associated diseases, disorders or conditions. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, CD96 TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518, MK-4166, INCAGN01876 or MK-1248.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

The compounds of the present application can be used in combination with a selective JAK1 inhibitor. As used herein, a "selective JAK1 inhibitor" is an inhibitor of JAK1 which is selective for JAK1 over JAK2, JAK3 and TYK2. In some embodiments, the compounds or salts are about 10-fold more selective for JAK1 over JAK2. In some embodiments, the compounds or salts are about 10-fold, about 15-fold, or about 20-fold more selective for JAK1 over JAK2 as calculated by measuring $IC_{50}$ at 1 mM ATP (e.g., see Example A).

In some embodiments, the selective JAK1 inhibitor is a compound of Table A, or a pharmaceutically acceptable salt thereof. The compounds in Table A are selective JAK1 inhibitors (selective over JAK2, JAK3, and TYK2). The ICsos obtained by the method of Assay A at 1 mM ATP as described in the US Patent Publications in Table A.

TABLE A

| # | Source | Name | Structure | JAK1 $IC_{50}$ (nM) | JAK2/JAK1 |
|---|--------|------|-----------|---------------------|-----------|
| 1 | US 2014/0121198 | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 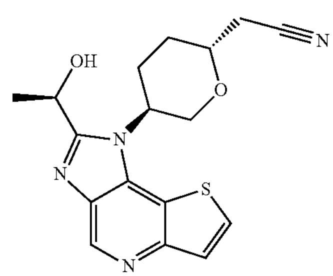 [SMILES: C[C@@H](O)c1nc2cnc3ccsc3c2n1[C@H]1CC[C@H](CC#N)OC1] | ++ | >10 |
| 2 | US 2014/0121198 | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 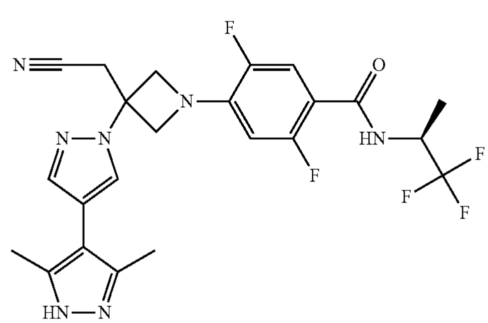 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |

TABLE A-continued

| # | Source | Name | Structure | JAK1 IC$_{50}$ (nM) | JAK2/JAK1 |
|---|---|---|---|---|---|
| 3 | US 2010/0298334 (Example 2)[a] | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 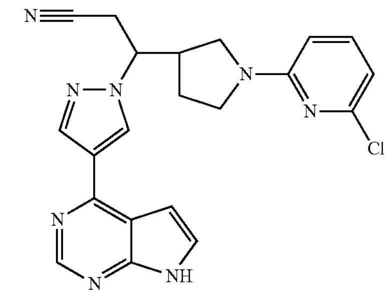 [SMILES: N#CCC(C1CCN(c2cccc(Cl)n2)C1)n1cc(-c2ncnc3[nH]ccc23)cn1] | + | >10 |
| 4 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 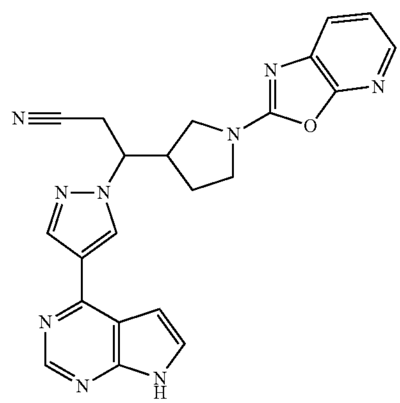 [SMILES: N#CCC(C1CCN(c2nc3cccnc3o2)C1)n1cc(-c2ncnc3[nH]ccc23)cn1] | + | >10 |
| 5 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 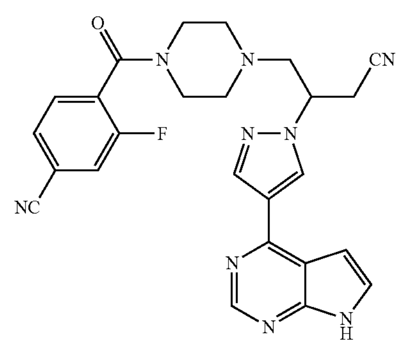 [SMILES: N#CCC(CN1CCN(C(=O)c2ccc(C#N)cc2F)CC1)n1cc(-c2ncnc3[nH]ccc23)cn1] | + | >10 |
| 6 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 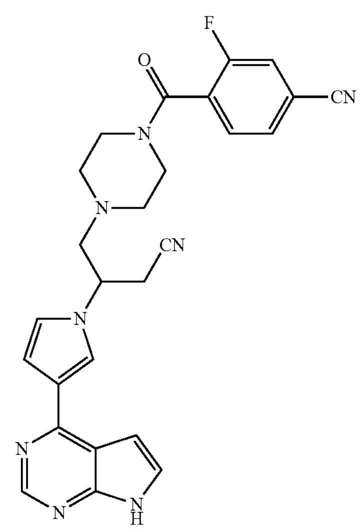 [SMILES: N#CCC(CN1CCN(C(=O)c2ccc(C#N)cc2F)CC1)n1ccc(-c2ncnc3[nH]ccc23)c1] | + | >10 |

TABLE A-continued

| # | Source | Name | Structure | JAK1 IC$_{50}$ (nM) | JAK2/JAK1 |
|---|---|---|---|---|---|
| 7 | US 2011/0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 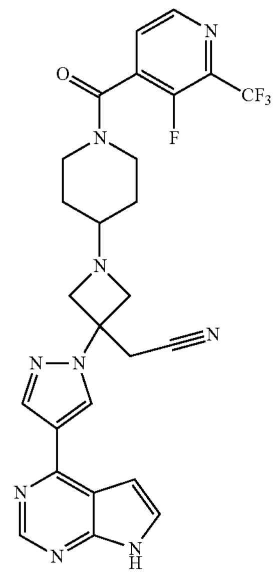 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 8 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 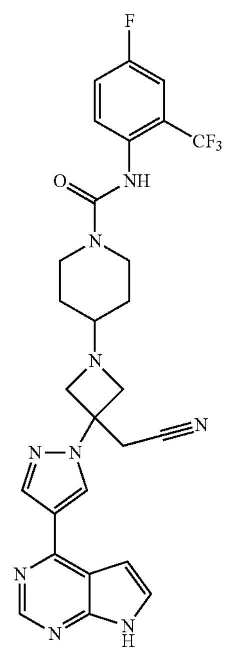 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE A-continued

| # | Source | Name | Structure | JAK1 IC$_{50}$ (nM) | JAK2/JAK1 |
|---|--------|------|-----------|---------------------|-----------|
| 9 | US 2011/0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 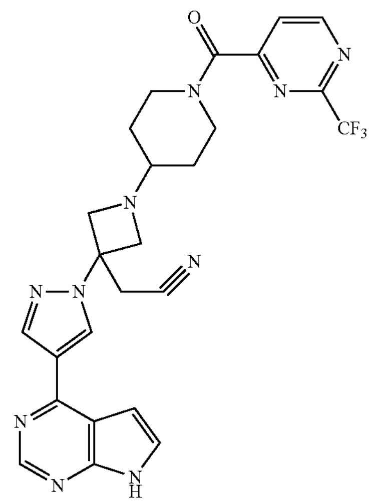 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 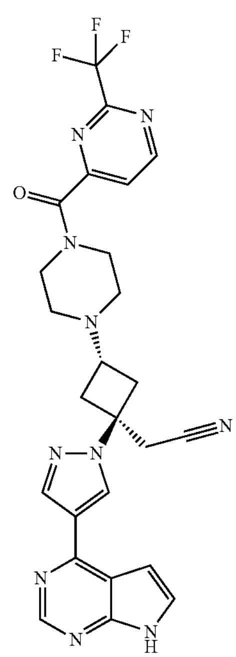 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |

TABLE A-continued

| # | Source | Name | Structure | JAK1 IC$_{50}$ (nM) | JAK2/JAK1 |
|---|--------|------|-----------|---------------------|-----------|
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 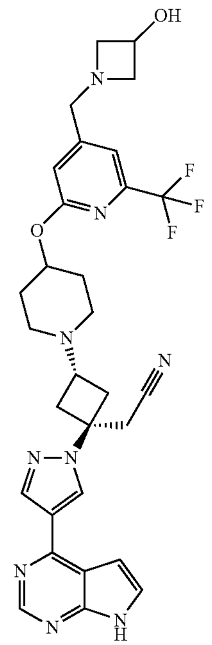 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 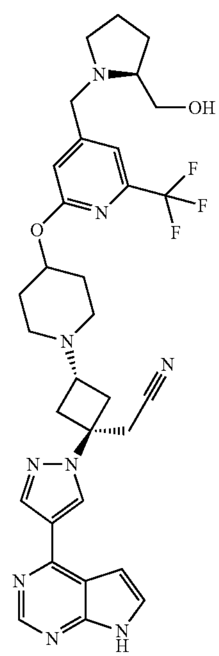 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |

TABLE A-continued

| # | Source | Name | Structure | JAK1 IC$_{50}$ (nM) | JAK2/JAK1 |
|---|---|---|---|---|---|
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl)acetonitrile | 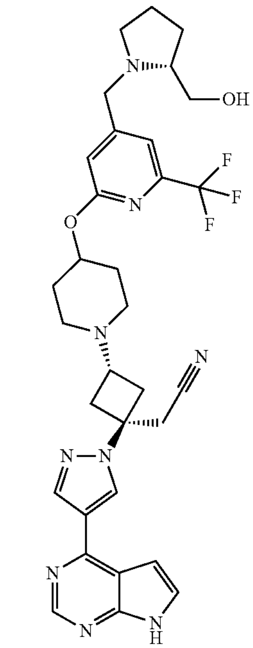 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 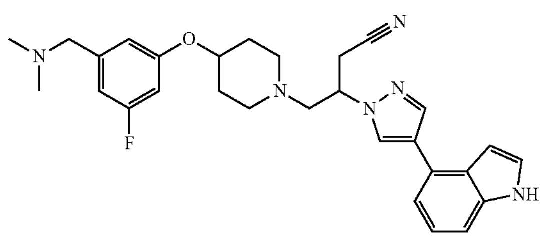 [SMILES: CN(C)Cc1cc(F)cc(OC2CCN(CC(CC#N)n3cc(-c4cccc5[nH]ccc45)cn3)CC2)c1] | + | >10 |
| 15 | US 2013/0018034 (Example 18) | 5-{3-(cyanomethyl) 3-[4-(7H-pyrrolo[2,3-d]pyrimidin-4-yl)-1H-pyrazol-1-yl]azetidin-1-yl}-N-isopropylpyrazine-2-carboxamide | 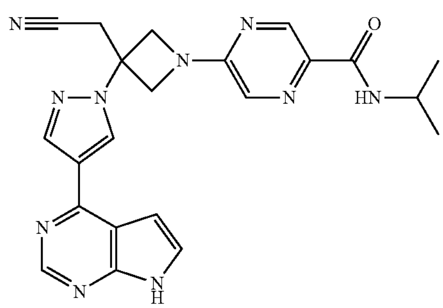 [SMILES: CC(C)NC(=O)c1cnc(N2CC(CC#N)(n3cc(-c4ncnc5[nH]ccc45)cn3)C2)cn1] | + | >10 |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 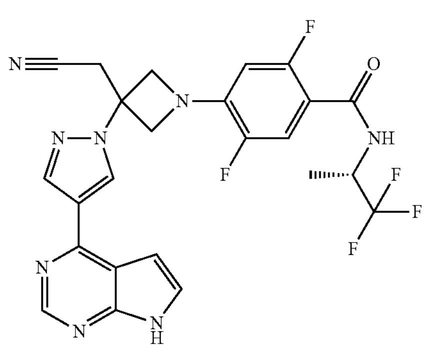 [SMILES: C[C@H](NC(=O)c1cc(F)c(N2CC(CC#N)(n3cc(-c4ncnc5[nH]ccc45)cn3)C2)cc1F)C(F)(F)F] | + | >10 |

TABLE A-continued

| # | Source | Name | Structure | JAK1 IC$_{50}$ (nM) | JAK2/JAK1 |
|---|---|---|---|---|---|
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 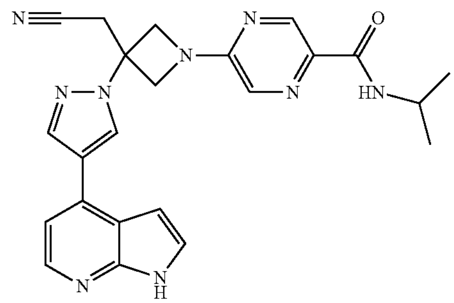 [SMILES: CC(C)NC(=O)c1cnc(N2CC(CC#N)(n3cc(-c4ccnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 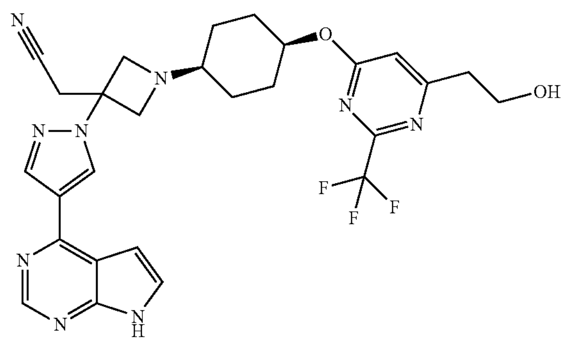 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 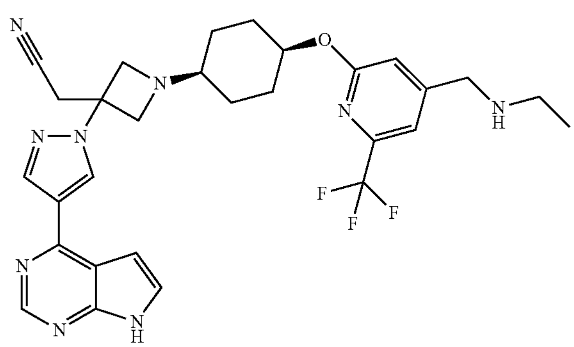 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE A-continued

| # | Source | Name | Structure | JAK1 IC$_{50}$ (nM) | JAK2/JAK1 |
|---|--------|------|-----------|---------------------|-----------|
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 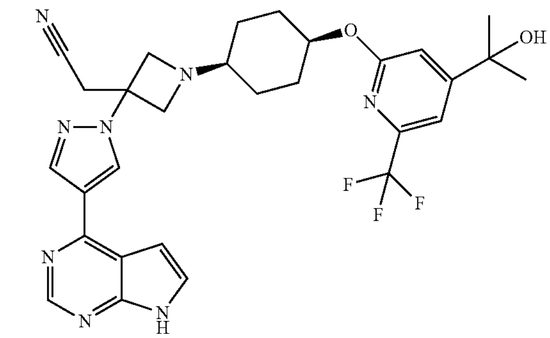 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 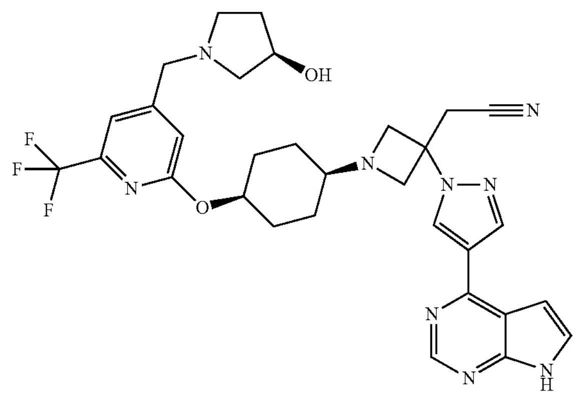 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 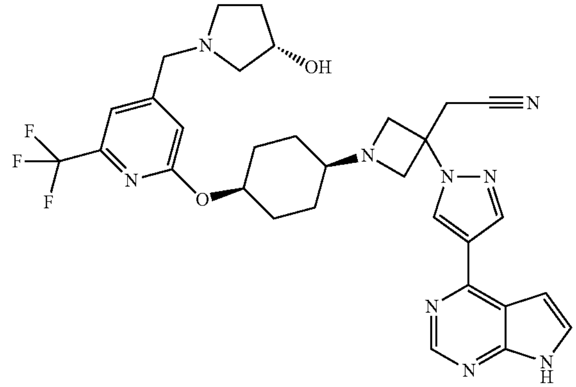 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE A-continued

| # | Source | Name | Structure | JAK1 IC$_{50}$ (nM) | JAK2/JAK1 |
|---|---|---|---|---|---|
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 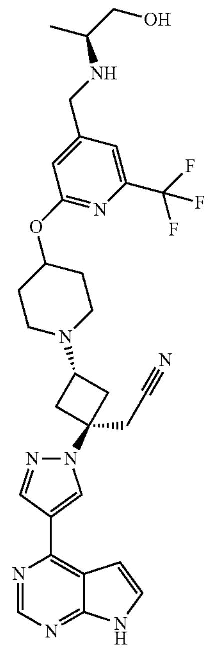 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 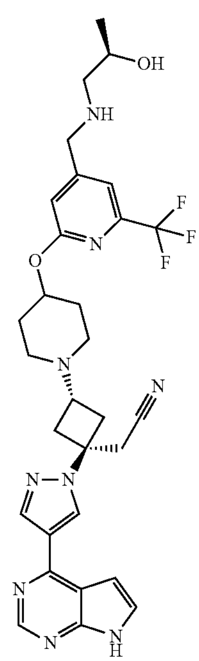 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Source | Name | Structure | JAK1 IC$_{50}$ (nM) | JAK2/JAK1 |
|---|---|---|---|---|---|
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 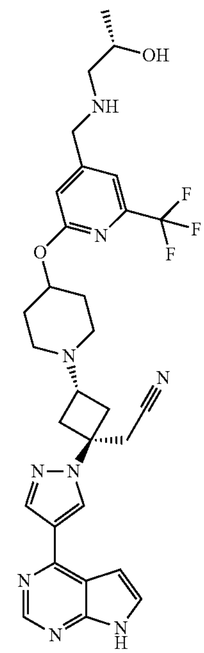 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 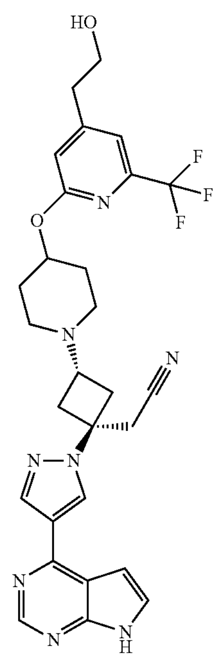 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤100 nM (see Example A for assay conditions)
+++ means ≤300 nM (see Example A for assay conditions)
[a]Data for enantiomer 1
[b]Data for enantiomer 2

The compounds of the present application can be used in combination with a PI3Kδ inhibitor. In some embodiments, the PI3Kδ inhibitor is selective. By "selective" is meant that the compound binds to or inhibits a kinase with greater affinity or potency, respectively, compared to at least one other kinase. In some embodiments, the PI3Kδ inhibitors are selective inhibitors of PI3Kδ (e.g., over PI3Kα, PI3Kβ and PI3Kγ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds described herein can be determined by cellular assays associated with particular PI3K kinase activity.

In some embodiments, the inhibitor of PI3Kδ is a compound shown in Table B. The compounds of Table B have been tested in the enzyme assays in the patent publications in Table B and shown to be inhibitors of PI3Kδ with the IC50s shown below.

TABLE B

| # | Prep. | Name | Structure | PI3Kδ IC$_{50}$ (nM) |
|---|---|---|---|---|
| 27 | US 2011/0015212 (Example 10) | 7-(1-(9H-purin-6-ylamino)ethyl)-6-(3-fluorophenyl)-3-methyl-5H-thiazolo[3,2-a]pyrimidin-5-one | 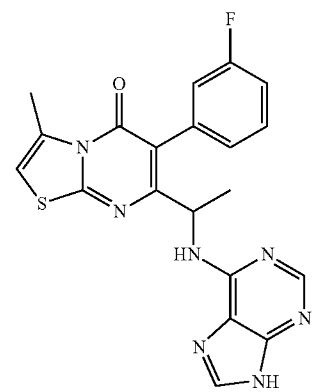 [SMILES: Cc1csc2nc(C(C)Nc3ncnc4[nH]cnc34)c(-c3cccc(F)c3)c(=O)n12] | + |
| 28 | US 2011/0015212 (Example 15) | (S)-7-(1-(9H-purin-6-ylamino)ethyl)-6-(3-fluorophenyl)-3-methyl-5H-thiazolo[3,2-a]pyrimidin-5-one | 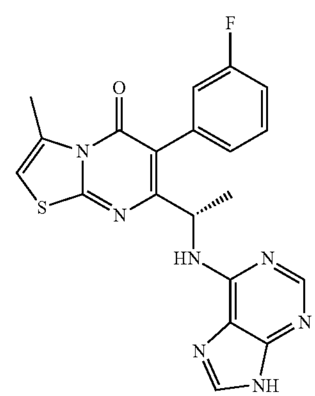 [SMILES: Cc1csc2nc([C@H](C)Nc3ncnc4[nH]cnc34)c(-c3cccc(F)c3)c(=O)n12] | + |
| 29 | US 2013/0059835 (Example 269) | 4-[1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile | 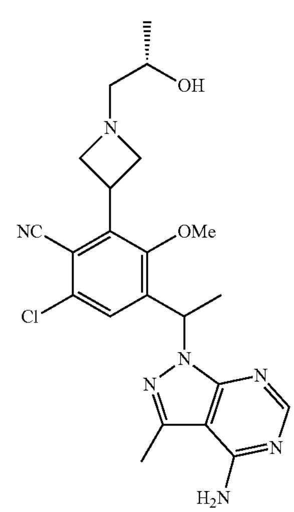 [SMILES: COc1c(C(C)n2nc(C)c3c(N)ncnc32)cc(Cl)c(C#N)c1C1CN(C[C@H](C)O)C1] | + |

TABLE B-continued

| # | Prep. | Name | Structure | PI3Kδ IC$_{50}$ (nM) |
|---|---|---|---|---|
| 30 | US 2013/0059835 (Example 268) | 4-[1-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile | 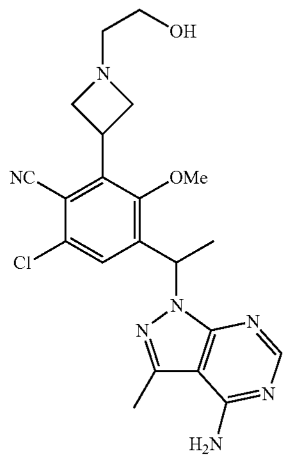 [SMILES: COc1c(C(C)n2nc(C)c3c(N)ncnc32)cc(Cl)c(C#N)c1C1CN(CCO)C1] | + |
| 31 | US 2013/0059835 (Example 314) | 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide | 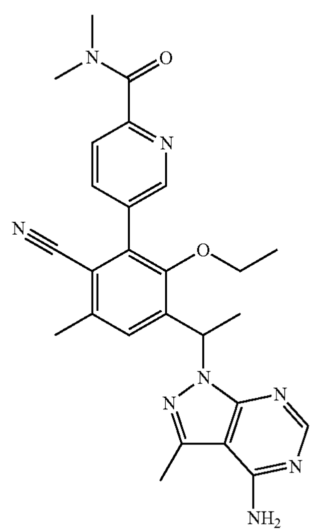 [SMILES: CCOc1c(C(C)n2nc(C)c3c(N)ncnc32)cc(C)c(C#N)c1-c1ccc(C(=O)N(C)C)nc1] | + |
| 32a, 32b, 32c, 32d | US 2013/0059835 (Example 345-348 (four diastereomers)) Compound 32a, 32b, 32c, and 32d are Examples 345, 346, 347, and 348 respectively | 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one | 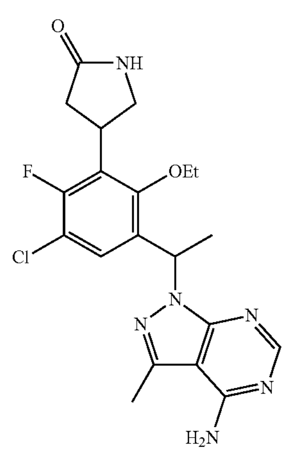 [SMILES: CCOc1c(C(C)n2nc(C)c3c(N)ncnc32)cc(Cl)c(F)c1C1CNC(=O)C1] | 32a (++), 32b (+) 32c (+) 32d (++) |

TABLE B-continued

| # | Prep. | Name | Structure | PI3Kδ IC$_{50}$ (nM) |
|---|---|---|---|---|
| 33 | US 2011/0183985 (Example 17- single enantiomer) | N-{1-[5-chloro-8-(3-fluorophenyl)cinnolin-7-yl]ethyl}-9H-purin-6-amine | 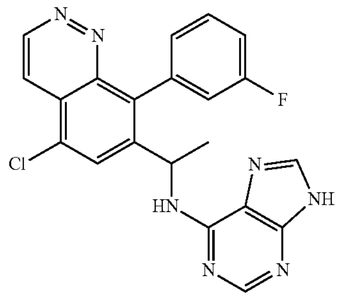 [SMILES: CC(Nc1ncnc2[nH]cnc12)c1cc(Cl)c2ccnnc2c1-c1cccc(F)c1] | + |
| 34 | US 2012/0157430 | 4-chloro-3'-fluoro-3-methyl-6-[1-(9H-purin-6-ylamino)ethyl]biphenyl-2-carbonitrile | 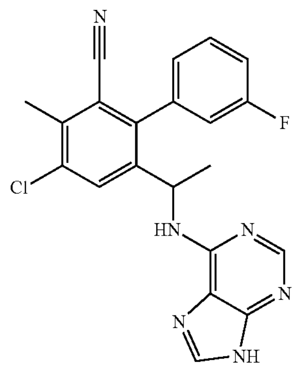 [SMILES: Cc1c(Cl)cc(C(C)Nc2ncnc3[nH]cnc23)c(-c2cccc(F)c2)c1C#N] | +++ |

+ means <50 nM
++ means 50 nM to 200 nM
+++ means 50 nM to 100 nM

In some embodiments, the inhibitor of PI3Kδ is selected from:
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
N-{(1S)-1-[5-chloro-8-(3-fluorophenyl)cinnolin-7-yl]ethyl}-9H-purin-6-amine;
and pharmaceutically acceptable salts of any of the aforementioned.

In some embodiments, the inhibitor of PI3Kδ is (S)-7-(1-(9H-purin-6-ylamino)ethyl)-6-(3-fluorophenyl)-3-methyl-5H-thiazolo[3,2-a]pyrimidin-5-one, or a pharmaceutically acceptable salt thereof.

In some embodiments, the inhibitor of PI3Kδ is 4-[1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile, or a pharmaceutically acceptable salt thereof In some embodiments, the inhibitor of PI3Kδ is 4-[1-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile, or a pharmaceutically acceptable salt thereof In some embodiments, the inhibitor of PI3Kδ is 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide, or a pharmaceutically acceptable salt thereof In some embodiments, the inhibitor of PI3Kδ is selected from:
4-[(R)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1(R)-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile;
5-{3-[1 (R)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
4-[(S)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1 (S)-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile;
5-{3-[1 (S)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
and pharmaceutically acceptable salts of any of the aforementioned.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 □g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the TAM kinases in tissue samples, including human, and for identifying TAM kinases ligands by inhibition binding of a labeled compound. Accordingly, the present invention includes TAM kinases assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro TAM kinases labeling and competition assays, compounds that incorporate $^{3}H$, $^{14}C$, $^{82}Br$, $^{125}I$ $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the TAM kinases. Accordingly, the ability of a test compound to compete with the radio-labeled compound for binding to the TAM kinases directly correlates to its binding affinity.

Kits

The present invention also includes pharmaceutical kits useful, for example, in the treatment or prevention of TAM-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

4-(2-(Butylamino)-5-{4-[(4-methylpiperazin-1-yl) methyl]phenyl}imidazo[5,1-f][1,2,4]triazin-7-yl) cyclohexanol (cis- and trans-)

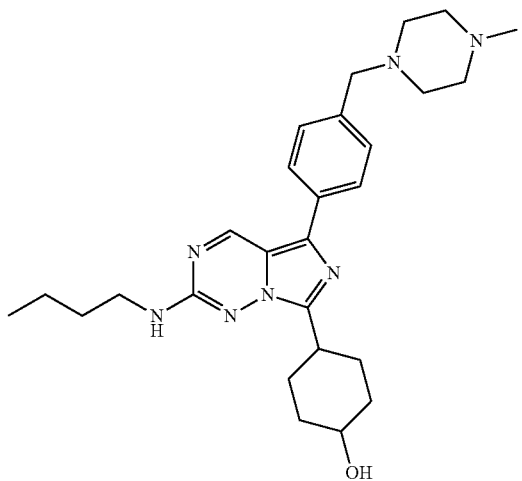 [SMILES: CCCCNc1ncc2c(-c3ccc(CN4CCN(C)CC4)cc3)nc(C3CCC(O)CC3)n2n1]

Step 1. tert-Butyl [2-(1,3-dithian-2-yl)-2-oxoethyl]carbamate

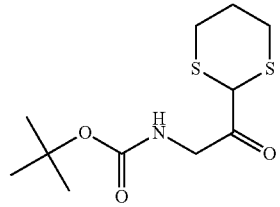 [SMILES: CC(C)(C)OC(=O)NCC(=O)C1SCCCS1]

To a solution of 1,3-dithiane (6.06 g, 50.4 mmol) in tetrahydrofuran (20 mL) stirring at −30° C. was added 2.5 M n-butyllithium in hexanes (18.3 mL, 45.8 mmol) over 10 min. After 30 min, the reaction mixture was cooled to −70° C. before, followed by the addition of a solution of tert-butyl {2-[methoxy(methyl)amino]-2-oxoethyl}carbamate (from Aldrich, 3.00 g, 13.7 mmol) in tetrahydrofuran (50 mL) over 20 min. The resulting solution (yellow) was warmed to about −10° C. over 2 h. The solution was poured into a stirred mixture of ether (200 mL) and 1M sodium dihydrogen phosphate (100 mL). Layers were separated and the organic layer was washed with sodium dihydrogen phosphate and brine. The organic layer was dried over sodium sulfate, filtered and concentrated. The resulting residue was purified by Biotage Isolera (40 g Agela cartridge, eluted with 0-30% EtOAc/hexanes over 15 min) to yield 3.8 g (100%) of the desired product. LCMS calcd for $C_{11}H_{19}NO_3S_2Na$ [M+Na]⁺: m/z=300.1; Found: 300.1. ¹H NMR (400 MHz, $CDCl_3$) δ 5.12 (s, 1H), 4.19 (s, 1H), 3.29-3.14 (m, 2H), 2.56 (ddd, J=13.9, 5.3, 3.1 Hz, 2H), 2.18-1.89 (m, 4H), 1.43 (s, 9H) ppm.

Step 2. tert-Butyl [(2Z)-2-[(aminocarbonothioyl)hydrazono]-2-(1,3-dithian-2-yl)ethyl]carbamate

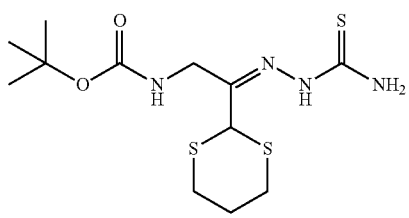 [SMILES: CC(C)(C)OC(=O)NC/C(=N/NC(N)=S)C1SCCCS1]

To a solution of tert-butyl [2-(1,3-dithian-2-yl)-2-oxoethyl]carbamate (23.4 g, 84.4 mmol) in ethanol (250 mL) was added thiosemicarbazide (8.7 g, 96 mmol) and p-toluenesulfonic acid monohydrate (0.60 g, 3.2 mmol). The resulting reaction mixture was heated to 78° C. and stirred overnight (23 h), after which time the solvent was mostly evaporated, and the formation of solid precipitate was observed. Upon adding an excess of ether to the reaction mixture, additional amount of solid precipitated. A stir bar was added and the reaction mixture was stirred vigorously overnight. More solid was formed. The solids were collected by filtration and washed with ether and hexanes. The white solids were dried to give 21.5 g. The filtrate was concentrated to a solid. 30 mL of EtOH was added and stirred for a few minutes before adding excess Ether (~200 mL). The resultant mixture was stirred rapidly for 24 h. The solids thus formed were filtered and washed with hexanes, and dried, to yield 26.3 g (89%) of pure product. LCMS calcd for $C_{12}H_{23}N_4O_2S_3$ [M+H]$^+$: m/z=351.1; Found: 351.3.

Step 3. tert-Butyl {[3-(methylthio)-1,2,4-triazin-6-yl]methyl}carbamate

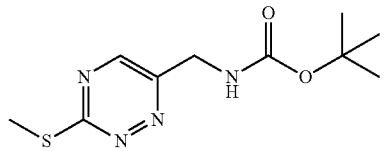 [SMILES: CSc1ncc(CNC(=O)OC(C)(C)C)nn1]

To a solution of tert-butyl [(2Z)-2-[(aminocarbonothioyl)hydrazono]-2-(1,3-dithian-2-yl)ethyl]carbamate (0.50 g, 1.4 mmol) in acetone (9.0 mL) and water (1.1 mL) was added calcium carbonate (0.41 g, 4.1 mmol), followed by dropwise addition of methyl iodide (0.84 mL, 14 mmol). The resulting cloudy mixture was heated to 40° C. and stirred overnight (21 h). The solvent was evaporated then the mixture was added to water. The cloudy mixture was extracted with EtOAc (3×). The combined extracts were washed with water (2×) and brine, dried (sodium sulfate), filtered and concentrated to give an orange residue. The crude was purified on Biotage Isolera (12 g Agela cartridge, eluted with 0-40% EtOAc/hexanes over 15 min) to give 80 mg (20%) of the desired product. LCMS calcd for $C_{10}H_{17}N_4O_2S$ [M+H]$^+$: m/z=257.1; Found: 257.1. $^1$H NMR (500 MHz, CDCl$_3$) δ 8.43 (s, 1H), 4.53 (d, J=6.1 Hz, 2H), 2.63 (s, 3H), 1.42 (s, 9H) ppm.

Step 4. tert-Butyl {[3-(methylsulfonyl)-1,2,4-triazin-6-yl]methyl}carbamate

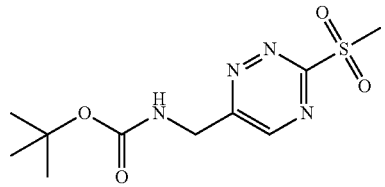 [SMILES: CC(C)(C)OC(=O)NCc1cnc(S(C)(=O)=O)nn1]

To a solution of tert-butyl {[3-(methylthio)-1,2,4-triazin-6-yl]methyl}carbamate (3.3 g, 13 mmol) in methylene chloride (90 mL) was added m-chloroperbenzoic acid (5.55 g, 32.2 mmol). The resulting reaction mixture was stirred at rt. After 4 h of stirring, additional amount of mCPBA (2.8 g) was added, and the resultant reaction mixture was stirred for 3 h more. Saturated sodium bicarbonate and dichloromethane were added to the reaction mixture and the reaction mixture was stirred for 5 minutes. The layers were separated and the organic layer was washed with saturated solution of sodium bicarbonate, dried (MgSO$_4$), filtered and concentrated. The residue was dried in vacuo to give 2.2 g (59%) of a yellow gum. LCMS calcd for $C_{10}H_{16}N_4O_4SNa$ [M+Na]$^+$: m/z=311.1; Found: 311.1. The product was used in the next step without further purification.

Step 5. 4-(Acetyloxy)cyclohexanecarboxylic acid

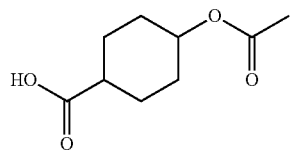

To a solution of 4-hydroxycyclohexanecarboxylic acid (from TCI, cis- and trans-mixture; CAS registry number 17419-81-7; 2.0 g, 14 mmol) in acetic anhydride (9.74 mL, 103 mmol) was added sulfuric acid (2 μL, 0.04 mmol). The resultant reaction mixture was heated to 100° C. and stirred for 2 h. After cooling, some of the excess acetic anhydride was evaporated (bath at 50° C.). To the residue was added water (4 mL) and the reaction mixture was heated to 50° C. for about 1 h. The liquids were evaporated to dryness to give a solid that was dried in vacuo to give 2.6 g (100%) of the desired product as a tan solid that was used without further purification. LCMS calcd for $C_9H_{15}O_4$[M+H]$^+$: m/z=187.1; Found: 187.2. $^1$H NMR (400 MHz, CDCl$_3$) δ 4.93 (dt, J=5.7, 3.0 Hz, 0.5H), 4.68 (tt, J=10.5, 4.0 Hz, 0.5H), 2.42 (td, J=9.3, 4.6 Hz, 0.5H), 2.31 (tt, J=11.5, 3.4 Hz, 0.5H), 2.14-1.96 (m, 5H), 1.92-1.71 (m, 2H), 1.68-1.50 (m, 2H), 1.46-1.28 (m, 2H) ppm.

Step 6. tert-Butyl {[3-(butylamino)-1,2,4-triazin-6-yl]methyl}carbamate

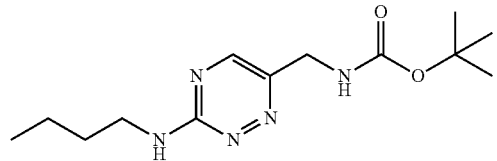 [SMILES: CCCCNc1ncc(CNC(=O)OC(C)(C)C)nn1]

A mixture of tert-butyl {[3-(methylsulfonyl)-1,2,4-triazin-6-yl]methyl}carbamate (2.2 g, 7.6 mmol) and 1-butanamine (3.8 mL, 38 mmol) in tetrahydrofuran (42 mL) was stirred at 40° C. for 2 h. The solvent was evaporated. The residue was purified on Biotage Isolera (40 g Agela cartridge, eluted with 0-50% EtOAc/hexanes over 15 min) to afford 1.2 g (56%) of the desired product. LCMS calcd for $C_{13}H_{24}N_5O_2$ [M+H]$^+$: m/z=282.2; Found: 282.1.

Step 7. 6-(Aminomethyl)-N-butyl-1,2,4-triazin-3-amine dihydrochloride

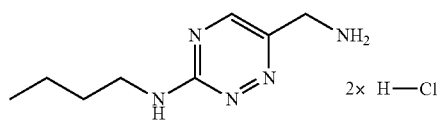

To a solution of tert-butyl {[3-(butylamino)-1,2,4-triazin-6-yl]methyl}carbamate (1.20 g, 4.26 mmol) in methylene chloride (14 mL) was added 4.0 M hydrogen chloride in 1,4-dioxane (5.33 mL, 21.3 mmol). The resulting reaction mixture was stirred at rt for 2 h and then concentrated and dried in vacuo to give 1.19 g (100%) of the product. LCMS calcd for $C_8H_{16}N_5$ [M+H]$^+$: m/z=182.1; Found: 182.1.

Step 8. 4-[({[3-(Butylamino)-1,2,4-triazin-6-yl]methyl}amino) carbonyl]cyclohexyl acetate

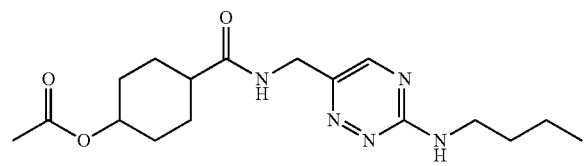 [SMILES: CCCCNc1ncc(CNC(=O)C2CCC(OC(C)=O)CC2)nn1]

To a mixture of 6-(aminomethyl)-N-butyl-1,2,4-triazin-3-amine dihydrochloride (1.19 g, 4.68 mmol) and 4-(acetyloxy)cyclohexanecarboxylic acid (0.959 g, 5.15 mmol) in N,N-dimethylformamide (30.0 mL) was added triethylamine (2.28 mL, 16.4 mmol), followed by the addition of N,N,N',N'-tetramethyl-O-(7-azabenzotriazol-1-yl)uronium hexafluorophosphate (2.14 g, 5.62 mmol). The resulting reaction mixture was stirred at rt overnight. The reaction mixture was diluted with EtOAc then washed with water (2×) and brine. The organic layer was dried (Na$_2$SO$_4$), filtered and concentrated. The residue was purified on Biotage Isolera (40 g Agela cartridge, eluted with 35-100% EtOAc/hexanes) to yield 1.17 g (72%) of the desired product as a mixture of cis/trans isomers mixture. LCMS calcd for $C_{17}H_{28}N_5O_3$ [M+H]$^+$: m/z=350.2; Found: 350.3. $^1$H NMR (400 MHz, DMSO-d$_6$) δ 8.34 (bs, 1H), 8.17 (d, J=3.3 Hz, 1H), 7.78 (bs, 1H), 4.83 (s, 0.5H), 4.53 (dt, J=10.6, 6.5 Hz, 0.5H), 4.30 (d, J=3.1 Hz, 2H), 3.29 (bs, 2H), 2.23 (t, J=10.4 Hz, 0.5H), 2.14 (t, J=11.6 Hz, 0.5H), 1.96 (m, 5H), 1.76 (t, J=10.8 Hz, 2H), 1.64 (t, J=11.4 Hz, 2H), 1.58-1.40 (m, 4H), 1.31 (dt, J=14.8, 7.7 Hz, 2H), 0.88 (t, J=7.3 Hz, 3H) ppm.

Step 9. 4-[2-(Butylamino)imidazo[5,1-f][1,2,4]triazin-7-yl]cyclohexyl acetate

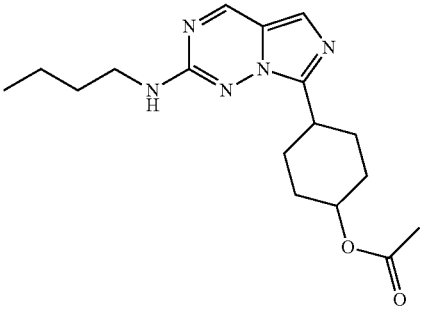 [SMILES: CCCCNc1ncc2cnc(C3CCC(OC(C)=O)CC3)n2n1]

To a mixture of 4-[({[3-(butylamino)-1,2,4-triazin-6-yl]methyl}amino)carbonyl]cyclohexyl acetate (140 mg, 0.40 mmol) and 1H-1,2,4-triazole (83.0 mg, 1.20 mmol) in pyridine (4.0 mL) was added phosphoryl chloride (56.0 μL, 0.601 mmol). The resulting reaction mixture was stirred at rt overnight, after which time additional amounts of 1H-1,2,4-triazole (83 mg) and phosphoryl chloride (56 uL) were added. After stirring for another 6 h, the reaction mixture was quenched with a small amount of MeOH and about 1 mL of NH$_4$OH. The reaction mixture was diluted with EtOAc then washed with 0.1N HCl (2×). The organic layer was dried (MgSO$_4$), filtered and concentrated. The resulting residue was purified on Biotage Isolera (12 g Agela cartridge, eluted with 20-75% EtOAc/hexanes over 15 min) to give 33 mg (25%) of the desired product. LCMS calcd for $C_{17}H_{26}N_5O_2$ [M+H]$^+$: m/z=332.2; Found: 332.2.

Step 10. 4-[5-Bromo-2-(butylamino)imidazo[5,1-f][1,2,4]triazin-7-yl]cyclohexyl acetate

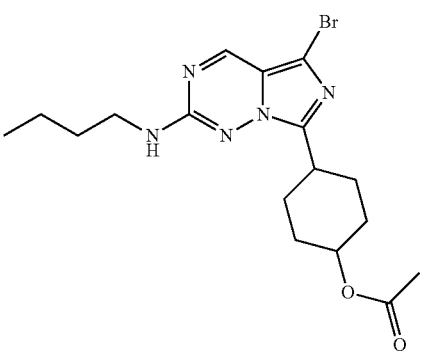 [SMILES: CCCCNc1ncc2c(Br)nc(C3CCC(OC(C)=O)CC3)n2n1]

To a solution of 4-[2-(butylamino)imidazo[5,1-f][1,2,4]triazin-7-yl]cyclohexyl acetate (60 mg, 0.2 mmol) in N,N-dimethylformamide (1.0 mL, 13 mmol) was added N-bromosuccinimide (32.2 mg, 0.181 mmol). The resulting reaction mixture was stirred at rt for 3 h. To the reaction mixture was added saturated solution of sodium bicarbonate and EtOAc. The mixture was stirred vigorously then the layers were separated and the aqueous layer was extracted with EtOAc (2×). The combined organic extracts were dried (Na$_2$SO$_4$), filtered and concentrated to yield 73 mg (100%) of the desired product as a solid. LCMS calcd for $C_{17}H_{25}BrN_5O_2$ [M+H]$^+$: m/z=410.1; Found: 410.2.

Step 11. 4-(2-(Butylamino)-5-{4-[(4-methylpiperazin-1-yl)methyl]phenyl}imidazo[5,1-f][1,2,4]triazin-7-yl)cyclohexanol (cis- and trans-)

Into a microwave vial was added 4-[5-bromo-2-(butylamino)imidazo[5,1-f][1,2,4]triazin-7-yl]cyclohexyl acetate (19 mg, 0.046 mmol), 1-methyl-4-[4-(4,4,5,5-tetramethyl-1,3,2-dioxaborolan-2-yl)benzyl]piperazine (from Alfa Aesar, 22 mg, 0.069 mmol), tetrakis(triphenylphosphine)palladium(0) (5.4 mg, 0.0046 mmol) and potassium carbonate (13 mg, 0.093 mmol), tetrahydrofuran (0.50 mL) and water (0.13 mL). The reaction mixture was degassed, the vial was capped and heated in the microwave at 150° C. for 20 min. The reaction mixture was filtered through Celite and concentrated to yield the intermediate 4-(2-(butylamino)-5-(4-((4-methylpiperazin-1-yl)methyl)phenyl)imidazo[5,1-f][1,2,4]triazin-7-yl)cyclohexyl acetate. To the residue containing the intermediate was added methanol (0.40 mL) and potassium carbonate (32 mg, 0.23 mmol) and the reaction mixture was stirred overnight. The reaction mixture was filtered, then diluted and purified using prep-LCMS (XBridge™ C18 column, eluting with a gradient of MeCN/water containing 0.05% TFA, at a flow rate of 60 mL/min) to give the desired products. On analytic LCMS [Waters SunFire HPLC column (C18, 2.1×50 mm, 5 µM), injection volume 2 µL, flow rate 3 mL/min, gradient from 2 to 80% B in 3 minutes (A=water with 0.025% TFA; B=acetonitrile)]: The first peak (trans-4-(2-(Butylamino)-5-{4-[(4-methylpiperazin-1-yl)methyl]phenyl}imidazo[5,1-f][1,2,4]triazin-7-yl)cyclohexanol) (4.2 mg) retention time is 1.577 min. LCMS calcd for $C_{27}H_{40}N_7O$ [M+H]$^+$: m/z=478.3; Found: 478.3. $^1$H NMR (400 MHz, DMSO-d$_6$) δ 9.27 (s, 1H), 7.95 (d, J=8.1 Hz, 2H), 7.45 (d, J=8.1 Hz, 2H), 7.36 (m, 1H), 3.89 (bs, 1H), 3.54-3.43 (m, 2H), 3.23 (m, 3H), 3.14-2.98 (m, 4H), 2.79 (s, 3H), 1.97 (m, 4H), 1.75 (t, J=11.5 Hz, 4H), 1.43-1.21 (m, 6H), 0.93 (t, J=7.3 Hz, 3H) ppm. The second peak (cis-4-(2-(Butylamino)-5-{4-[(4-methylpiperazin-1-yl)methyl]phenyl}imidazo[5,1-f][1,2,4]triazin-7-yl)cyclohexanol) (2.1 mg) retention time is 1.722 min. LCMS calcd for $C_{27}H_{40}N_7O$ [M+H]$^+$: m/z=478.3; Found: 478.3.

Example 2

4-{2-(Butylamino)-5-[4-(morpholin-4-ylmethyl)phenyl]imidazo[5,1-f][1,2,4]triazin-7-yl}cyclohexanol (cis- and trans-)

Into a microwave vial was added 4-[5-bromo-2-(butylamino)imidazo[5,1-f][1,2,4]triazin-7-yl]cyclohexyl acetate (Prepared in Example 1, Step 10; 19 mg, 0.046 mmol), 4-[4-(4,4,5,5-tetramethyl-1,3,2-dioxaborolan-2-yl)benzyl]morpholine (from Aldrich, 17 mg, 0.056 mmol), tetrakis(triphenylphosphine)palladium(0) (5.4 mg, 0.0046 mmol) and potassium carbonate (13 mg, 0.093 mmol), tetrahydrofuran (0.50 mL) and water (0.13 mL). The reaction mixture degassed, the vial was capped and the reaction mixture was heated in the microwave at 150° C. for 20 min. The reaction mixture was filtered through Celite and concentrated to yield the intermediate 4-(2-(butylamino)-5-(4-(morpholinomethyl)phenyl)imidazo[5,1-f][1,2,4]triazin-7-yl)cyclohexyl acetate. To the residue containing the intermediate was added methanol (0.40 mL) and potassium carbonate (32 mg, 0.23 mmol) and the reaction mixture was stirred overnight. The reaction mixture was filtered then diluted and purified on prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 µM), injection volume 2 µL, flow rate 3 mL/min, gradient from 2 to 80% B in 3 minutes (A=water with 0.025% TFA; B=acetonitrile)]: The first peak (trans-4-{2-(Butylamino)-5-[4-(morpholin-4-ylmethyl)phenyl]imidazo[5,1-f][1,2,4]triazin-7-yl}cyclohexanol) (1.1 mg) retention time is 1.643 min. LCMS calcd for $C_{26}H_{37}N_6O_2$ [M+H]$^+$: m/z=465.3; Found: 465.3. The second peak (cis-4-{2-(Butylamino)-5-[4-(morpholin-4-ylmethyl)phenyl]imidazo[5,1-f][1,2,4]triazin-7-yl}cyclohexanol) (1.0 mg) retention time is 1.817 min. LCMS calcd for $C_{26}H_{37}N_6O_2$ [M+H]$^+$: m/z=465.3; Found: 465.3. $^1$H NMR (500 MHz, CDCl$_3$) δ 8.91 (s, 1H), 7.80 (d, J=7.1 Hz, 2H), 7.42 (bs, 2H), 4.83 (t, J=5.7 Hz, 1H), 4.05 (tt, J=5.2, 3.1 Hz, 1H), 3.73 (bs, 4H), 3.55 (bs, 2H), 3.38-3.33 (m, 2H), 3.29 (tt, J=10.2, 3.8 Hz, 1H), 2.48 (bs, 4H), 2.33-2.21 (m, 2H), 1.93 (dt, J=13.0, 4.3 Hz, 2H), 1.84 (dq, J=13.1, 4.1 Hz, 2H), 1.79-1.70 (m, 2H), 1.69-1.60 (m, 2H), 1.44 (dq, J=14.5, 7.3 Hz, 2H), 0.96 (t, J=7.4 Hz, 3H) ppm.

Example 3

4-{2-(Butylamino)-5-[4-(hydroxymethyl)phenyl]imidazo[5,1-f][1,2,4]triazin-7-yl}cyclohexanol (cis- and trans-)

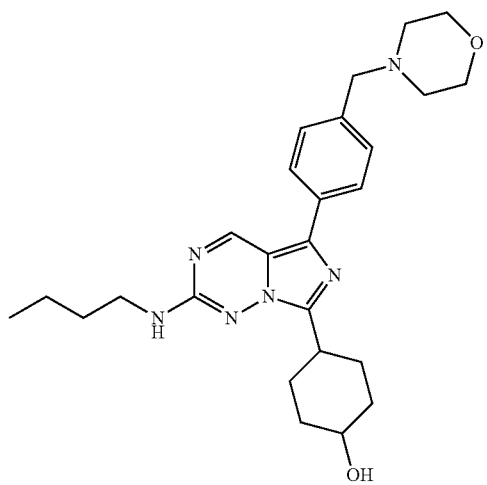 [SMILES: CCCCNc1ncc2c(-c3ccc(CN4CCOCC4)cc3)nc(C3CCC(O)CC3)n2n1]

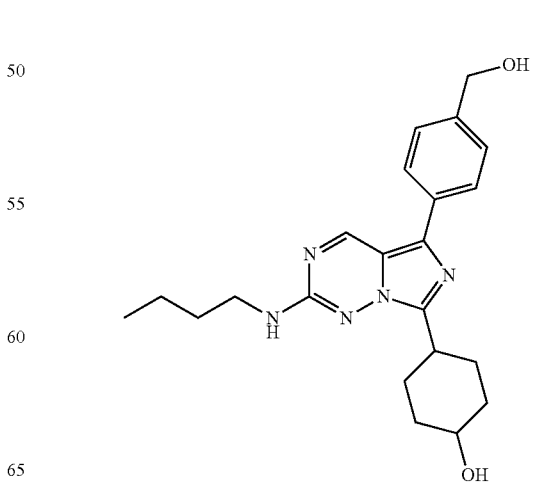

Into a microwave vial was added 4-[5-bromo-2-(butylamino)imidazo[5,1-f][1,2,4]triazin-7-yl]cyclohexyl acetate (Prepared in Example 1, Step 10; 15 mg, 0.035 mmol), 4-hydroxymethylbenzeneboronic acid (from Aldrich, 8.1 mg, 0.053 mmol), tetrakis(triphenylphosphine)palladium(0) (4.1 mg, 0.0035 mmol) and potassium carbonate (9.8 mg, 0.071 mmol), tetrahydrofuran (0.48 mL) and water (0.12 mL). the reaction mixture degassed, the vial was capped and the reaction mixture was heated in the microwave at 150° C. for 20 min. The reaction mixture was filtered through Celite and concentrated to yield intermediate 4-(2-(butylamino)-5-(4-(hydroxymethyl)phenyl)imidazo[5,1-f][1,2,4]triazin-7-yl)cyclohexyl acetate. To the residue containing the intermediate was added methanol (0.40 mL) and potassium carbonate (32 mg, 0.23 mmol) and the reaction mixture stirred overnight. The mixture was filtered then diluted and purified using prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 μM), injection volume 2 μL, flow rate 3 mL/min, gradient from 2 to 80% B in 3 minutes (A=water with 0.025% TFA; B=acetonitrile)]: The first peak (trans-4-{2-(Butylamino)-5-[4-(hydroxymethyl)phenyl]imidazo[5,1-f][1,2,4]triazin-7-yl}cyclohexanol) (3.2 mg) retention time is 1.723 min. LCMS calcd for $C_{22}H_{30}N_5O_2$ [M+H]$^+$: m/z=396.2; Found: 396.2. $^1$H NMR (400 MHz, DMSO-d$_6$) δ 9.23 (s, 1H), 7.88 (d, J=8.2 Hz, 2H), 7.37 (d, J=8.1 Hz, 2H), 7.28 (t, J=5.5 Hz, 1H), 5.22 (bs, 1H), 4.60 (bs, 1H), 4.52 (s, 2H), 3.49 (m, 1H), 3.22 (q, J=6.5 Hz, 2H), 3.05 (t, J=11.7 Hz, 1H), 1.97 (m, 4H), 1.82-1.67 (m, 2H), 1.59 (dt, J=14.8, 7.3 Hz, 2H), 1.42-1.10 (m, 4H), 0.93 (t, J=7.4 Hz, 3H) ppm. The second peak (cis-4-{2-(Butylamino)-5-[4-(hydroxymethyl)phenyl]imidazo[5,1-f][1,2,4]triazin-7-yl}cyclohexanol) (3.2 mg) retention time is 2.105 min. LCMS calcd for $C_{22}H_{30}N_5O_2$ [M+H]$^+$: m/z=396.2; Found: 396.2.

Example 4

4-[2-(Butylamino)-5-(1H-indol-5-yl)imidazo[5,1-f][1,2,4]triazin-7-yl]cyclohexanol (cis- and trans-)

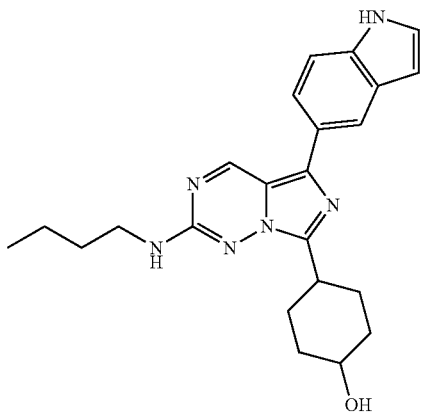 [SMILES: CCCCNc1ncc2c(-c3ccc4[nH]ccc4c3)nc(C3CCC(O)CC3)n2n1]

Into a microwave vial was added 4-[5-bromo-2-(butylamino)imidazo[5,1-f][1,2,4]triazin-7-yl]cyclohexyl acetate (Prepared in Example 1, Step 10; 15 mg, 0.035 mmol), 1H-indol-5-ylboronic acid (from Aldrich, 8.5 mg, 0.053 mmol), tetrakis(triphenylphosphine)palladium(0) (4.1 mg, 0.0035 mmol) and potassium carbonate (9.8 mg, 0.071 mmol), tetrahydrofuran (0.48 mL) and water (0.12 mL). The reaction mixture was degassed, the vial was capped and the reaction mixture was heated in the microwave at 150° C. for 20 min. The reaction mixture was filtered through Celite and concentrated to yield intermediate 4-(2-(butylamino)-5-(1H-indol-5-yl)imidazo[5,1-f][1,2,4]triazin-7-yl)cyclohexyl acetate. To the residue containing the intermediate was added methanol (0.40 mL) and potassium carbonate (32 mg, 0.23 mmol) and the reaction mixture was stirred overnight. The reaction mixture was filtered then diluted and purified using prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 μM), injection volume 2 μL, flow rate 3 mL/min, gradient from 2 to 80% B in 3 minutes (A=water with 0.025% TFA; B=acetonitrile)]: The first peak (4.5 mg) retention time is 1.776 min. LCMS calcd for $C_{23}H_{29}N_6O$ [M+H]$^+$: m/z=405.2; Found: 405.2. The second peak (2.9 mg) retention time is 1.889 min. LCMS calcd for $C_{23}H_{29}N_6O$ [M+H]$^+$: m/z=405.2; Found: 405.2.

Example 5

4-[2-(Butylamino)-5-(4-piperazin-1-ylphenyl)imidazo[5,1-f][1,2,4]triazin-7-yl]cyclohexanol (cis- and trans-)

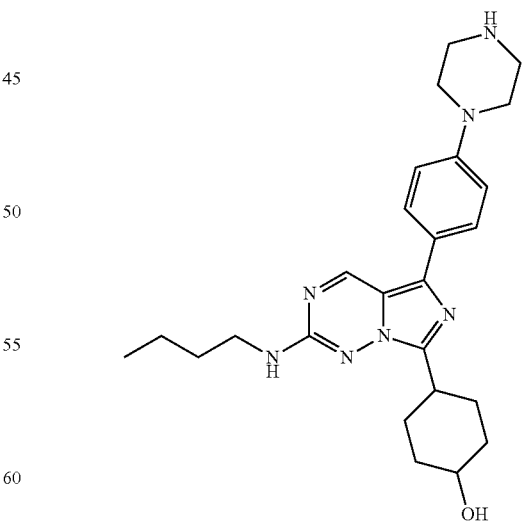

A mixture of 4-[5-bromo-2-(butylamino)imidazo[5,1-f][1,2,4]triazin-7-yl]cyclohexyl acetate (Prepared in Example 1, Step 10; 15 mg, 0.035 mmol), 1-[4-(4,4,5,5-tetramethyl-1,3,2-dioxaborolan-2-yl)phenyl]piperazine (from Combi- Blocks, 15 mg, 0.053 mmol), tetrakis(triphenylphosphine)palladium(0) (4.1 mg, 0.0035 mmol) and potassium carbonate (9.8 mg, 0.071 mmol) in tetrahydrofuran (0.48 mL) and water (0.12 mL) was heated in the microwave at 150° C. for 20 min. The reaction mixture was cooled then filtered through Celite and concentrated to yield the intermediate 4-(2-(butylamino)-5-(4-(piperazin-1-yl)phenyl)imidazo[5,1-f][1,2,4]triazin-7-yl)cyclohexyl acetate. To the residue containing the intermediate was added methanol (0.30 mL) and potassium carbonate (24 mg, 0.18 mmol) and the reaction mixture was stirred overnight at rt. The reaction mixture was filtered and purified using prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 µM), injection volume 2 µL, flow rate 3 mL/min, gradient from 2 to 80% B in 3 minutes (A=water with 0.025% TFA; B=acetonitrile)]: The first peak (trans-4-[2-(Butylamino)-5-(4-piperazin-1-ylphenyl)imidazo[5,1-f][1,2,4]triazin-7-yl]cyclohexanol) (3.2 mg) retention time is 1.323 min. LCMS calcd for $C_{25}H_{36}N_7O$ [M+H]$^+$: m/z=450.3; Found: 450.3. $^1$H NMR (500 MHz, DMSO-d$_6$) δ 9.13 (s, 1H), 7.76 (d, J=8.9 Hz, 2H), 7.19 (t, J=5.7 Hz, 1H), 6.96 (d, J=8.9 Hz, 2H), 4.60 (d, J=4.0 Hz, 1H), 3.47 (m, 1H), 3.21 (q, J=6.7 Hz, 2H), 3.11-3.06 (m, 4H), 3.02 (t, J=12.0 Hz, 1H), 2.86-2.79 (m, 4H), 1.96 (m, 4H), 1.79-1.67 (m, 2H), 1.58 (p, J=7.3 Hz, 2H), 1.37 (dt, J=14.6, 7.3 Hz, 2H), 1.33-1.12 (m, 2H), 0.92 (t, J=7.4 Hz, 3H) ppm. The second peak (cis-4-[2-(Butylamino)-5-(4-piperazin-1-ylphenyl)imidazo[5,1-f][1,2,4]triazin-7-yl]cyclohexanol) (1.7 mg) retention time is 1.458 min. LCMS calcd for $C_{25}H_{36}N_7O$ [M+H]$^+$: m/z=450.3; Found: 450.3.

Example 6

4-[2-(Butylamino)-5-(2-piperazin-1-ylpyridin-4-yl)imidazo[5,1-f][1,2,4]triazin-7-yl]cyclohexanol (cis- and trans-)

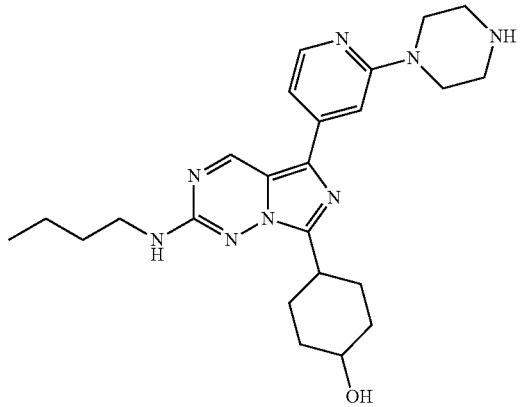 [SMILES: CCCCNc1ncc2c(-c3ccnc(N4CCNCC4)c3)nc(C3CCC(O)CC3)n2n1]

A mixture of 4-[5-bromo-2-(butylamino)imidazo[5,1-f][1,2,4]triazin-7-yl]cyclohexyl acetate (Prepared in Example 1, Step 10; 15 mg, 0.035 mmol), 1-[4-(4,4,5,5-tetramethyl-1,3,2-dioxaborolan-2-yl)pyridin-2-yl]piperazine (from Aldrich, 15 mg, 0.053 mmol), tetrakis(triphenylphosphine)palladium(0) (4.1 mg, 0.0035 mmol) and potassium carbonate (9.8 mg, 0.071 mmol) in tetrahydrofuran (0.48 mL) and water (0.12 mL) was heated in the microwave at 150° C. for 20 min. The reaction mixture was cooled then filtered through Celite and concentrated to yield intermediate 4-(2-(butylamino)-5-(2-(piperazin-1-yl)pyridin-4-yl)imidazo[5,1-f][1,2,4]triazin-7-yl)cyclohexyl acetate. To the residue containing the intermediate was added methanol (0.30 mL) and potassium carbonate (24 mg, 0.177 mmol) and the reaction mixture was stirred overnight at rt. The reaction mixture was filtered and purified using prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 µM), injection volume 2 µL, flow rate 3 mL/min, gradient from 2 to 80% B in 3 minutes (A=water with 0.025% TFA; B=acetonitrile)]: The first peak (trans-4-[2-(Butylamino)-5-(2-piperazin-1-ylpyridin-4-yl)imidazo[5,1-f][1,2,4]triazin-7-yl]cyclohexanol) (3.6 mg) retention time is 1.367 min. LCMS calcd for $C_{24}H_{35}N_8O$ [M+H]$^+$: m/z=451.3; Found: 451.3. $^1$H NMR (500 MHz, DMSO-d$_6$) δ 9.30 (s, 1H), 8.12 (d, J=5.3 Hz, 1H), 7.39 (t, J=5.7 Hz, 1H), 7.17-7.10 (m, 2H), 4.61 (s, 1H), 3.53-3.40 (m, 5H), 3.23 (q, J=6.6 Hz, 2H), 3.10-3.00 (m, 1H), 2.82-2.75 (m, 4H), 1.97 (m, 4H), 1.80-1.68 (m, 2H), 1.59 (p, J=7.3 Hz, 2H), 1.36 (dt, J=14.5, 7.3 Hz, 2H), 1.32-1.20 (m, 2H), 0.92 (t, J=7.4 Hz, 3H) ppm. The second peak (cis-4-[2-(Butylamino)-5-(2-piperazin-1-ylpyridin-4-yl)imidazo[5,1-f][1,2,4]triazin-7-yl]cyclohexanol) (4 mg) retention time is 1.620 min. LCMS calcd for $C_{24}H_{35}N_8O$ [M+H]$^+$: m/z=451.3; Found: 451.3.

Example 7

4-[2-(Butylamino)-5-(3-fluoro-4-morpholin-4-ylphenyl)imidazo[5,1-f][1,2,4]triazin-7-yl]cyclohexanol (cis- and trans-)

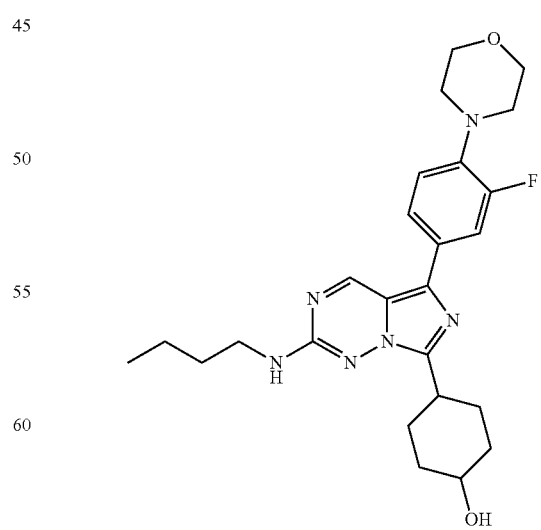

Into a microwave vial was added 4-[5-bromo-2-(butylamino)imidazo[5,1-f][1,2,4]triazin-7-yl]cyclohexyl acetate (Prepared in Example 1, Step 10; 15 mg, 0.035 mmol), 4-[2-fluoro-4-(4,4,5,5-tetramethyl-1,3,2-dioxaborolan-2-yl)phenyl]morpholine (from Alfa Aesar, 16 mg, 0.053 mmol), tetrakis(triphenylphosphine)palladium(0) (4.1 mg, 0.0035 mmol) and potassium carbonate (9.8 mg, 0.071 mmol), tetrahydrofuran (0.48 mL) and water (0.12 mL). The reaction mixture was degassed, the vial was capped and the reaction mixture was heated in the microwave at 150° C. for 30 min. The reaction mixture was filtered through Celite and concentrated to yield the intermediate 4-(2-(butylamino)-5-(3-fluoro-4-morpholinophenyl)imidazo[5,1-f][1,2,4]triazin-7-yl)cyclohexyl acetate. To the residue containing the intermediate was added methanol (0.40 mL) and potassium carbonate (32 mg, 0.23 mmol) and the reaction mixture was stirred overnight. The reaction mixture was filtered then diluted and purified using prep-LCMS (XBridge™ C18 column, eluting with a gradient of MeCN/water containing 0.1% ammonium hydroxide, at a flow rate of 60 mL/min) to give the desired products. On analytic LCMS [Waters SunFire HPLC column (C18, 2.1×50 mm, 5 M), injection volume 2 µL, flow rate 3 mL/min, gradient from 2 to 80% B in 3 minutes (A=water with 0.025% TFA; B=acetonitrile)]: The first peak (3.5 mg) retention time is 2.270 min. LCMS calcd for $C_{25}H_{34}FN_6O_2[M+H]^+$: m/z=469.3; Found: 469.3. The second peak (2.9 mg) retention time is 2.391 min. LCMS calcd for $C_{25}H_{34}FN_6O_2[M+H]^+$: m/z=469.3; Found: 469.3.

Example 8

4-{2-(Butylamino)-5-[3-(hydroxymethyl)phenyl]imidazo[5,1-f][1,2,4]triazin-7-yl}cyclohexanol (cis- and trans-)

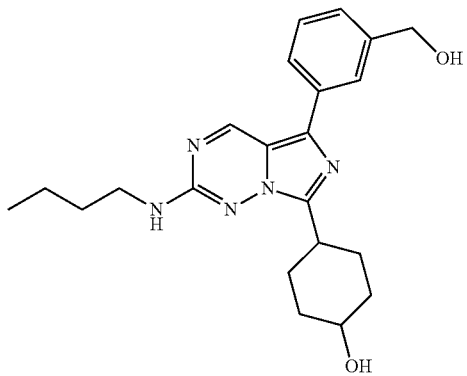 [SMILES: CCCCNc1ncc2c(-c3cccc(CO)c3)nc(C3CCC(O)CC3)n2n1]

Into a microwave vial was added 4-[5-bromo-2-(butylamino)imidazo[5,1-f][1,2,4]triazin-7-yl]cyclohexyl acetate (Prepared in Example 1, Step 10; 13 mg, 0.032 mmol), [3-(hydroxymethyl)phenyl]boronic acid (from Aldrich, 7.2 mg, 0.048 mmol), tetrakis(triphenylphosphine)palladium(0) (3.7 mg, 0.0032 mmol) and potassium carbonate (8.8 mg, 0.063 mmol), tetrahydrofuran (0.48 mL) and water (0.12 mL). The reaction mixture was degassed, the vial was capped and the reaction mixture was heated in the microwave at 150° C. for 20 min. The mixture was filtered through Celite and concentrated to yield intermediate 4-(2-(butylamino)-5-(3-(hydroxymethyl)phenyl)imidazo[5,1-f][1,2,4]triazin-7-yl)cyclohexyl acetate. To the residue containing the intermediate was added methanol (0.40 mL) and potassium carbonate (22 mg, 0.16 mmol) and the reaction mixture was stirred overnight. The reaction mixture was filtered then diluted and purified using prep-LCMS (XBridge™ C18 column, eluting with a gradient of MeCN/water containing 0.05% TFA, at a flow rate of 60 mL/min) to give the desired products. On analytic LCMS [Waters SunFire HPLC column (C18, 2.1×50 mm, 5 µM), injection volume 2 µL, flow rate 3 mL/min, gradient from 2 to 80% B in 3 minutes (A=water with 0.025% TFA; B=acetonitrile)]: The first peak (2.8 mg) retention time is 1.707 min. LCMS calcd for $C_{22}H_{30}N_5O_2$ $[M+H]^+$: m/z=396.2; Found: 396.3. The second peak retention time is 1.906 min. LCMS calcd for $C_{22}H_{30}N_5O_2$ $[M+H]^+$: m/z=396.2; Found: 396.3.

Example 9

N-{3-[2-(Butylamino)-7-(4-hydroxycyclohexyl)imidazo[5,1-f][1,2,4]triazin-5-yl]phenyl}acetamide (cis- and trans-)

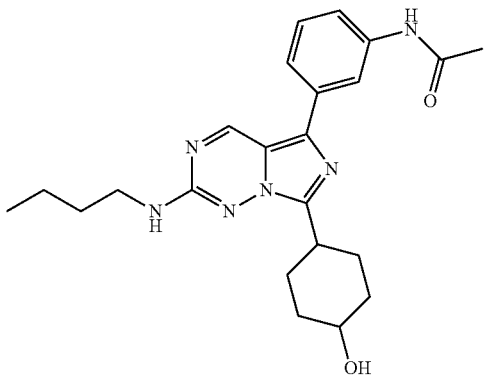 [SMILES: CCCCNc1ncc2c(-c3cccc(NC(C)=O)c3)nc(C3CCC(O)CC3)n2n1]

Into a microwave vial was added 4-[5-bromo-2-(butylamino)imidazo[5,1-f][1,2,4]triazin-7-yl]cyclohexyl acetate (Prepared in Example 1, Step 10; 13 mg, 0.032 mmol), [3-(acetylamino)phenyl]boronic acid (from Aldrich, 8.5 mg, 0.048 mmol), tetrakis(triphenylphosphine)palladium(0) (3.7 mg, 0.0032 mmol) and potassium carbonate (8.8 mg, 0.063 mmol), tetrahydrofuran (0.48 mL) and water (0.12 mL). The resultant reaction mixture was degassed, the vial was capped and the reaction mixture was heated in the microwave at 150° C. for 20 min. The reaction mixture was filtered through Celite and concentrated to yield the intermediate 4-(5-(3-acetamidophenyl)-2-(butylamino)imidazo[5,1-f][1,2,4]triazin-7-yl)cyclohexyl acetate. To the residue containing the intermediate was added methanol (0.40 mL) and potassium carbonate (22 mg, 0.16 mmol) and the mixture stirred overnight. The reaction mixture was filtered then diluted and purified using prep-LCMS (XBridge™ C18 column, eluting with a gradient of MeCN/water containing 0.05% TFA, at a flow rate of 60 mL/min) to give the desired products. On analytic LCMS [Waters SunFire HPLC column (C18, 2.1×50 mm, 5 µM), injection volume 2 µL, flow

Example 10

N-{4-[2-(Butylamino)-7-(4-hydroxycyclohexyl)imidazo[5,1-f][1,2,4]triazin-5-yl]phenyl}acetamide (cis- and trans-)

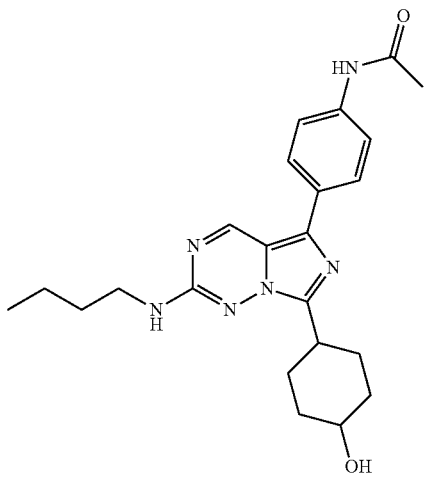 [SMILES: CCCCNc1ncc2c(-c3ccc(NC(C)=O)cc3)nc(C3CCC(O)CC3)n2n1]

Into a microwave vial was added 4-[5-bromo-2-(butylamino)imidazo[5,1-f][1,2,4]triazin-7-yl]cyclohexyl acetate (Prepared in Example 1, Step 10; 13 mg, 0.032 mmol), [4-(acetylamino)phenyl]boronic acid (from Aldrich, 8.5 mg, 0.048 mmol), tetrakis(triphenylphosphine)palladium(0) (3.7 mg, 0.0032 mmol) and potassium carbonate (8.8 mg, 0.063 mmol), tetrahydrofuran (0.48 mL) and water (0.12 mL). The reaction mixture was degassed, the vial was capped and the reaction mixture was heated in the microwave at 150° C. for 20 min. The mixture was filtered through Celite and concentrated to yield the intermediate 4-(5-(4-acetamidophenyl)-2-(butylamino)imidazo[5,1-f][1,2,4]triazin-7-yl)cyclohexyl acetate. To the residue containing the intermediate was added methanol (0.40 mL) and potassium carbonate (22 mg) and the reaction mixture was stirred overnight. The reaction mixture was filtered then diluted and purified using prep-LCMS (XBridge™ C18 column, eluting with a gradient of MeCN/water containing 0.05% TFA, at a flow rate of 60 mL/min) to give the desired products. On analytic LCMS [Waters SunFire HPLC column (C18, 2.1×50 mm, 5 μM), injection volume 2 μL, flow rate 3 mL/min, gradient from 2 to 80% B in 3 minutes (A=water with 0.025% TFA; B=acetonitrile)]: The first peak (2.1 mg) retention time is 1.976 min. LCMS calcd for $C_{23}H_{31}N_6O_2$ [M+H]$^+$: m/z=423.2; Found: 423.2. The second peak (1.6 mg) retention time is 2.131 min. LCMS calcd for $C_{23}H_{31}N_6O_2$ [M+H]$^+$: m/z=423.2; Found: 423.2.

rate 3 mL/min, gradient from 2 to 80% B in 3 minutes (A=water with 0.025% TFA; B=acetonitrile)]: The first peak (1.5 mg) retention time is 2.085 min. LCMS calcd for $C_{23}H_{31}N_6O_2$ [M+H]$^+$: m/z=423.2; Found: 423.2. The second peak (1.8 mg) retention time is 2.236 min. LCMS calcd for $C_{23}H_{31}N_6O_2$ [M+H]$^+$: m/z=423.2; Found: 423.2.

Example 11

4-(2-(Butylamino)-5-{4-[(methylamino)methyl]phenyl}imidazo[5,1-f][1,2,4]triazin-7-yl)cyclohexanol (cis- and trans-)

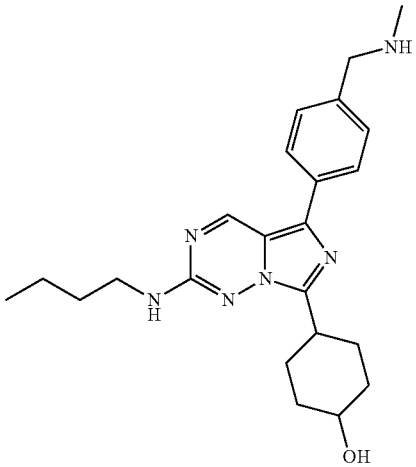 [SMILES: CCCCNc1ncc2c(-c3ccc(CNC)cc3)nc(C3CCC(O)CC3)n2n1]

Step 1. 4-[2-(Butylamino)-5-(4-formylphenyl)imidazo[5,1-f][1,2,4]triazin-7-yl]cyclohexyl acetate

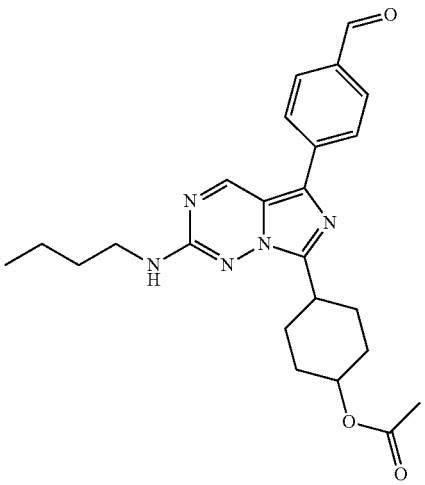 [SMILES: CCCCNc1ncc2c(-c3ccc(C=O)cc3)nc(C3CCC(OC(C)=O)CC3)n2n1]

Into a microwave vial was added 4-[5-bromo-2-(butylamino)imidazo[5,1-f][1,2,4]triazin-7-yl]cyclohexyl acetate (Prepared in Example 1, Step 10; 50 mg, 0.1 mmol), (4-formylphenyl)boronic acid (27 mg, 0.18 mmol), tetrakis(triphenylphosphine)palladium(0) (14 mg, 0.012 mmol), and potassium carbonate (34 mg, 0.24 mmol), tetrahydrofuran (1.6 mL) and water (0.40 mL). The reaction mixture was degassed, the vial was capped and the reaction mixture was heated in the microwave at 150° C. for 20 min. The reaction mixture was filtered through Celite and concentrated. The residue was purified on Biotage Isolera (10 g SNAP cartridge, eluted with 5-50% EtOAc/hexanes over 13 min) to yield 18 mg (30%) of the desired product. LCMS calcd for $C_{24}H_{30}N_5O_3$ [M+H]$^+$: m/z=436.2; Found: 436.2.

Step 2. 4-(2-(Butylamino)-5-{4-[(methylamino)
methyl]phenyl}imidazo[5,1-f][1,2,4]triazin-7-yl)
cyclohexanol (cis- and trans-)

To a mixture of 4-[2-(butylamino)-5-(4-formylphenyl)
imidazo[5,1-f][1,2,4]triazin-7-yl]cyclohexyl acetate (9.0
mg, 0.021 mmol) and 2.0 M methylamine in THF (12 µL,
0.025 mmol) stirring in methylene chloride (0.50 mL) was
added sodium triacetoxyborohydride (8.8 mg, 0.041 mmol).
The resulting reaction mixture was stirred overnight at rt,
then concentrated to yield the intermediate 4-(2-(buty-
lamino)-5-(4-((methylamino)methyl)phenyl)imidazo[5,1-f]
[1,2,4]triazin-7-yl)cyclohexyl acetate. To the resulting resi-
due containing the intermediate was added methanol (0.40
mL) and potassium carbonate (14 mg, 0.10 mmol). The
reaction mixture was stirred for 6 h at rt then filtered and
purified using prep-LCMS (XBridge™ C18 column, eluting
with a gradient of MeCN/water containing 0.1% ammonium
hydroxide, at a flow rate of 60 mL/min) to give the desired
products. On analytic LCMS [Waters SunFire HPLC col-
umn (C18, 2.1×50 mm, 5 µM), injection volume 2 µL, flow
rate 3 mL/min, gradient from 2 to 80% B in 3 minutes
(A=water with 0.025% TFA; B=acetonitrile)]: The first peak
(1.5 mg) retention time is 1.589 min. LCMS calcd for
$C_{23}H_{33}N_6O$ $[M+H]^+$: m/z=409.3; Found: 409.3. The second
peak (2.6 mg) retention time is 1.752 min. LCMS calcd for
$C_{23}H_{33}N_6O$ $[M+H]^+$: m/z=409.3; Found: 409.3.

Example 12

4-(2-(Butylamino)-5-{4-[(cyclohexylamino)methyl]
phenyl}imidazo[5,1-f][1,2,4]triazin-7-yl)cyclohexa-
nol (cis- and trans-)

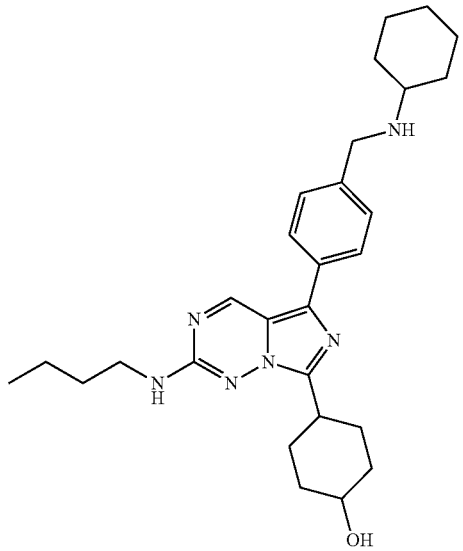 [SMILES: CCCCNc1ncc2c(-c3ccc(CNC4CCCCC4)cc3)nc(C3CCC(O)CC3)n2n1]

To a mixture of 4-[2-(butylamino)-5-(4-formylphenyl)
imidazo[5,1-f][1,2,4]triazin-7-yl]cyclohexyl acetate (Pre-
pared in Example 11; Step 1; 9.0 mg, 0.021 mmol) and
cyclohexanamine (2.8 µL, 0.025 mmol) stirring in methyl-
ene chloride (0.50 mL) was added sodium triacetoxyboro-
hydride (8.8 mg, 0.041 mmol). The resulting reaction mix-
ture was stirred overnight at rt, then concentrated to yield the
intermediate 4-(2-(butylamino)-5-(4-((cyclohexylamino)
methyl)phenyl)imidazo[5,1-f][1,2,4]triazin-7-yl)cyclohexyl
acetate. To the resulting residue containing the intermediate
was added methanol (0.40 mL) and potassium carbonate (14
mg, 0.10 mmol). The reaction mixture was stirred for 6 h at
rt then filtered and purified using prep-LCMS (XBridge™
C18 column, eluting with a gradient of MeCN/water con-
taining 0.1% ammonium hydroxide, at a flow rate of 60
mL/min) to give the desired products. On analytic LCMS
[Waters SunFire HPLC column (C18, 2.1×50 mm, 5 µM),
injection volume 2 µL, flow rate 3 mL/min, gradient from 2
to 80% B in 3 minutes (A=water with 0.025% TFA;
B=acetonitrile)]: The first peak (2.5 mg) retention time is
1.589 min. LCMS calcd for $C_{28}H_{41}N_6O$ $[M+H]^+$:
m/z=477.3; Found: 477.3. The second peak (2.0 mg) reten-
tion time is 1.752 min. LCMS calcd for $C_{28}H_{41}N_6O$
$[M+H]^+$: m/z=477.3; Found: 477.3.

Example 13 trans-7-[(4-Aminocyclohexyl)methyl]-N-butyl-5-(4-
fluorophenyl)imidazo[5,1-f][1,2,4]triazin-2-amine

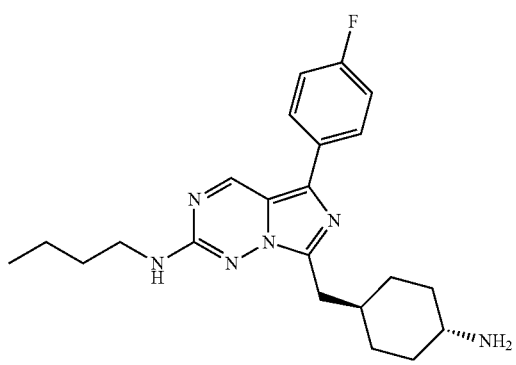 [SMILES: CCCCNc1ncc2c(-c3ccc(F)cc3)nc(C[C@H]3CC[C@H](N)CC3)n2n1]

Step 1.
[(tert-Butoxycarbonyl)amino](4-fluorophenyl)acetic
acid

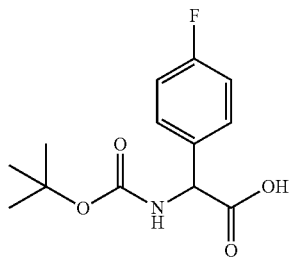 [SMILES: CC(C)(C)OC(=O)NC(C(=O)O)c1ccc(F)cc1]

To amino(4-fluorophenyl)acetic acid (from Acros, 3.0 g,
18 mmol) in 1.0 M sodium hydroxide in water (25.0 mL,
25.0 mmol), cooled in wet ice bath was added a solution of
di-tert-butyldicarbonate (4.6 g, 21 mmol) in isopropyl alco-
hol (15.0 mL). The ice bath was removed and the resulting
suspension was stirred at rt for 1 h. The volatile solvent was
removed under reduced pressure and remaining solution was
adjusted to pH=3 with 4M HCl, and then extracted with
Ethyl acetate. The organic fraction was washed with brine,
dried over sodium sulfate, filtered and concentrated to give 4.75 g (99%) of the desired product, which was used in the next step without further purification.

Step 2. tert-Butyl {1-(4-fluorophenyl)-2-[methoxy(methyl)amino]-2-oxoethyl}carbamate

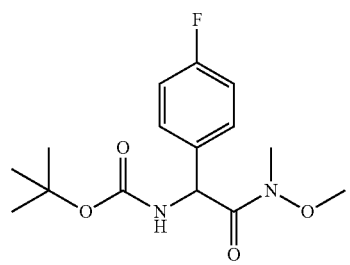 [SMILES: CON(C)C(=O)C(NC(=O)OC(C)(C)C)c1ccc(F)cc1]

To a mixture of [(tert-butoxycarbonyl)amino](4-fluorophenyl)acetic acid (1.25 g, 4.64 mmol), N,O-dimethylhydroxylamine hydrochloride (0.48 g, 4.9 mmol), N,N,N',N'-tetramethyl-O-(7-azabenzotriazol-1-yl)uronium hexafluorophosphate (2.6 g, 6.8 mmol) in 1,2-dichloroethane (15 mL) was added N,N-diisopropylethylamine (2.0 mL, 11 mmol). The reaction mixture was stirred at rt for 3 h. Solvent was evaporated under reduced pressure. The residue was partitioned between water and ethyl acetate. The aqueous fraction was washed with ethyl acetate. The organic fractions were combined, washed with brine, dried over sodium sulfate, filtered, and concentrated. The crude product was purified by silica gel column chromatography (20 g column, using gradient ethyl acetate-hexanes 0-50% in 25 min) to yield 1.30 g (90%) of the desired product. LCMS calcd for $C_{10}H_{13}FN_2O_2[M+H-Boc+H]^+$: m/z=213.1; Found: 213.1.

Step 3. tert-Butyl [2-(1,3-dithian-2-yl)-1-(4-fluorophenyl-2-oxoethyl]carbamate

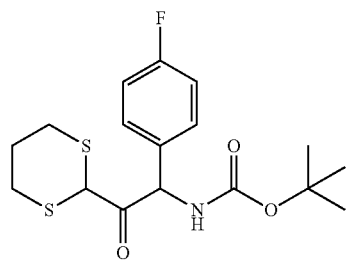 [SMILES: CC(C)(C)OC(=O)NC(C(=O)C1SCCCS1)c1ccc(F)cc1]

To a solution of 1,3-dithiane (3.30 g, 27.4 mmol) in dry tetrahydrofuran (20 mL) under nitrogen at −25° C. was added 2.5 M n-butyllithium in hexanes (11.0 mL, 27.5 mmol) drop-wise with vigorous stirring. After 2 h, a solution of tert-butyl {1-(4-fluorophenyl)-2-[methoxy(methyl)amino]-2-oxoethyl}carbamate (3.30 g, 10.6 mmol) in dry tetrahydrofuran (13 mL) was added drop-wise at −30° C. The resulting reaction mixture was allowed to warm to −15° C. and subsequently stirred for 1.5 h. The reaction was quenched with acetic acid (12.0 mL) at such a rate to keep the temperature below 15° C. To the mixture was added ethyl acetate (90 mL), water (90 mL) and the resulting mixture was stirred vigorously for 5 min. The aqueous fraction was separated, washed with ethyl acetate. The organic fractions were combined, washed with water (3×), saturated solution of sodium bicarbonate, brine, dried over sodium sulfate, filtered, and concentrated. To the oily residue was added heptane (60 mL), and crystals were formed as solution stood at rt overnight. The solid was filtered, rinsed with heptane, dried to give 3.50 g (89%) of white crystalline solid. LCMS calcd for $C_{17}H_{22}FNO_3S_2Na$ $[M+Na]^+$: m/z=394.1; Found: 394.1.

Step 4. tert-Butyl [(2Z)-2-[(aminocarbonothioyl)hydrazono]-2-(1,3-dithian-2-yl)-1-(4-fluorophenyl)ethyl]carbamate

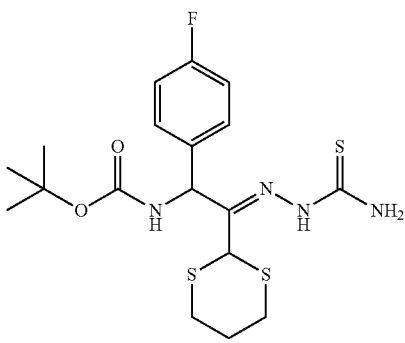 [SMILES: CC(C)(C)OC(=O)NC(/C(=N/NC(N)=S)C1SCCCS1)c1ccc(F)cc1]

To a solution of tert-butyl [2-(1,3-dithian-2-yl)-1-(4-fluorophenyl)-2-oxoethyl]carbamate (1.30 g, 3.50 mmol) in ethanol (15 mL) was added thiosemicarbazide (0.383 g, 4.20 mmol) followed by the addition of p-toluenesulfonic acid monohydrate (0.090 g, 0.48 mmol). The reaction mixture was heated at 80° C. for 94 h. The reaction mixture was allowed to cool to rt, concentrated under reduced pressure until the volume reached approximately 2 mL. To this residue was then added ethyl ether and solid precipitated overnight. The precipitate was collected by filtration. The ethyl ether mother liquid was concentrated and purified by silica gel column chromatography (24 g column, using gradient ethyl acetate-hexanes 0-30% in 25 min, 30-60% in 30 min) to give 0.52 g (32%) of the desired product as a cream color solid. LCMS calcd for $C_{18}H_{26}FN_4O_2S_3$ $[M+H]^+$: m/z=445.1; Found: 445.1.

Step 5. tert-Butyl {(4-fluorophenyl)[3-(methylthio)-1,2,4-triazin-6-yl]methyl}carbamate

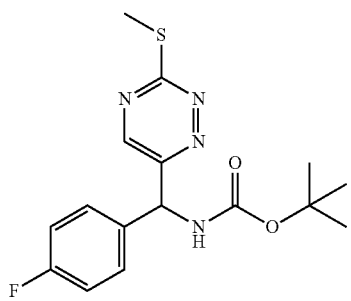 [SMILES: CSc1ncc(C(NC(=O)OC(C)(C)C)c2ccc(F)cc2)nn1]

To a stirred mixture of tert-butyl [(2Z)-2-[(aminocarbonothioyl)hydrazono]-2-(1,3-dithian-2-yl)-1-(4-fluorophenyl)ethyl]carbamate (0.050 g, 0.11 mmol) in acetonitrile (0.82 mL) and water (0.089 mL) was added calcium carbonate (0.034 g, 0.34 mmol), followed by slow addition (4×0.020 ml) of methyl iodide (0.080 mL, 1.3 mmol). The reaction mixture was heated at 40° C. for 2 d. The reaction mixture was diluted with ethyl acetate, solids were filtered off, rinsed with ethyl acetate. The organic phases were combined and concentrated. The crude residue was then purified by silica gel column chromatography to give the desired product (10 mg, 26%). LCMS calcd for $C_{16}H_{20}FN_4O_2S$ [M+H]$^+$: m/z=351.1; Found: 351.1.

Step 6. tert-Butyl {(4-fluorophenyl)[3-(methylsulfonyl)-1,2,4-triazin-6-yl]methyl}carbamate

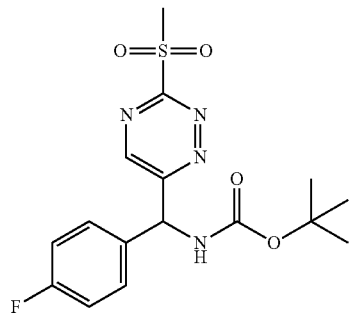 [SMILES: CC(C)(C)OC(=O)NC(c1ccc(F)cc1)c1cnc(S(C)(=O)=O)nn1]

To a stirred solution of tert-butyl {(4-fluorophenyl)[3-(methylthio)-1,2,4-triazin-6-yl]methyl}carbamate (0.098 g, 0.28 mmol) in methylene chloride (3.0 mL) was added m-chloroperbenzoic acid (0.144 g, 0.84 mmol). The reaction mixture was stirred at rt for 3 h, then diluted with dichloromethane and saturated solution of sodium bicarbonate. The organic layer was separated and washed with brine, dried over sodium sulfate, filtered and concentrated to give 0.098 g (89%) of crude product which was used in the next step without further purification. LCMS calcd for $C_{12}H_{12}FN_4O_4S$ [M+H-$^t$Bu+H]$^+$: m/z=327.1; Found: 327.0.

Step 7. tert-Butyl [[3-(butylamino)-1,2,4-triazin-6-yl](4-fluorophenyl)methyl]carbamate

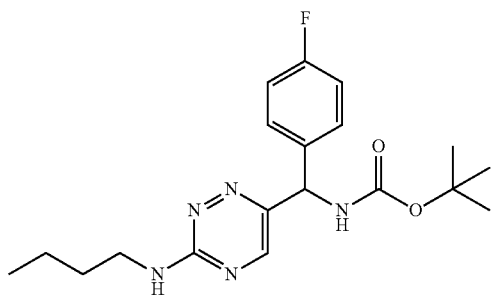 [SMILES: CCCCNc1ncc(C(NC(=O)OC(C)(C)C)c2ccc(F)cc2)nn1]

To tert-butyl {(4-fluorophenyl)[3-(methylsulfonyl)-1,2,4-triazin-6-yl]methyl}carbamate (0.110 g, 0.288 mmol) in tetrahydrofuran (1.50 mL) was added 1-butanamine (0.14 mL, 1.4 mmol). The reaction mixture in a capped tube was heated at 50° C. overnight. The reaction mixture was cooled, concentrated and purified by silica gel column chromatography (4 g column, using gradient: ethyl acetate-hexanes 0-30%) to yield 0.075 g (69%) of the desired product. LCMS calcd for $C_{19}H_{27}FN_5O_2$[M+H]$^+$: m/z=376.2; Found: 376.3.

Step 8. 6-[Amino(4-fluorophenyl)methyl]-N-butyl-1,2,4-triazin-3-amine dihydrochloride

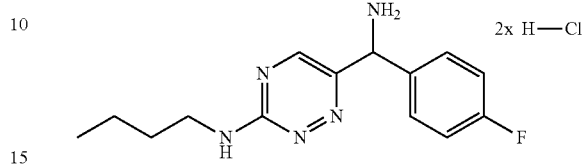

To tert-butyl [[3-(butylamino)-1,2,4-triazin-6-yl](4-fluorophenyl)methyl]carbamate (0.078 g, 0.21 mmol) was added 4.0 M hydrogen chloride in dioxane (1.2 mL, 4.8 mmol). The reaction mixture was stirred for 40 min. The volatiles were removed under reduced pressure to provide a colorless oil. The oil was then dissolved in ethyl acetate, and the volatiles were removed under reduced pressure to give a white solid. The crude product (as HCl salt) was used in the next step without further purifications. LCMS calcd for $C_{14}H_{19}FN_5$ [M+H]$^+$: m/z=276.2; Found: 276.2.

Step 9. tert-Butyl [trans-4-(2-{[[3-(butylamino)-1,2,4-triazin-6-yl](4-fluorophenyl)methyl]amino}-2-oxoethyl)cyclohexyl]carbamate

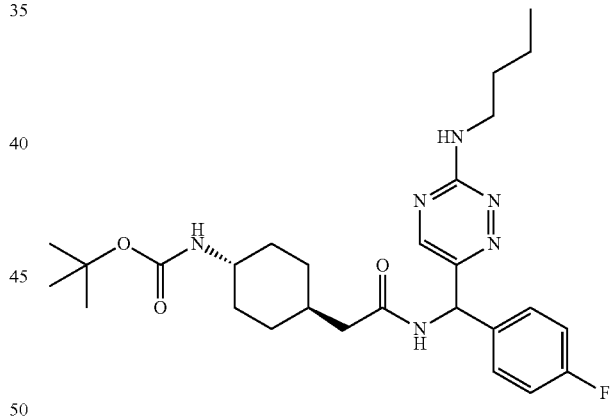

To a mixture of 6-[amino(4-fluorophenyl)methyl]-N-butyl-1,2,4-triazin-3-amine dihydrochloride (0.072 g, 0.21 mmol), {trans-4-[(tert-butoxycarbonyl)amino]cyclohexyl}acetic acid (from Chem-Impex, 0.0585 g, 0.227 mmol), and N,N,N',N'-tetramethyl-O-(7-azabenzotriazol-1-yl)uronium hexafluorophosphate (0.118 g, 0.310 mmol) in 1,2-dichloroethane (1.20 mL) was added N,N-diisopropylethylamine (0.14 mL, 0.80 mmol). The reaction mixture was stirred at rt for 30 min. The reaction mixture was diluted with ethyl acetate, washed with water (2×). The organic fraction was concentrated. The crude product was then purified by silica gel column chromatography (4 g column, using gradient MeOH-dichloromethane—0-3% in 15 min, 3-15% in 10 min) to give 0.084 (80%) of the desired product as a white solid. LCMS calcd for $C_{27}H_{40}FN_6O_3$[M+H]$^+$: m/z=515.3; Found: 515.2.

Step 10. trans-7-[(4-Aminocyclohexyl)methyl]-N-butyl-5-(4-fluorophenyl)imidazo[5,1-f][1,2,4]triazin-2-amine To the mixture of tert-butyl [trans-4-(2-{[[3-(butylamino)-1,2,4-triazin-6-yl](4-fluorophenyl)methyl]amino}-2-oxoethyl)cyclohexyl]carbamate (0.020 g, 0.039 mmol) and 1H-1,2,4-triazole (0.0099 g, 0.14 mmol) in anhydrous pyridine (0.600 mL) was added phosphoryl chloride (0.015 mL, 0.16 mmol). The reaction mixture was stirred at rt for 3.5 h. The reaction mixture was poured onto an ice cold water (20 mL) slowly with stirring. The pH was then adjusted to 7-8 with aqueous $NH_4OH$. The resulting mixture was extracted with ethyl acetate. The organic fraction was washed with brine, dried over sodium sulfate, filtered and concentrated to give crude tert-butyl (4-{[2-(butylamino)-5-(4-fluorophenyl)imidazo[5,1-f][1,2,4]triazin-7-yl]methyl}cyclohexyl)carbamate. To the crude intermediate was added 1.0 mL of 4 HCl in dioxane. The reaction mixture was stirred for 30 min. Solvent was then evaporated. The crude residue was purified on prep-LCMS (XBridge™ C18 column, eluting with a gradient of MeCN/water containing 0.05% TFA, at a flow rate of 60 mL/min) to give the desired products (6.3 mg as TFA salt). LCMS calcd for $C_{22}H_{30}FN_6$ [M+H]$^+$: m/z=397.2; Found: 397.3. $^1$H NMR (500 MHz, DMSO-d$_6$) □□ 9.24 (1H, s), 7.98 (2H, dd, J=5.0 and 5.0 Hz), 7.79 (2H, br s), 7.31 (1H, s), 7.26 (2H, dd, J=5.0 and 5.0 Hz), 3.22 (2H, dd, J=10 and 10 Hz), 2.93 (1H, m), 2.85 (2H, d, J=5.0 Hz), 1.90 (2H, m), 1.84 (1H, m), 1.74 (2H, m), 1.58 (2H, m), 1.37 (2H, m), 1.26 (2H, m), 1.15 (2H, m), 0.92 (3H, t, J=10 Hz) ppm.

Example 14 trans-7-((4-Aminocyclohexyl)methyl)-5-(4-fluorophenyl)-N-(3-phenylpropyl)imidazo [5,1-f][1,2,4]triazin-2-amine

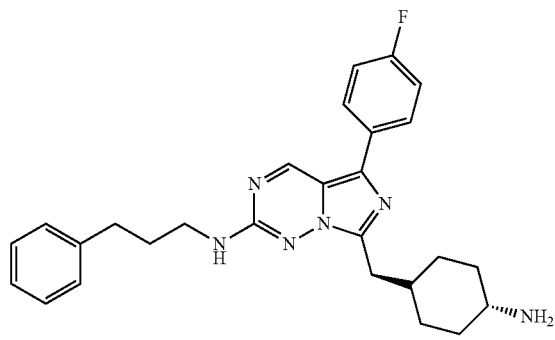

Step 1. 6-[Amino(4-fluorophenyl)methyl]-N-(3-phenylpropyl)-1,2,4-triazin-3-amine dihydrochloride

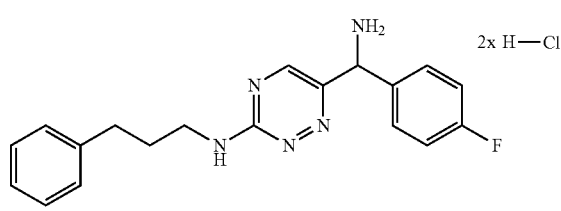 [SMILES: NC(c1ccc(F)cc1)c1cnc(NCCCc2ccccc2)nn1 ; Cl]

A mixture of tert-butyl {(4-fluorophenyl)[3-(methylsulfonyl)-1,2,4-triazin-6-yl]methyl}carbamate (Prepared in Example 13, Step 6; 0.090 g, 0.24 mmol) and benzenepropanamine (0.17 mL, 1.2 mmol) in tetrahydrofuran (1.30 mL) in a capped tube was heated at 50° C. overnight. Solvents were evaporated under reduced pressure. The residue was purified by silica gel column chromatography (4 g column, using gradient ethyl acetate-hexanes 0-30% in 25 min) to give 0.080 g of crude tert-butyl ((4-fluorophenyl){3-[(3-phenylpropyl)amino]-1,2,4-triazin-6-yl}methyl)carbamate as a white solid. LCMS calcd for $C_{24}H_{29}FN_5O_2$ [M+H]$^+$: m/z=438.2; Found: 438.2. To the crude intermediate was added 1.0 mL of 4N HCl in dioxane. The reaction mixture was stirred for 40 min. Solvents were evaporated under reduced pressure. To the residue was added AcCN, the resultant solution was concentrated to dryness under reduced pressure to yield the desired product, which was used in the next step without further purification. LCMS calcd for $C_{19}H_{21}FN_5$ [M+H]$^+$: m/z=338.2; Found: 338.2.

Step 2. tert-Butyl (trans-4-{2-[((4-fluorophenyl){3-[(3-phenylpropyl)amino]-1,2,4-triazin-6-yl}methyl)amino]-2-oxoethyl}cyclohexyl)carbamate

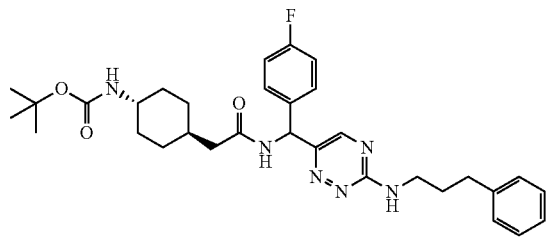 [SMILES: CC(C)(C)OC(=O)N[C@H]1CC[C@H](CC(=O)NC(c2ccc(F)cc2)c2cnc(NCCCc3ccccc3)nn2)CC1]

A mixture of 6-[amino(4-fluorophenyl)methyl]-N-(3-phenylpropyl)-1,2,4-triazin-3-amine dihydrochloride (0.075 g, 0.18 mmol), {trans-4-[(tert-butoxycarbonyl)amino]cyclohexyl}acetic acid (Chem-Impex, 0.0517 g, 0.201 mmol), N,N,N',N'-tetramethyl-O-(7-azabenzotriazol-1-yl)uronium hexafluorophosphate (0.104 g, 0.274 mmol) and N,N-diisopropylethylamine (0.13 mL, 0.75 mmol) in 1,2-dichloroethane (1.50 mL) was stirred at rt for 30 min. Solvent was evaporated under reduced pressure. The residue was diluted with ethyl acetate and washed with water (2×). The organic phase was concentrated in vacuo. The residue was purified on silica gel column chromatography (4 g column, using gradient methanol-dichloromethane 0-3% in 15 min, then 3-15% in 10 min) to give the desired product (0.058 g, 58%). LCMS calcd for $C_{32}H_{42}FN_6O_3$[M+H]$^+$: m/z=577.3; Found: 577.3.

Step 3. trans-7-((4-Aminocyclohexyl)methyl)-5-(4-fluorophenyl)-N-(3-phenylpropyl)imidazo[5,1-f][1,2,4]triazin-2-amine To the mixture of tert-butyl (trans-4-{2-[((4-fluorophenyl){3-[(3-phenylpropyl)amino]-1,2,4-triazin-6-yl}methyl)amino]-2-oxoethyl}cyclohexyl)carbamate (0.040 g, 0.069 mmol), 1H-1,2,4-triazole (0.019 g, 0.28 mmol) in anhydrous pyridine (1.066 mL) was added phosphoryl chloride (0.026 mL, 0.28 mmol) drop-wise. The reaction mixture was stirred at rt for 3 h. The reaction mixture was added drop-wise to an ice cold water (40 mL). The pH was then adjusted to ~7 with aqueous ammonium hydroxide, then extracted with ethyl acetate (2×). The organic layers were combined, washed with water (2×) and brine, dried over sodium sulfate, filtered and concentrated to give 0.020 g of trans-tert-butyl 4-((5-(4-fluorophenyl)-2-(3-phenylpropylamino)imidazo[5,1-f][1,2,4]triazin-7-yl)methyl)cyclohexylcarbamate. To the crude intermediate was added 1 mL of 4N HCl in dioxane. The reaction mixture was stirred for 30 min, then evaporated to dryness. The crude residue was purified on prep-LCMS (XBridge™ C18 column, eluting with a gradient of MeCN/water containing 0.05% TFA, at a flow rate of 60 mL/min) to afford the desired product (2.8 mg) as TFA salt. LCMS calcd for $C_{27}H_{32}FN_6$ $[M+H]^+$: m/z=459.3; Found: 459.3.

Example 15

7-(4-Aminocyclohexyl)-N-butyl-5-(4-fluorophenyl)imidazo[5,1-f][1,2,4]triazin-2-amine (cis- and trans-)

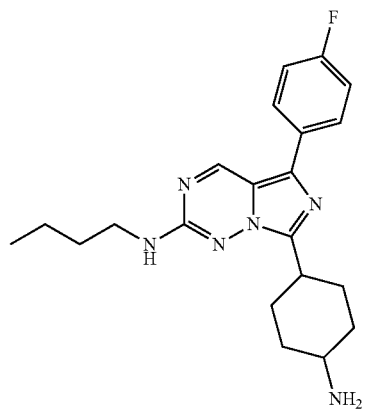 [SMILES: CCCCNc1ncc2c(-c3ccc(F)cc3)nc(C3CCC(N)CC3)n2n1]

Step 1. tert-Butyl [4-({[[3-(butylamino)-1,2,4-triazin-6-yl](4-fluorophenyl)methyl]amino}carbonyl)cyclohexyl]carbamate

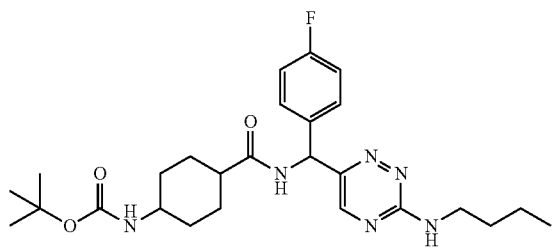 [SMILES: CCCCNc1ncc(C(NC(=O)C2CCC(NC(=O)OC(C)(C)C)CC2)c2ccc(F)cc2)nn1]

A mixture of 6-[amino(4-fluorophenyl)methyl]-N-butyl-1,2,4-triazin-3-amine dihydrochloride (Prepared in Example 13, Step 8; 0.080 g, 0.23 mmol), 4-[(tert-butoxycarbonyl)amino]cyclohexanecarboxylic acid (CNH Technologies; 0.073 g, 0.30 mmol), N,N,N',N'-tetramethyl-O-(7-azabenzotriazol-1-yl)uronium hexafluorophosphate (0.131 g, 0.344 mmol) and N,N-diisopropylethylamine (0.16 mL, 0.92 mmol) in 1,2-dichloroethane (1.20 mL) was stirred at rt overnight. The reaction mixture was diluted with ethyl acetate, washed with water (2×), brine, dried over sodium sulfate, filtered and concentrated. The crude residue was purified by silica gel column chromatography (4 g column, using gradient methanol-dichloromethane 0-3% in 15 min, then 3-15% in 10 min) to give the desired product (0.090 g, 78%). LCMS calcd for $C_{26}H_{38}FN_6O_3[M+H]^+$: m/z=501.3; Found: 501.2.

Step 2. 7-(4-Aminocyclohexyl)-N-butyl-5-(4-fluorophenyl)imidazo[5,1-f][1,2,4]triazin-2-amine To a mixture of tert-butyl [4-({[[3-(butylamino)-1,2,4-triazin-6-yl](4-fluorophenyl)methyl]amino}carbonyl)cyclohexyl]carbamate (0.090 g, 0.18 mmol), 1H-1,2,4-triazole (0.050 g, 0.72 mmol) in anhydrous pyridine (2.0 mL) was added phosphoryl chloride (0.067 mL, 0.72 mmol). The reaction mixture was stirred at rt overnight. The reaction mixture was added to an ice cold water (40 mL) drop-wise with stirring. The pH was then adjusted to ~7 with aqueous $NH_4OH$. The resulting mixture was extracted with ethyl acetate. The organic layer was washed with water (3×), brine, dried over sodium sulfate, filtered and concentrated to give crude tert-butyl {4-[2-(butylamino)-5-(4-fluorophenyl)imidazo[5,1-f][1,2,4]triazin-7-yl]cyclohexyl}carbamate. LCMS calcd for $C_{26}H_{36}FN_6O_2[M+H]^+$: m/z=483.3; Found: 483.3. To the crude intermediate was added 1 mL of 4N HCl in dioxane. The reaction mixture was stirred for 45 min. Solvents were evaporated under reduced pressure. The crude residue was purified on prep-LCMS (XBridge™ C18 column, eluting with a gradient of MeCN/water containing 0.05% TFA, at a flow rate of 60 mL/min) to afford the desired product (2.8 mg) as TFA salt. LCMS calcd for $C_{21}H_{28}FN_6$ $[M+H]^+$: m/z=383.2; Found: 383.3.

Example A

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM MgCl2 and 2 mM DTT at room temperature for 1 hour.

TAM Enzymatic Assay

The kinase assay buffer contained 50 mM HEPES, pH7.5, 10 mM MgCl2, 1 mM EGTA, 0.01% NP-40 and 2 mM DTT. 0.1 ul test compounds dissolved in DMSO were transferred from compound plates to white 384-well assay plates (Greiner LUMITRAC plates). The final concentration of DMSO was 1.25%. Enzyme solutions of 5.1 nM phosphor-Axl, or 0.0625 nM c-Mer (Carna Biosciences, 08-108), or 0.366 nM Tyro3 (Life Technologies, PR7480A) were prepared in assay buffer. A 1 mM stock solution of peptide substrate Biotin-EQEDEPEGDYFEWLE-amide SEQ ID NO: 1 (Quality Controlled Biochemicals, MA) dissolved in DMSO was diluted to 1 uM in assay buffer containing 2000 uM ATP. 4 ul enzyme solution (or assay buffer for the enzyme blank) was added to the appropriate wells in each plate, and then 4 ul/well substrate solution was added to initiate the reaction. The plate was protected from light and incubated at room temperature for 60 min. The reaction was stopped by adding 4 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu-W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The compounds of the invention were found to be inhibitors of TAM according to the TAM Enzymatic Assay. Compounds of Formula (I) and all the compounds as described herein have been tested and exhibit an $IC_{50}$ of less than 1 µM.

The compounds of the invention were found to be inhibitors of one or more of AXL, MER, and TYRO3. $IC_{50}$ data is provided below in Table 1. The symbol "+" indicates an $IC_{50}$ of ≤100 nM, "++" indicates an $IC_{50}$ of >100 nM but ≤500 nM. "+++" indicates an $IC_{50}$ of >500 nM but ≤1000 nM; and "++++" indicates an $IC_{50}$ of greater than 1000 nM. The term "n/t" means not tested.

TABLE 1

| Example | Mer $IC_{50}$ (nM) | Phos-Axl $IC_{50}$ (nM) | Tyro3 $IC_{50}$ (nM) |
|---|---|---|---|
| 1 (1$^{st}$ peak, trans-) | + | + | ++ |
| 1 (2$^{nd}$ peak, cis-) | + | n/t | ++ |
| 2 (1$^{st}$ peak, trans-) | + | n/t | ++ |
| 2 (2$^{nd}$ peak, cis-) | + | ++ | ++ |
| 3 (1$^{st}$ peak, trans-) | + | n/t | n/t |
| 3 (2$^{nd}$ peak, cis-) | ++++ | n/t | n/t |
| 4 (1$^{st}$ peak) | + | +++ | n/t |
| 4 (2$^{nd}$ peak) | ++ | n/t | n/t |
| 5 (1$^{st}$ peak, trans-) | + | ++ | ++ |
| 5 (2$^{nd}$ peak, cis-) | ++ | ++ | n/t |
| 6 (1$^{st}$ peak, trans-) | + | ++ | n/t |
| 6 (2$^{nd}$ peak, cis-) | ++ | n/t | n/t |
| 7 (1$^{st}$ peak) | + | ++ | +++ |
| 7 (2$^{nd}$ peak) | ++ | ++++ | n/t |
| 8 (1$^{st}$ peak) | + | n/t | n/t |
| 8 (2$^{nd}$ peak) | n/t | n/t | n/t |
| 9 (1$^{st}$ peak) | + | n/t | n/t |
| 9 (2$^{nd}$ peak) | ++ | n/t | n/t |
| 10 (1$^{st}$ peak) | + | n/t | n/t |
| 10 (2$^{nd}$ peak) | ++ | n/t | n/t |
| 11 (1$^{st}$ peak) | ++ | ++++ | ++++ |
| 11 (2$^{nd}$ peak) | + | ++ | +++ |
| 12 (1$^{st}$ peak) | ++ | ++ | ++ |
| 12 (2$^{nd}$ peak) | + | + | ++ |
| 13 | + | ++ | +++ |
| 14 | + | n/t | ++++ |
| 15 | + | ++ | n/t |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is clamed is:
1. A compound of Formula IV:

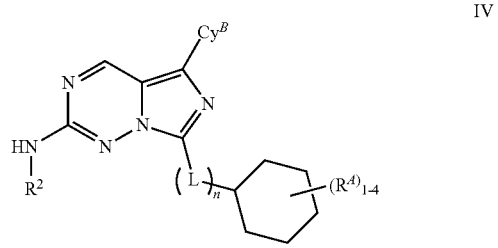

or a pharmaceutically acceptable salt thereof, wherein:
$R^2$ is $C_{1-6}$ alkyl or 6-10 membered aryl-$C_{1-4}$ alkylene;
L is —$C_{1-6}$ alkylene;
n is 0 or 1;
each $R^A$ is independently selected from OH, $C_{1-6}$ alkoxy, amino, $C_{1-6}$ alkylamino, and di($C_{1-6}$ alkyl)amino;
$Cy^B$ is 6-10 membered aryl or 5-10 membered heteroaryl, each of which is optionally substituted by 1, 2, 3, or 4 independently selected $R^B$ groups;
each $R^B$ is independently selected from halo, $C_{1-6}$ alkyl, 4-6 membered heterocycloalkyl, 4-6 membered heterocycloalkyl-$C_{1-4}$ alkylene, and $NR^{c2}C(O)R^{b2}$; wherein said $C_{1-6}$ alkyl, 4-6 membered heterocycloalkyl, and 4-6 membered heterocycloalkyl-$C_{1-4}$ alkylene are optionally substituted with 1, 2, 3, or 4 independently selected $R^{12}$ groups;
each $R^{12}$ is independently selected from halo, CN, $C_{1-6}$ alkyl, $C_{1-4}$ haloalkyl, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}S(O)_2R^{b3}$, $NR^{c3}S(O)_2NR^{c3}R^{d3}$; $S(O)_2R^{b3}$, and $S(O)_2NR^{c3}R^{d2}$;
each $R^{c2}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl; wherein said $C_{1-6}$ alkyl, $C_{1-4}$ haloalkyl, $C_{3-7}$ cycloalkyl, phenyl, 5-6 membered heteroaryl, and 4-6 membered heterocycloalkyl are each optionally substituted with 1, 2, or 3 independently selected $R^{12}$ groups;
each $R^{b2}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl; each of which is optionally substituted with 1, 2, or 3 independently selected $R^{12}$ groups;
$R^{a3}$, $R^{c3}$, and $R^{d3}$ is independently selected from H, $C_{1-6}$ alkyl, $C_{1-4}$ haloalkyl, $C_{3-7}$ cycloalkyl, phenyl, 5-6 membered heteroaryl, and 4-6 membered heterocycloalkyl; and each $R^{b3}$ is independently selected from $C_{1-6}$ alkyl, $C_{1-4}$ haloalkyl, $C_{3-7}$ cycloalkyl, phenyl, 5-6 membered heteroaryl, and 4-6 membered heterocycloalkyl.

2. The compound of claim 1, or a pharmaceutically acceptable salt thereof, wherein $Cy^B$ is phenyl, a pyridine ring, or an indole ring, each of which is optionally substituted by 1, 2, 3, or 4 independently selected $R^B$ groups.

3. The compound of claim 1, or a pharmaceutically acceptable salt thereof, wherein each $R^{12}$ is independently selected from $C_{1-6}$ alkyl, $OR^{a3}$ and $NR^{c3}R^{d3}$.

4. The compound of claim 1, or a pharmaceutically acceptable salt thereof, wherein each $R^B$ is independently selected from F, —$CH_2$-(piperazinyl), —$CH_2$-(4-methylpiperazinyl), —$CH_2$-(morpholin-4-yl), —$CH_2$—$OR^{a3}$, —$CH_2$—$NR^{c3}R^{d3}$, and $NR^{c2}C(O)R^{b2}$; each $R^{c2}$ is H or $C_{1-6}$ alkyl; each $R^{b2}$ is $C_{1-6}$ alkyl; each $R^{a3}$ is H or $C_{1-6}$ alkyl; and each $R^{c3}$ and $R^{d3}$ is independently selected from H, $C_{1-6}$ alkyl, and $C_{3-6}$ cycloalkyl.

5. The compound of claim 1, or a pharmaceutically acceptable salt thereof, wherein n is 1.

6. The compound of claim 1, or a pharmaceutically acceptable salt thereof, wherein n is 0.

7. The compound of claim 1, or a pharmaceutically acceptable salt thereof, wherein:
$R^2$ is n-butyl or phenylpropyl;
n is 0 or 1;
L is —$CH_2$—;
$R^A$ is OH or amino;
$Cy^B$ is phenyl, a pyridine ring, or an indole ring, each of which is optionally substituted by 1 or 2 independently selected $R^B$ groups;
each $R^B$ is independently selected from F, —$CH_2$-(piperazinyl), —$CH_2$-(4-methylpiperazinyl), —$CH_2$-(morpholin-4-yl), —$CH_2$—$OR^{a3}$, —$CH_2$—$NR^{c3}R^{d3}$, and $NR^{c2}C(O)R^{b2}$;
each $R^{c2}$ is independently H or $C_{1-6}$ alkyl;
each $R^{b2}$ is independently $C_{1-6}$ alkyl;
each $R^{a3}$ is independently H or $C_{1-6}$ alkyl; and
each $R^{c3}$ and $R^{d3}$ is independently selected from H, $C_{1-6}$ alkyl, and $C_{3-6}$ cycloalkyl.

8. The compound of claim 1, having Formulae IVa or IVb:

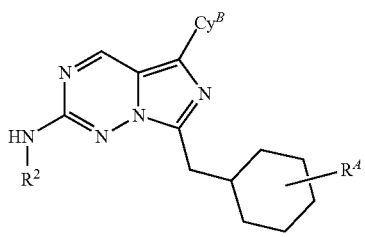

IVa

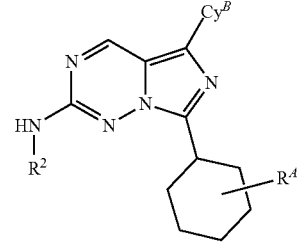

IVb or a pharmaceutically acceptable salt thereof.

9. The compound of claim 1 selected from:
4-(2-(Butylamino)-5-{4-[(4-methylpiperazin-1-yl)methyl]phenyl}imidazo[5,1-f][1,2,4]triazin-7-yl)cyclohexanol;
4-{2-(Butylamino)-5-[4-(morpholin-4-ylmethyl)phenyl]imidazo[5,1-f][1,2,4]triazin-7-yl}cyclohexanol;
4-{2-(Butylamino)-5-[4-(hydroxymethyl)phenyl]imidazo[5,1-f][1,2,4]triazin-7-yl}cyclohexanol;
4-[2-(Butylamino)-5-(1H-indol-5-yl)imidazo[5,1-f][1,2,4]triazin-7-yl]cyclohexanol;
4-[2-(Butylamino)-5-(4-piperazin-1-ylphenyl)imidazo[5,1-f][1,2,4]triazin-7-yl]cyclohexanol;
4-[2-(Butylamino)-5-(2-piperazin-1-ylpyridin-4-yl)imidazo[5,1-f][1,2,4]triazin-7-yl]cyclohexanol;
4-[2-(Butylamino)-5-(3-fluoro-4-morpholin-4-ylphenyl)imidazo[5,1-f][1,2,4]triazin-7-yl]cyclohexanol;
4-{2-(Butylamino)-5-[3-(hydroxymethyl)phenyl]imidazo[5,1-f][1,2,4]triazin-7-yl}cyclohexanol;
N-{3-[2-(Butylamino)-7-(4-hydroxycyclohexyl)imidazo[5,1-f][1,2,4]triazin-5-yl]phenyl}acetamide;
N-{4-[2-(Butylamino)-7-(4-hydroxycyclohexyl)imidazo[5,1-f][1,2,4]triazin-5-yl]phenyl}acetamide;
4-(2-(Butylamino)-5-{4-[(methylamino)methyl]phenyl}imidazo[5,1-f][1,2,4]triazin-7-yl)cyclohexanol;
4-(2-(Butylamino)-5-{4-[(cyclohexylamino)methyl]phenyl}imidazo[5,1-f][1,2,4]triazin-7-yl)cyclohexanol;
7-[(4-Aminocyclohexyl)methyl]-N-butyl-5-(4-fluorophenyl)imidazo[5,1-f][1,2,4]triazin-2-amine;
7-((4-Aminocyclohexyl)methyl)-5-(4-fluorophenyl)-N-(3-phenylpropyl)imidazo[5,1-f][1,2,4]triazin-2-amine; and
7-(4-Aminocyclohexyl)-N-butyl-5-(4-fluorophenyl)imidazo[5,1-f][1,2,4]triazin-2-amine;
or a pharmaceutically acceptable salt of any of the aforementioned.

10. The compound of claim 9, or a pharmaceutically acceptable salt thereof, wherein the compound or salt is in cis- configuration.

11. The compound of claim 9, or a pharmaceutically acceptable salt thereof, wherein the compound or salt is in trans- configuration.

12. A pharmaceutical composition comprising a compound of claim 1, or a pharmaceutically acceptable salt thereof, and a pharmaceutically acceptable carrier.

13. A method for inhibiting a TAM kinase in vitro, said method comprising: contacting the TAM kinase with the compound of claim 1, or a pharmaceutically acceptable salt thereof.

14. The compound of claim 1, or a pharmaceutically acceptable salt thereof, wherein:
each $R^{c2}$ is independently H or $C_{1-6}$ alkyl;
each $R^{b2}$ is independently $C_{1-6}$ alkyl;
each $R^{12}$ is independently selected from $C_{1-6}$ alkyl, $OR^{a3}$, and $NR^{c3}R^{d3}$;
each $R^{a3}$ is independently H or $C_{1-6}$ alkyl; and
each $R^{c3}$ and $R^{d3}$ is independently selected from H, $C_{1-6}$ alkyl, and $C_{3-6}$ cycloalkyl.

* * * * *

UNITED STATES PATENT AND TRADEMARK OFFICE
CERTIFICATE OF CORRECTION

PATENT NO. : 9,708,333 B2
APPLICATION NO. : 15/234690
DATED : July 18, 2017
INVENTOR(S) : Yun-Long Li and David M. Burns Page 1 of 1

It is certified that error appears in the above-identified patent and that said Letters Patent is hereby corrected as shown below:

In the Claims

Column 102, Line 16, Claim 1 delete "—$C_{1-6}$ alkylene;" and insert -- —$C_{1-6}$ alkylene—; --.

Column 102, Lines 34-35, Claim 1 delete "$NR^{c3}S(O)_2NR^{c3}R^{d3}$;" and insert -- $NR^{c3}S(O)_2NR^{c3}R^{d3}$, --.

Column 102, Line 35, Claim 1 delete "$S(O)_2NR^{c3}R^{d2}$;" and insert -- $S(O)_2NR^{c3}R^{d3}$; --.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*